United States Patent
Karaborni et al.

(10) Patent No.: US 11,690,811 B2
(45) Date of Patent: Jul. 4, 2023

(54) PHARMACEUTICAL COMPOSITIONS AND ORAL DOSAGE FORMS OF KETAMINE DERIVATIVES

(71) Applicant: XWPHARMA LTD., Grand Cayman (KY)

(72) Inventors: Sami Karaborni, Cupertino, CA (US); Daniel M. Canafax, Half Moon Bay, CA (US); William W. Xiang, Fremont, CA (US); Jia-Ning Xiang, Fremont, CA (US)

(73) Assignee: XWPHARMA LTD., Grand Cayman (KY)

( * ) Notice: Subject to any disclaimer, the term of this patent is extended or adjusted under 35 U.S.C. 154(b) by 0 days.

(21) Appl. No.: 17/887,049

(22) Filed: Aug. 12, 2022

(65) Prior Publication Data

US 2023/0098084 A1 Mar. 30, 2023

Related U.S. Application Data

(60) Provisional application No. 63/232,717, filed on Aug. 13, 2021.

(51) Int. Cl.
*A61K 31/135* (2006.01)
*A61K 9/20* (2006.01)
*A61K 9/00* (2006.01)

(52) U.S. Cl.
CPC .......... *A61K 31/135* (2013.01); *A61K 9/2013* (2013.01); *A61K 9/2054* (2013.01); *A61K 9/0053* (2013.01)

(58) Field of Classification Search
None
See application file for complete search history.

(56) References Cited

U.S. PATENT DOCUMENTS

| | | | |
|---|---|---|---|
| 5,648,087 A | 7/1997 | Ovaert et al. | |
| 5,837,730 A | 11/1998 | Javitt | |
| 6,248,789 B1 | 6/2001 | Weg | |
| 11,110,070 B2 | 9/2021 | Brachman et al. | |
| 2004/0248964 A1 | 12/2004 | Crooks et al. | |
| 2008/0268071 A1* | 10/2008 | Gant | A61P 25/28 514/646 |
| 2013/0237559 A1* | 9/2013 | Ortiz | A61K 31/135 514/646 |
| 2014/0079740 A1 | 3/2014 | Salama | |
| 2015/0259277 A1 | 9/2015 | Sleigh et al. | |
| 2018/0098993 A1 | 4/2018 | Wainer et al. | |
| 2018/0177744 A1 | 6/2018 | Jay | |
| 2018/0289637 A1 | 10/2018 | Laufer et al. | |
| 2019/0240184 A1 | 8/2019 | Hashimoto | |
| 2019/0322618 A1* | 10/2019 | Xiang | C07D 213/81 |
| 2020/0306194 A1 | 10/2020 | Glue et al. | |

FOREIGN PATENT DOCUMENTS

| | | |
|---|---|---|
| CN | 104395283 | 3/2015 |
| CN | 111836798 | 10/2020 |
| EA | 201590697 | 9/2015 |
| JP | 2006-510618 | 3/2006 |
| JP | 2009-509982 | 3/2009 |
| JP | 2015-501302 | 1/2015 |
| JP | 2015-535847 | 12/2015 |
| WO | 97/07750 | 3/1997 |
| WO | 2004/045601 | 6/2004 |
| WO | 2008/134525 | 11/2008 |
| WO | 2011/109799 | 9/2011 |
| WO | 2013/019561 | 2/2013 |
| WO | 2013/056229 | 4/2013 |
| WO | 2013/170068 | 11/2013 |
| WO | 2014/057414 | 4/2014 |
| WO | 2014/205389 | 12/2014 |
| WO | 2014/205393 | 12/2014 |
| WO | 2017/087388 | 5/2017 |
| WO | 2017/117529 | 7/2017 |
| WO | 2017/180589 A1 | 10/2017 |
| WO | 2017/208031 | 12/2017 |
| WO | 2018/079693 | 5/2018 |
| WO | 2018/234568 A2 | 12/2018 |
| WO | 2019/137381 A1 | 7/2019 |

OTHER PUBLICATIONS

International Search Report and Written Opinion for Application No. PCT/CN2018/090151, dated Feb. 20, 2019, 14 pages.
International Search Report and Written Opinion for Application No. PCT/CN2019/070912, dated Mar. 27, 2019, 11 pages.
International Search Report and Written Opinion for Application No. PCT/CN2019/090189, dated Sep. 18, 2019, 15 pages.
International Search Report and Written Opinion for Application No. PCT/CN2019/095144, dated Sep. 26, 2019, 11 pages.
Non-Final Office Action for U.S. Appl. No. 16/502,562, dated Nov. 5, 2019, 42 pages.
Registry RN 1430202-54-2, Oct. 21, 2013.
Dakwar et al., "A Single Ketamine Infusion Combined with Motivational Enhancement Therapy for Alcohol Use Disorder: A Randomized Midazolam-Controlled Pilot Trial", American Journal Psychiatry, Feb. 2020, vol. 177, No. 2, p. 125-133.
Dimitrov et al., "Ketamine esters and amides as short-acting anaesthetics: Structure-activity relationships for the side-chain", Bioorganic & Medicinal Chemistry, 2019, vol. 27, pp. 1226-1231.
Ebert et al., "Norketamine, the main metabolite of ketamine, in a non-competitive NMDA receptor antagonist in the rat cortex and spinal cord", European Journal of Pharmacology, 1997, vol. 333, p. 99-104.
Fawcett et al., "Anxiety Syndromes and Their Relationship to Depressive Illness", Journal of Clinical Psychiatry, 1983, vol. 44, p. 8-11.
Feder et al., "Efficacy of Intravenous Ketamine for Treatment of Chronic Posttraumatic Stress Disorder: A Randomized Clinical Trial", JAMA Psychiatry, vol. 71, No. 6, 2014, p. 681-688.
Feder et al., "A Randomized Controlled Trial of Repeated Ketamine Administration for Chronic Posttraumatic Stress Disorder", American Journal of Psychiatry, Feb. 2021, vol. 178, No. 2, pp. 193-202.

(Continued)

*Primary Examiner* — Bong-Sook Baek

(57) ABSTRACT

Pharmaceutical compositions of ketamine derivatives and oral dosage forms comprising the pharmaceutical compositions are disclosed. Solid oral dosage forms prepared from the pharmaceutical compositions exhibit a zero-order release profile.

8 Claims, 8 Drawing Sheets

(56) References Cited

OTHER PUBLICATIONS

Jose, J. et al., "Structure-activity relationships for ketamine esters as short-acting anaesthetics", Bioorganic & Medicinal Chemistry, Sep. 2013, vol. 21, Issue 17, p. 5098-5106.
Lahti et al., "Ketamine activates psychosis and alters limbic blood flow in schizophrenia", Clinical Neuroscience and Neuropathy, NeuroReport, 1995, vol. 6, p. 869-872.
Liriano et al., "Ketamine as treatment for post-traumatic stress disorder: a review", Drugs in Context, 3:212305, 2019, pp. 1-7.
Mayo Clinic, Depression (major depressive disorder), Mayo Foundation for Medical Education and Research, 1998-2021, 5 pages.
Mollaahmetoglu et al., "This is Something That Changed My Life: A Qualitative Study of Patients' Experiences in a Clinical Trial of Ketamine Treatment for Alcohol Use Disorders", Frontiers in Psychiatry, Aug. 2021, vol. 12, Article 695335, 17 pages.
Morgan et al., "Is Persistent Ketamine Use a Valid Model of the Cognitive and Ocular Deficits in Schizophrenia?", Biol Psychiatry, 2009, vol. 65, p. 1099-1102.
Nielsen et al., "Intraoperative S-ketamine for the reduction of opioid consumption and pain one year after spine surgery: A randomized clinical trial of opioid-dependent patients", Eur J Pain, Jul. 2018, 2019, vol. 23, pp. 455-460.
Rodriguez et al., "Randomized Controlled Crossover Trial of Ketamine in Obsessive-Compulsive Disorder: Proof-of-Concept", Neuropsychopharmacology, 2013, vol. 38, p. 2475-2483.
Sanacora et al., "A Consensus Statement on the Use of Ketamine in the Treatment of Mood Disorder", JAMA Psychiatry, Clinical Review and Education Special Communication, 2017, 24 pages.
Search Report for Australia Application No. 2019206950, dated Oct. 26, 2020, 7 pages.
Search Report for Russia Application No. 2020126393 dated Dec. 1, 2020, 2 pages.
Search Report and Written Opinion for Singapore Application No. 11202006575T, dated Oct. 4, 2021, 12 pages.
Taylor et al., "Ketamine for Social Anxiety Disorder: A Randomized, Placebo-Controlled Crossover Trial", Neuropsychopharmacology, 2018, vol. 43, p. 325-333.
Zhao et al., "Simultaneous population pharmacokinetic modelling of ketamine and three major metabolites in patients with treatment-resistant bipolar depression", British Journal of Clinical Pharmacology, 2012, vol. 74, pp. 304-314.
International Search Report and Written Opinion for Application No. PCT/US2022/040217, dated Nov. 30, 2022, 14 pages.

\* cited by examiner

| Analyte | Parameter | Units | IR | | | MR-1 | | | MR-2 | | | MR-3 | | |
|---|---|---|---|---|---|---|---|---|---|---|---|---|---|---|
| | | | N | Mean | SE | N | Mean | SE | N | Mean | SE | N | Mean | SE |
| Esketamine | Tmax | hr | 12 | 0.8 | 0.1 | 12 | 2.9 | 0.9 | 12 | 5.7 | 3.9 | 12 | 5.2 | 1.5 |
| | Cmax | ng/mL | 12 | 40.6 | 6.4 | 12 | 7.5 | 1.5 | 12 | 11.5 | 2.5 | 12 | 5.6 | 1.0 |
| | AUClast | hr×ng/mL | 12 | 87.1 | 13.0 | 12 | 46.2 | 9.0 | 12 | 58.8 | 11.8 | 12 | 51.2 | 8.2 |
| | AUCinf | hr×ng/mL | 12 | 94.6 | 13.9 | 4 | 82.5 | 21.5 | 6 | 73.4 | 10.7 | 3 | 106.8 | 12.7 |
| | AUC0-4 | hr×ng/mL | 12 | 65.2 | 8.8 | 12 | 13.1 | 2.3 | 12 | 19.8 | 5.0 | 12 | 11.7 | 2.4 |
| | AUC0-5 | hr×ng/mL | 12 | 70.3 | 9.5 | 12 | 17.0 | 3.4 | 12 | 23.3 | 5.6 | 12 | 13.8 | 2.9 |
| | AUC0-6 | hr×ng/mL | 12 | 73.9 | 9.9 | 12 | 20.3 | 4.1 | 12 | 26.5 | 5.9 | 12 | 15.5 | 3.2 |
| | AUC0-7 | hr×ng/mL | 12 | 76.5 | 10.3 | 12 | 23.0 | 4.7 | 12 | 29.3 | 6.1 | 12 | 17.0 | 3.6 |
| | AUC0-8 | hr×ng/mL | 12 | 78.6 | 10.6 | 12 | 25.0 | 5.1 | 12 | 31.7 | 6.3 | 12 | 18.4 | 3.9 |
| | AUC0-12 | hr×ng/mL | 12 | 84.4 | 11.6 | 12 | 31.0 | 5.8 | 12 | 38.8 | 6.6 | 12 | 26.4 | 4.9 |
| | C4 | ng/mL | 12 | 5.9 | 0.9 | 12 | 4.2 | 1.5 | 12 | 3.7 | 0.8 | 12 | 2.2 | 0.5 |
| | C5 | ng/mL | 12 | 4.4 | 0.7 | 12 | 3.6 | 1.1 | 12 | 3.3 | 0.5 | 12 | 1.9 | 0.4 |
| | C6 | ng/mL | 12 | 2.8 | 0.4 | 12 | 3.0 | 0.9 | 12 | 3.0 | 0.4 | 12 | 1.6 | 0.4 |
| | C7 | ng/mL | 12 | 2.3 | 0.4 | 12 | 2.3 | 0.6 | 12 | 2.6 | 0.3 | 12 | 1.4 | 0.4 |
| | C8 | ng/mL | 12 | 1.8 | 0.4 | 12 | 1.7 | 0.4 | 12 | 2.2 | 0.3 | 12 | 1.2 | 0.4 |
| | t1/2 | hr | 12 | 4.0 | 0.7 | 4 | 6.5 | 4.1 | 6 | 5.8 | 1.4 | 3 | 13.2 | 2.7 |
| Noresketamine | Tmax | hr | 12 | 1.1 | 0.1 | 12 | 3.2 | 0.9 | 12 | 5.8 | 3.9 | 12 | 5.5 | 2.0 |
| | Cmax | ng/mL | 12 | 217.8 | 20.7 | 12 | 70.2 | 13.3 | 12 | 113.9 | 32.1 | 12 | 50.5 | 4.9 |
| | AUClast | hr×ng/mL | 12 | 1081.3 | 69.4 | 12 | 817.6 | 59.1 | 12 | 1048.2 | 199.3 | 12 | 890.1 | 51.6 |
| | AUCinf | hr×ng/mL | 12 | 1116.5 | 73.3 | 11 | 923.6 | 73.1 | 10 | 931.2 | 80.5 | 10 | 985.2 | 75.2 |

FIG. 5

|          |          |    |       |      |    |       |      |    |       |      |    |       |      |
|----------|----------|----|-------|------|----|-------|------|----|-------|------|----|-------|------|
| AUC0-4   | hr×ng/mL | 12 | 492.8 | 21.9 | 12 | 143.7 | 20.1 | 12 | 197.4 | 32.4 | 12 | 128.0 | 13.0 |
| AUC0-5   | hr×ng/mL | 12 | 561.3 | 24.3 | 12 | 190.5 | 28.8 | 12 | 246.8 | 40.6 | 12 | 159.2 | 16.4 |
| AUC0-6   | hr×ng/mL | 12 | 616.3 | 26.8 | 12 | 233.5 | 36.4 | 12 | 291.0 | 46.4 | 12 | 186.7 | 19.3 |
| AUC0-7   | hr×ng/mL | 12 | 661.2 | 29.2 | 12 | 272.0 | 43.4 | 12 | 331.1 | 50.6 | 12 | 211.4 | 21.6 |
| AUC0-8   | hr×ng/mL | 12 | 699.8 | 31.4 | 12 | 305.2 | 49.2 | 12 | 368.2 | 54.1 | 12 | 234.4 | 23.7 |
| AUC0-12  | hr×ng/mL | 12 | 819.0 | 40.2 | 12 | 410.0 | 60.5 | 12 | 489.3 | 61.7 | 12 | 337.4 | 29.3 |
| C4       | ng/mL    | 12 | 75.3  | 5.1  | 12 | 48.7  | 11.6 | 12 | 52.0  | 10.2 | 12 | 33.2  | 4.0  |
| C5       | ng/mL    | 12 | 61.7  | 4.3  | 12 | 44.9  | 10.2 | 12 | 46.8  | 7.5  | 12 | 29.4  | 3.2  |
| C6       | ng/mL    | 12 | 48.2  | 3.6  | 12 | 41.1  | 10.0 | 12 | 41.6  | 5.2  | 12 | 25.6  | 2.6  |
| C7       | ng/mL    | 12 | 41.8  | 3.1  | 12 | 35.8  | 7.8  | 12 | 38.6  | 4.4  | 12 | 23.8  | 2.3  |
| C8       | ng/mL    | 12 | 35.4  | 2.7  | 12 | 30.6  | 5.7  | 12 | 35.6  | 3.7  | 12 | 22.1  | 2.2  |
| t1/2     | hr       | 12 | 8.8   | 0.7  | 11 | 11.4  | 1.5  | 10 | 9.7   | 0.8  | 10 | 10.1  | 0.9  |

FIG. 5 Continued

PHARMACEUTICAL COMPOSITIONS AND ORAL DOSAGE FORMS OF KETAMINE DERIVATIVES

This application claims the benefit under 35 U.S.C. § 119(e) of U.S. Provisional Application No. 63/232,717, filed on Aug. 13, 2021, which is incorporated by reference in its entirety.

FIELD

The invention relates to pharmaceutical compositions of a ketamine derivative and oral dosage forms comprising the pharmaceutical compositions. Solid oral dosage forms prepared from the pharmaceutical compositions exhibit a zero-order release profile in two-stage dissolution medium.

BACKGROUND

Ketamine derivatives that provide ketamine in the systemic circulation of a patient following oral administration are disclosed in U.S. Application Publication No. 2020/0231540 A1. Oral dosage forms containing the ketamine derivatives that provide a zero-order release profile in the gastrointestinal tract following ingestion are desired.

SUMMARY

According to the present invention, pharmaceutical compositions comprise:
(a) a compound of Formula (1):

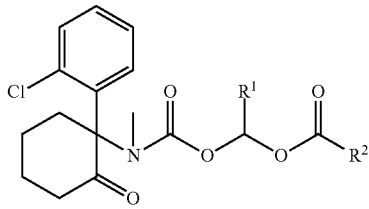

(1)

or a pharmaceutically acceptable salt thereof, wherein,
$R^1$ is selected from hydrogen and $C_{1-6}$ alkyl; and
$R^2$ is selected from a moiety of Formula (2), a moiety of Formula (3), a moiety of Formula (4), and a moiety of Formula (5):

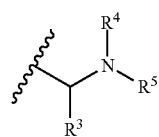

(2)

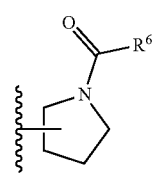

(3)

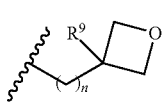

(4)

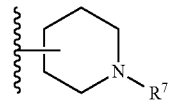

(5)

wherein,
$R^3$ is selected from hydrogen, $C_{1-6}$ alkyl, $C_{7-12}$ alkylarene, and substituted $C_{7-12}$ alkylarene;
$R^4$ is selected from hydrogen and $C_{1-6}$ alkyl;
$R^5$ is selected from hydrogen, $C_{1-6}$ alkyl, —C(=O)—$R^{10}$, and —C(=O)—O—$R^{10}$, wherein $R^{10}$ is selected from $C_{1-6}$ alkyl, $C_{3-6}$ cycloalkyl, and —$CF_3$;
$R^6$ is selected from $C_{1-6}$ alkyl and $C_{1-6}$ alkoxy;
n is an integer from 0 to 3;
$R^7$ is selected from hydrogen, $C_{1-6}$ alkyl, —C(=O)—$R^{11}$, and —C(=O)—O—$R^{10}$, wherein,
$R^{10}$ is selected from $C_{1-6}$ alkyl and $C_{3-6}$ cycloalkyl; and
$R^{11}$ is selected from —$NH_2$, —$CF_3$, $C_{1-6}$ alkyl, and $C_{3-6}$ cycloalkyl; and
$R^9$ is selected from hydrogen and $C_{1-3}$ alkyl;
(b) a controlled release polymer; and
(c) an anionic sulfate/sulfonate surfactant.

According to the present invention, oral dosage form prepared from the pharmaceutical composition of any one of aspects 1A to 41A.

According to the present invention, oral dosage forms comprise a pharmaceutical composition according to the present invention.

According to the present invention, kits comprise a pharmaceutical composition according to the present invention or an oral dosage form according to the present invention.

According to the present invention, methods of treating a disease in a patient comprise orally administering to a patient in need of such treatment a therapeutically effective amount of a pharmaceutical composition according to the present invention or an oral dosage form according to the present invention, wherein the disease is selected from a neurological disease, a psychiatric disease, and pain.

According to the present invention, method of treating a disease in a patient comprising orally administering to a patient in need of such treatment a therapeutically effective amount of a pharmaceutical composition according to the present invention or an oral dosage form according to the present invention, wherein the disease is treated by inhibiting NMDA receptors.

According to the present invention, a pharmaceutical composition according to the present invention can be used in the manufacture of a medicament for treating a disease in a patient, wherein the disease is selected from a neurological disease, a psychiatric disease, and pain.

According to the present invention, a pharmaceutical composition according to the present invention can be used in the manufacture of a medicament for treating a disease in a patient, wherein the disease is treated by inhibiting NMDA receptors.

BRIEF DESCRIPTION OF THE DRAWINGS

Those skilled in the art will understand that the drawings described herein are for illustration purposes only. The drawings are not intended to limit the scope of the present disclosure.

FIG. 5 is a table summarizing the esketamine and noresketamine pharmacokinetic parameters following oral administration of an immediate release tablet comprising 100 mg compound (39) and for the modified release tablets of FIGS. 4A-4B.

DETAILED DESCRIPTION

Figure 1:
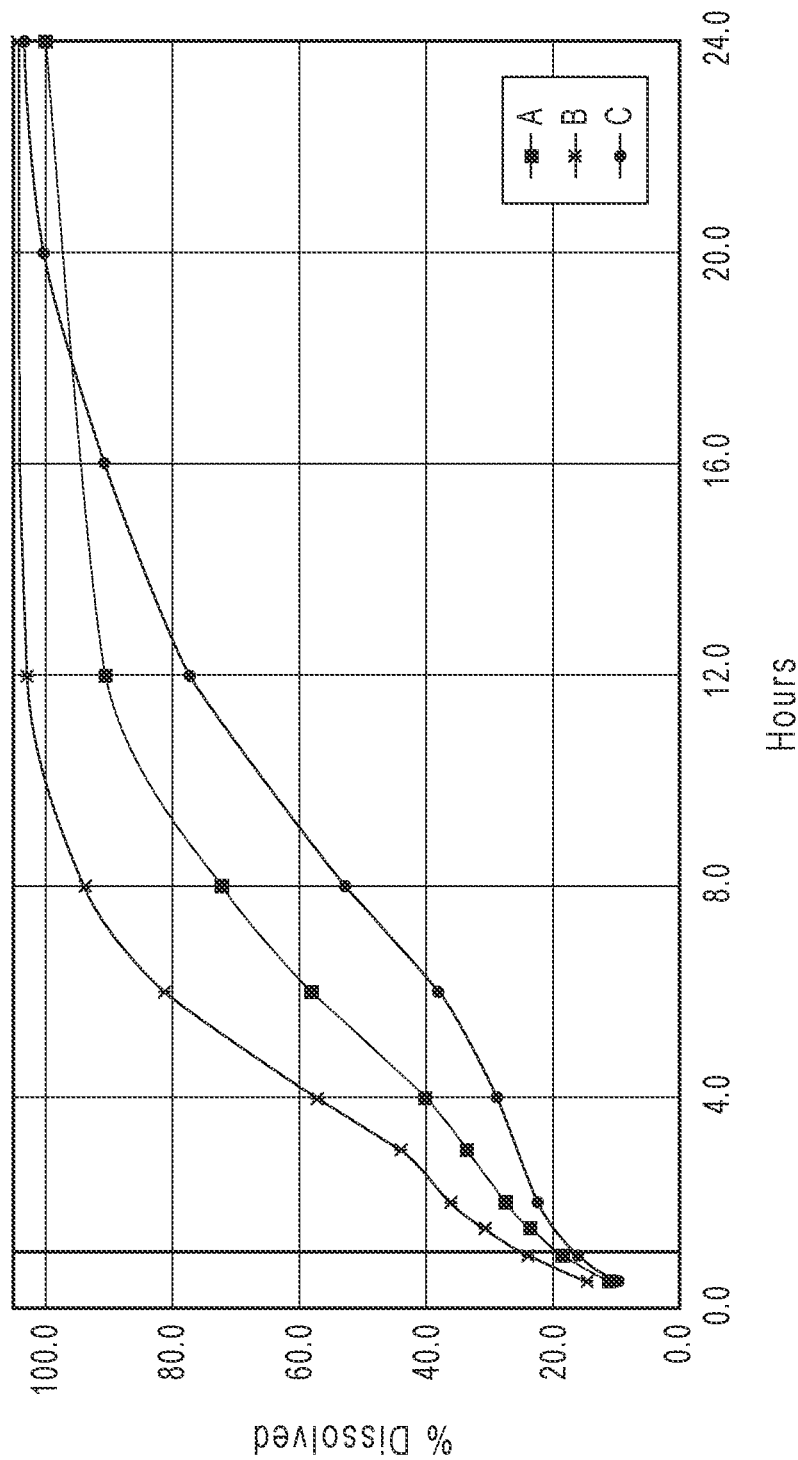
FIG. 1 shows dissolution profiles for examples of oral dosage forms provided by the present disclosure.

For purposes of the following detailed description, it is to be understood that embodiments provided by the present disclosure may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

"Controlled release" pharmaceutical compositions include modified release formulations, delayed release formulations, extended release, and sustained release formulation. These formulations are intended to release an API from the pharmaceutical composition at a desired rate and/or at a desired time following oral administration by a patient and/or at a certain location or locations with the gastrointestinal tract. The USP defines a modified release system as one in which the time course or location of drug release or both, are chosen to accomplish objectives of therapeutic effectiveness or convenience not fulfilled by conventional IR dosage forms. More specifically, MR solid oral dosage forms include extended release (ER) and delayed-release (DR) products. A DR product is one that releases a drug all at once at a time other than promptly after administration. A modified release formulation can include delayed-release using enteric coatings, site-specific or timed release such as for colonic delivery, extended-release including, for example, formulations capable of providing zero-order, first-order, or biphasic release profiles, and programmed release such as pulsatile and delayed extended release.

A dash ("-") that is not between two letters or symbols is used to indicate a point of attachment for a moiety or substituent. For example, —$CONH_2$ is attached through the carbon atom.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, and but-3-yn-1-yl. The term "alkyl" includes groups having any degree or level of saturation, i.e., groups having exclusively carbon-carbon single bonds, groups having one or more carbon-carbon double bonds, groups having one or more carbon-carbon triple bonds, and groups having combinations of carbon-carbon single, double, and triple bonds. Where a specific level of saturation is intended, the terms alkanyl, alkenyl, and alkynyl are used. An alkyl group can be, for example, $C_{1-6}$ alkyl, $C_{1-5}$ alkyl, $C_{1-4}$ alkyl, $C_{1-3}$ alkyl, ethyl or methyl.

"Alkoxy" refers to a radical —OR where R is alkyl as defined herein. Examples of alkoxy groups include methoxy, ethoxy, propoxy, and butoxy. An alkoxy group can be $C_{1-6}$ alkoxy, $C_{1-5}$ alkoxy, $C_{1-4}$ alkoxy, $C_{1-3}$ alkoxy, ethoxy or methoxy.

"Arylalkyl" refers to an acyclic alkyl radical in which one of the hydrogen atoms bonded to a carbon atom is replaced with an aryl group. Examples of arylalkyl groups include benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl. Where specific alkyl moieties are intended, the nomenclature arylalkanyl, arylalkenyl, or arylalkynyl is used. An arylalkyl group can be $C_{7-16}$ arylalkyl, e.g., the alkanyl, alkenyl or alkynyl moiety of the arylalkyl group is $C_{1-6}$ and the aryl moiety is $C_{6-10}$. An arylalkyl group can be $C_{7-16}$ arylalkyl, such as the alkanyl, alkenyl or alkynyl moiety of the arylalkyl group is $C_{1-6}$ and the aryl moiety is $C_{6-10}$. An arylalkyl group can be $C_{7-9}$ arylalkyl, wherein the alkyl moiety is $C_{1-3}$ alkyl, and the aryl moiety is phenyl. An arylalkyl group can be $C_{7-16}$ arylalkyl, $C_{7-14}$ arylalkyl, $C_{7-12}$ arylalkyl, $C_{7-10}$ arylalkyl, $C_{7-8}$ arylalkyl, or benzyl.

"Bioavailability" refers to the rate and amount of a drug that reaches the systemic circulation of a patient following administration of the drug or prodrug thereof to the patient and can be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or form of drug to the patient, and $T_{max}$ is the time to the maximum concentration ($C_{max}$) of a drug in the plasma or blood of a patient following administration of a dose of the drug or form of drug to the patient.

"Oral bioavailability" (F %) refers to the fraction of an oral administered drug that reaches systemic circulation. Oral bioavailability is a product of fraction absorbed, fraction escaping gut-wall elimination, and fraction escaping hepatic elimination; and the factors that influence bioavailability can be divided into physiological, physicochemical, and biopharmaceutical factors.

"Compounds" and moieties disclosed herein include any specific compounds within the disclosed formula. A compound may be identified either by chemical structure and/or by chemical name. Compounds are named using the ChemDraw® Ultra 17.1.0.105 (19) (CambridgeSoft, Cambridge, Mass.) nomenclature program. When the chemical structure and chemical name conflict, the chemical structure is determinative of the identity of the compound. The compounds described herein may comprise one or more stereogenic centers and/or double bonds and therefore may exist as stereoisomers such as double-bond isomers (i.e., geometric isomers), enantiomers, diastereomers, or atropisomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled in the art.

Compounds and moieties disclosed herein include optical isomers of compounds and moieties, racemates thereof, and other mixtures thereof. In such embodiments, the single enantiomers or diastereomers may be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column with chiral stationary phases. In addition, compounds include (Z)- and (E)-forms (or cis- and trans-forms) of compounds with double bonds either as single geometric isomers or mixtures thereof.

Compounds and moieties may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms. Certain compounds may exist in multiple crystalline, co-crystalline, or amorphous forms. Compounds include pharmaceutically acceptable salts thereof, or pharmaceutically acceptable solvates of the free acid form of any of the foregoing, as well as crystalline forms of any of the foregoing.

"Cycloalkyl" refers to a saturated or partially unsaturated cyclic alkyl radical. A cycloalkyl group can be $C_{3-6}$ cycloalkyl, $C_{3-5}$ cycloalkyl, $C_{5-6}$ cycloalkyl, cyclopropyl, cyclopentyl, or cyclohexyl. A cycloalkyl can be selected from cyclopropyl, cyclobutyl, cyclopentyl, and cyclohexyl.

"Disease" refers to a disease, disorder, condition, or symptom of any of the foregoing.

"Drug" as defined under 21 U.S.C. § 321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . . ".

"Ketamine equivalents" such as "mg ketamine equivalents" refers to the amount of ketamine in a ketamine prodrug provided by the present disclosure. The mg ketamine equivalents can be determined by multiplying the molecular weight of ketamine (237.7 g/mol) by the molecular weight of the ketamine prodrug to determine the fractional equivalents of ketamine in the corresponding ketamine prodrug and multiplying the amount of the ketamine prodrug by the fractional equivalents. For example, the ketamine prodrug 1-((((5)-1-(2-chlorophenyl)-2-oxocyclohexyl)(methyl)carbamoyl)oxy)ethyl acetylglycinate (3) has a molecular weight of 424.9 g/mol and the corresponding fractional equivalents of ketamine is 0.559 (237.7/424.9). Thus, 100 mg of 1-((((5)-1-(2-chlorophenyl)-2-oxocyclohexyl)(methyl)carbamoyl)oxy)ethyl acetylglycinate represents 55.9 mg equivalents of ketamine. Compound (39), ((((5)-1-(2-chlorophenyl)-2-oxocyclohexyl)(methyl)carbamoyl)oxy)methyl dimethyl-L-valinate, has a molecular weight of 438 g/mol and 100 mg of compound (39) represents 54.2 mg equivalents of ketamine.

"Ketamine" refers to (S)-ketamine, (R)-ketamine, and a racemic mixture thereof.

"Norketamine" is a major active metabolite of ketamine and has the structure:

"Norketamine" refers to the (S)-isomer, (noresketamine), the (R)-isomer, and a racemic mixture thereof.

"Hydrates" refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism.

"Immediate release" refers to a pharmaceutical composition that releases substantially all of a pharmaceutically active ingredient into the gastrointestinal tract of a patient within less than 1 hour following oral administration, such as within less than 50 minutes, within less than 40 minutes, within less than 30 minutes, within less than 20 minutes, or within less than 10 minutes following oral administration. For example, an immediate release dosage form can release greater than 90%, greater than 95%, or greater than 98% of the pharmaceutically active ingredient in the pharmaceutical composition into the gastrointestinal tract within less than 1 hour such as within less than 50 minutes, less than 40 minutes, less than 30 minutes, less than 20 minutes, or less than 10 minutes, following oral administration. Immediate release pharmaceutical compositions can be appropriate to administer pharmaceutically active ingredients that are absorbed into the systemic circulation from the upper portion of the gastrointestinal tract.

"Metabolic intermediate" refers to a compound that is formed in vivo by metabolism of a parent compound and that further undergoes reaction in vivo to release an active agent. Compounds of Formula (1) are acyloxyalkyl derivatives of ketamine that are metabolized in vivo to provide the corresponding metabolic intermediate. Metabolic intermediates undergo nucleophilic cyclization to release ketamine and one or more reaction products. It is desirable that the reaction products or metabolites thereof not be toxic.

A particle size distribution and mean particle diameter can be determined by laser diffraction or by sieve analysis.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable functional groups such as primary, secondary, or tertiary amines within the parent compound. Examples of suitable inorganic acids include hydrochloric acid, hydrobromic acid, sulfuric acid, nitric acid, and phosphoric acid. A salt can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid. A salt can be formed when one or more acidic protons present in the parent compound are replaced by a metal ion, e.g., an alkali metal ion, an alkaline earth ion, or an aluminum ion, or combinations thereof, or coordinates with an organic base such as ethanolamine, diethanolamine, triethanolamine, and N-methylglucamine. A pharmaceutically acceptable salt can be the hydrochloride salt. A pharmaceutically acceptable salt can be the sodium salt. In compounds having two or more ionizable groups, a pharmaceutically acceptable salt can comprise one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound of Formula (1) or a pharmaceutically acceptable salt thereof and at least one pharmaceutically acceptable vehicle, with which the compound of Formula (1) or a pharmaceutically acceptable salt thereof is administered to a patient. Pharmaceutically acceptable vehicles are known in the art.

"Population of fasted, healthy subjects" refers to two or more subject such as greater than 6 subjects.

"$C_{max}$" refers to the maximum concentration of an analyte.

"$C_t$" refers to the concentration of an analyte a time at t hours following administration. For example, $C_{4h}$ refers to the concentration of an analyte 4 hours following administration.

"$T_{max}$" refers to the time to reach $C_{max}$ following administration of a dose to a subject "AUC0-last" refers to the area under the concentration-time curve from the time of administration (0 time) to the last quantifiable concentration.

"$AUC_{0-inf}$" refers to the area under the concentration-time curve from the time of administration (0 time) extrapolated to infinity.

"$AUC_{0-t}$" refers to the area under the concentration-time curve from the time of administration to a time t following administration. For example, $AUC_{0-12h}$ refers to the area under the concentration-time curve from the time of administration to 12 hours following administration.

"$AUC_{t1-t2}$" refers to the area under the concentration-time curve during the time interval from t1 to t2. For example, $AUC_{2h-6h}$ refers to the area under the concentration-time curve from 2 hours to 6 hours following administration.

"$t_{1/2}$" refers to the apparent terminal half-life of the concentration-time curve.

A pharmacokinetic profile of a pharmaceutical formulation is considered to be bioequivalent to that of a reference pharmacokinetic profile if pharmacokinetic parameters of the pharmacokinetic profile for the pharmaceutical formulation including the $C_{max}$, $T_{max}$, $AUC_{0-8h}$ and $AUC_{0-inf}$ are within 80% to 125% of those of for the reference pharmacokinetic profile.

Two dissolution profiles are considered equivalent if the f2 similarity factor is greater than 50. Alternatively, dissolution profiles are equivalent if the difference at each sampling time point is 10% or less.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by administering a compound provided by the present disclosure in a preventative fashion. The application of a therapeutic agent for preventing or prevention of a disease of disorder is referred to as 'prophylaxis.' Compounds provided by the present disclosure can provide superior prophylaxis because of lower long-term side effects over long time periods.

"Prodrug" refers to a derivative of a drug molecule that requires a transformation within the body to release the active drug. Prodrugs are frequently, although not necessarily, pharmacologically inactive until converted to the parent drug. Prodrugs may be obtained by bonding a promoiety typically via a functional group, to a drug. For example, referring to compounds of Formula (1), an acyloxyalkyl promoiety bonded to the drug ketamine, via the amide group of ketamine. Compounds of Formula (1) are prodrugs of ketamine that can be metabolized within a patient's body to release ketamine.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond (s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation of a patient to which the prodrug is administered or the acidic conditions of the stomach or the agent may be supplied exogenously. Acyloxyalkyl derivatives provided by the present disclosure are prodrugs of ketamine. The acyloxyalkyl promoiety has the structure: For example, for a compound of Formula (1), an acyloxyalkyl promoiety has the structure:

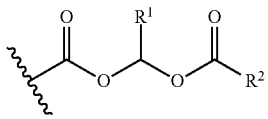

where $R^1$ and $R^2$ are defined as for Formula (1). The acyloxyalkyl promoiety is cleaved in the systemic circulation to release ketamine into the systemic circulation.

"Solvate" refers to a molecular complex of a compound with one or more solvent molecules in a stoichiometric or non-stoichiometric amount. Such solvent molecules are those commonly used in the pharmaceutical arts, which are known to be innocuous to a patient, such as water or ethanol. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water. Methods of making solvates include, for example, storage in an atmosphere containing a solvent, dosage forms that include the solvent, or routine pharmaceutical processing steps such as, for example, crystallization (i.e., from solvent or mixed solvents) vapor diffusion. Solvates may also be formed, under certain circumstances, from other crystalline solvates or hydrates upon exposure to the solvent or upon suspension material in solvent. Solvates may crystallize in more than one form resulting in solvate polymorphism.

"Substituted" refers to a group in which one or more hydrogen atoms are independently replaced with the same or different substituent(s). Each substituent can be independently selected from deuterio, halogen, —OH, —CN, —CF$_3$, —OCF$_3$, =O, —NO$_2$, $C_{1-6}$ alkoxy, $C_{1-6}$ alkyl, —COOR, —NR$_2$, and —CONR$_2$; wherein each R can be independently selected from hydrogen and $C_{1-6}$ alkyl. Each substituent can be independently selected from deuterio, halogen, —NH$_2$, —OH, $C_{1-3}$ alkoxy, and $C_{1-3}$ alkyl, trifluoromethoxy, and trifluoromethyl. Each substituent can be independently selected, for example, from deuterio, —OH, methyl, ethyl, trifluoromethyl, methoxy, ethoxy, and trifluoromethoxy. Each substituent can be selected, for example, from deuterio, $C_{1-3}$ alkyl, =O, $C_{1-3}$ alkyl, $C_{1-3}$ alkoxy, and phenyl. Each substituent can be selected, for example, from deuterio, —OH, —NH$_2$, $C_{1-3}$ alkyl, and $C_{1-3}$ alkoxy.

"Treating" or "treatment" of a disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter or manifestation that may or may not be discernible to the patient. "Treating" or "treatment" also refers to delaying the onset of the disease or delaying the onset of at least one or more symptoms thereof in a patient who may be exposed to or predisposed to a disease or disorder even though that patient does not yet experience or display symptoms of the disease.

"Therapeutically effective amount" refers to the amount of a compound that, when administered to a patient for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Vehicle" refers to a diluent, excipient or carrier with which a compound is administered to a patient. A vehicle can be a pharmaceutically acceptable vehicle. Pharmaceutically acceptable vehicles are known in the art.

Zero order drug release kinetics refers to the process of constant drug release from a dosage form. Constant release is defined as the same amount of drug release per unit time. For example, zero order drug release can be represented by the equation $C=C_0+k_0 \times t$, where C is the amount of drug released, $C_0$ is the initial amount of drug in solution, $k_0$ is the zero-order constant and t is time. Zero-order delivery systems have the potential to overcome issues associated with immediate-release and first-order systems by releasing drug at a constant rate, thereby facilitating maintaining drug concentrations within a therapeutic window for an extended period time. Zero order drug release kinetics can limit adverse side effects, reduce dosing frequency, and potentially improve patient compliance.

Reference is now made to certain pharmaceutical compositions, oral dosage forms, and methods. The disclosed embodiments are not intended to be limiting of the claims. To the contrary, the claims are intended to cover all alternatives, modifications, and equivalents.

A pharmaceutical composition provided by the present disclosure can comprise granules comprising a ketamine derivative or a pharmaceutically acceptable salt thereof, a controlled release polymer, and an anionic sulfate/sulfonate surfactant.

Solid oral dosage forms prepared from the pharmaceutical compositions exhibit a zero-order release profile in a simulated gastrointestinal environment. Including an anionic sulfate/sulfonate surfactant can increase the rate of dissolution of the ketamine derivative at high pH and reduce the dissolution rate at low pH.

Major Depressive Disorder (MDD) is one of the most common mental disorders, affecting 264 million people worldwide. Depression greatly increases the risk of suicide, which is the second leading cause of death among adolescents and young adults. Even though MDD is a common illness, its pathophysiology is complex. An accepted cause underlying MDD is based on the monoamine hypothesis, which proposes that depressed patients have decreased concentrations of monoamines, such as serotonin, noradrenaline, and dopamine, in the synaptic gaps. This paradigm has guided the development of new drug therapies for depression and the development monoamine-based pharmacological drug classes including tricyclic antidepressants (TCA), selective serotonin reuptake inhibitors (SSRIs) and serotonin-norepinephrine reuptake inhibitors (SNRIs) among others and continue to represent the standard of care. However, approximately one-third of the MDD patients do not respond to current antidepressant treatments and are considered to have treatment-resistant depression (TRD).

Ketamine and esketamine have been shown to be effective in treating major depressive disorder. Ketamine and esketamine have demonstrated rapid-onset of antidepressant effects in patients with treatment-resistant depression. These studies utilized intravenous ketamine and intranasal esketamine which was approved in 2021 as SPRAVATO® for use in Australia. These benefits are accompanied by acute, transient (approximately 2 hours) side effects of dissociation, sedation, and increased blood pressure which are associated with peak plasma concentrations of ketamine and esketamine. Because ketamine and esketamine have high first-pass enterohepatic metabolism these drugs are typically administered by rapid (40 minute) intravenous and intranasal routes of administration. In addition, the metabolites noresketamine/noresketamine and their hydroxyl metabolites are thought to have important roles in ketamine/esketamine antidepressant actions.

Orally administered forms of esketamine in a modified release tablet formulation can improve safety and tolerability of ketamine therapy while maintaining the antidepressant actions. Controlled release of esketamine will also slow absorption and clearance of the drug.

Ketamine prodrugs provided by the present disclosure are esketamine/promoiety conjugates designed for oral absorption, improved bioavailability, and formulation into a modified release tablet capable of release the ketamine prodrug without producing a high Cmax and releasing the drug over a duration of approximately 12 hours.

Ketamine is currently used for the treatment of acute pain, chronic pain, major depression, bipolar disorder and suicidal behavior, and as an anti-inflammatory agent. Ketamine has poor oral bioavailability. Ketamine derivatives provided by the present disclosure are acyloxyalkyl prodrugs of ketamine. The ketamine acyloxyalkyl prodrugs exhibit enhanced ketamine oral bioavailability compared to ketamine. In the ketamine prodrugs a promoiety is bonded to the amide group. In the systemic circulation of a patient, the acyloxyalkyl promoiety is cleaved to release ketamine in the systemic circulation. Ketamine, 2-(2-chlorophenyl)-2-(methylamino)cyclohexan-1-one, has the structure:

and both the (S)- and (R)-isomers are pharmacologically active. (S)-ketamine and (R)-ketamine have the structures:

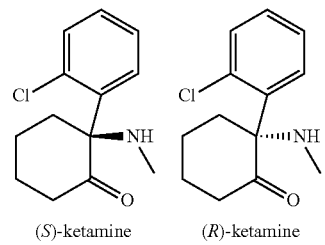

(S)-ketamine      (R)-ketamine

Ketamine has an oral bioavailability in humans of about 20% (% F). Ketamine derivatives provided by the present disclosure exhibit an oral bioavailability (% F) of ketamine greater than that of orally administered ketamine and exhibit an improved pharmacokinetic profile. The ketamine prodrugs can be used in controlled and modified release oral dosage forms.

Following oral administration, the ketamine derivatives can provide a therapeutically effective amount of ketamine in the systemic circulation of a patient. Metabolites of ketamine such as, for example, (S)-norketamine (noresketamine), (R)-norketamine (norketamine), (2S,6S)-hydroxynorketamine, and (2R,6R)-hydroxynorketamine are considered to be therapeutically effective for treating certain diseases.

Compounds provided by the present disclosure are prodrugs of ketamine. For example, compound (39), ((((S)-1-(2-chlorophenyl)-2-oxocyclohexyl)(methyl)carbamoyl)oxy)methyl dimethyl-L-valinate, comprises esketamine conjugated to N,N-dimethyl-L-valine (DMV) to form a prodrug that releases esketamine, an N-methyl-D-aspartate-receptor (NMDA-receptor) antagonist and α-amino-3-hydroxy-5-methyl-4-isoxazolepropionic acid (AMPA) receptor activator in the systemic circulation. From preclinical studies it appears that compound (39) is metabolized by CYP2D6, CYP2C19 and CYP3A4 to release esketamine. Compound (1) is being developed for the treatment of major depressive disorder and chronic pain. Following oral administration, compound (39) is cleaved into 1 molar equivalent of esketamine, the active moiety, and DMV.

Compound (39) and other ketamine prodrugs provided by the present disclosure can be formulated into a modified release oral tablet to obviate concentration-related side effects of dissociation, sedation and elevated blood pressure by lowering the Cmax compared to intranasal SPRAVATO® and intravenously administered ketamine while delivering esketamine doses similar to or greater than those known to be exhibit antidepressant effects.

In preclinical pharmacokinetic studies, compound (39) exhibited rapid absorption and conversion to esketamine in mice, rats, dogs and monkeys. The systemic exposure, expressed as AUC, ranged from being less than to greater than dose proportional for compound (39), esketamine, and noresketamine. The preclinical pharmacokinetics of compound (39) suggests the drug will be absorbed orally and rapidly release esketamine. Accumulation of compound (39) and its metabolites were not observed following repeated dosing.

A ketamine derivative can have the structure of Formula (1):

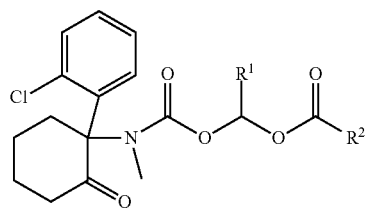
(1)

or a pharmaceutically acceptable salt thereof, wherein,
R$^1$ can be selected from hydrogen and C$_{1-6}$ alkyl; and
R$^2$ can be selected from a moiety of Formula (2), a moiety of Formula (3), a moiety of Formula (4), and a moiety of Formula (5):

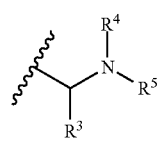
(2)

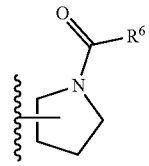
(3)

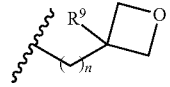
(4)

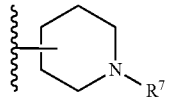
(5)

wherein,
R$^3$ can be selected from hydrogen, C$_{1-6}$ alkyl, and C$_{7-12}$ arylalkyl;
R$^4$ can be selected from hydrogen and C$_{1-6}$ alkyl;
R$^5$ can be selected from hydrogen, C$_{1-6}$ alkyl, —C(=O)—R$^{10}$, and —C(=O)—O—R$^{10}$, wherein R$^{10}$ can be selected from C$_{1-6}$ alkyl and C$_{3-6}$ cycloalkyl;
R$^6$ can be selected from C$_{1-6}$ alkyl, C$_{1-6}$ alkoxy, and —CF$_3$;
n can be an integer from 0 to 3;
R$^7$ is selected from hydrogen, C$_{1-6}$ alkyl, —C(=O)—R$^{11}$, and —C(=O)—O—R$^{10}$,
wherein,
R$^{10}$ is selected from C$_{1-6}$ alkyl and C$_{3-6}$ cycloalkyl; and
R$^{11}$ is selected from —NH$_2$, —CF$_3$, C$_{1-6}$ alkyl, and C$_{3-6}$ cycloalkyl; and
R$^9$ is selected from hydrogen and C$_{1-3}$ alkyl.

In a compound of Formula (1), the carbon atom to which R$^1$ is bonded can be in the (S) configuration.

In a compound of Formula (1), the carbon atom to which R$^1$ is bonded can be in the (R) configuration.

In a compound of Formula (1), R$^1$ can be hydrogen.

In a compound of Formula (1), R$^1$ can be selected from methyl, ethyl, n-propyl and iso-propyl.

In a compound of Formula (1), R$^2$ can be a moiety having the structure of Formula (2).

In a moiety of Formula (2), R$^3$ can be hydrogen.

In a moiety of Formula (2), R$^3$ can be C$_{1-6}$ alkyl.

In a moiety of Formula (2), R$^3$ can be selected from methyl, ethyl, n-propyl, isopropyl, isobutyl, and 2-methylpropyl.

In a moiety of Formula (2), R$^3$ can be C$_{7-12}$ arylalkyl.

In a moiety of Formula (2), R$^3$ can be selected from benzyl and phenethyl.

In a moiety of Formula (2), the carbon atom to which R$^3$ is bonded can be in the (S) configuration.

In a moiety of Formula (2), the carbon atom to which R$^3$ is bonded can be in the (R) configuration.

In a moiety of Formula (2), R$^4$ can be hydrogen.

In a moiety of Formula (2), R$^4$ can be C$_{1-6}$ alkyl.

In a moiety of Formula (2), R$^4$ can be selected from methyl, ethyl, n-propyl, and isopropyl.

In a moiety of Formula (2), R$^5$ can be C$_{1-6}$ alkyl.

In a moiety of Formula (2), R$^5$ can be selected from methyl, ethyl, n-propyl, and isopropyl.

In a moiety of Formula (2), R$^5$ can be hydrogen.

In a moiety of Formula (2), $R^5$ can be —C(=O)—$R^{10}$, and $R^{10}$ can be selected from $C_{1-6}$ alkyl and $C_{3-6}$ cycloalkyl.

In a moiety of Formula (2), $R^5$ can be —C(=O)—$R^{10}$, and $R^{10}$ can be —$CF_3$.

In a moiety of Formula (2), $R^5$ can be —C(=O)—$R^{10}$, and $R^{10}$ can be $C_{1-6}$ alkyl.

In a moiety of Formula (2), $R^5$ can be —C(=O)—$R^{10}$, and $R^{10}$ can be selected from methyl, ethyl, n-propyl, and isopropyl.

In a moiety of Formula (2), $R^5$ can be —C(=O)—$R^{10}$, and $R^{10}$ can be $C_{3-6}$ cycloalkyl.

In a moiety of Formula (2), $R^5$ can be —C(=O)—$R^{10}$, and $R^{10}$ can be selected from $C_{1-6}$ alkyl and $C_{3-6}$ cycloalkyl.

In a moiety of Formula (2), $R^5$ can be —C(=O)—O—$R^{10}$, and $R^{10}$ can be $C_{1-6}$ alkyl.

In a moiety of Formula (2), $R^5$ can be —C(=O)—O—$R^{10}$, and $R^{10}$ can be selected from methyl, ethyl, n-propyl, and isopropyl.

In a moiety of Formula (2), $R^5$ can be —C(=O)—O—$R^{10}$, and $R^{10}$ can be $C_{3-6}$ cycloalkyl.

In a moiety of Formula (2), $R^5$ can be —C(=O)—O—$R^{10}$, and $R^{10}$ can be —$CF_3$.

In a moiety of Formula (2), $R^4$ can be hydrogen and R can be $C_{1-6}$ alkyl.

In a moiety of Formula (2), $R^4$ can be $C_{1-6}$ alkyl and $R^5$ can be $C_{1-6}$ alkyl.

In a moiety of Formula (2), $R^4$ can be hydrogen and R can be —C(=O)—$R^{10}$.

In a moiety of Formula (2), $R^4$ can be $C_{1-6}$ alkyl and $R^5$ can be —C(=O)—$R^{10}$.

In a moiety of Formula (2), $R^4$ can be hydrogen and R can be —C(=O)—O—$R^{10}$.

In a moiety of Formula (2), $R^4$ can be $C_{1-6}$ alkyl and $R^5$ can be —C(=O)—O—$R^{10}$.

In a compound of Formula (1), $R^2$ can be a moiety having the structure of Formula (3).

In a moiety of Formula (3), $R^6$ can be $C_{1-6}$ alkyl.

In a moiety of Formula (3), $R^6$ can be selected from methyl, ethyl, n-propyl, and isopropyl.

In a moiety of Formula (3), $R^6$ can be $C_{1-6}$ alkoxy.

In a moiety of Formula (3), $R^6$ can be selected from methoxy, ethoxy, n-propoxy, and isopropoxy.

In a compound of Formula (1), $R^2$ can be a moiety having the structure of Formula (4).

In a moiety of Formula (4), n can be 0, 1, 2, or 3.

In a moiety of Formula (4), n can be 0.

In a moiety of Formula (4), n can be 1.

In a moiety of Formula (4), $R^9$ can be hydrogen.

In a moiety of Formula (4), $R^9$ can be selected from methyl, ethyl, n-propyl, and isopropyl.

In a compound of Formula (1), $R^2$ can be a moiety having the structure of Formula (5).

In a moiety of Formula (5), $R^2$ can be piperidin-2-yl, piperidine-3-yl, and piperidin-4-yl.

In a moiety of Formula (5), $R^7$ can be hydrogen.

In a moiety of Formula (5), $R^7$ can be $C_{1-6}$ alkyl.

In a moiety of Formula (5), $R^7$ can be —C(=O)—$R^{11}$, and $R^{11}$ can be selected from —$NH_2$, $C_{1-6}$ alkyl, and $C_{3-6}$ cycloalkyl.

In a moiety of Formula (5), $R^7$ can be —C(=O)—$R^{11}$, and $R^{11}$ can be —$NH_2$.

In a moiety of Formula (5), $R^7$ can be —C(=O)—$R^{11}$, and $R^{11}$ can be $C_{1-6}$ alkyl.

In a moiety of Formula (5), $R^7$ can be —C(=O)—$R^{11}$, and $R^{11}$ can be selected from methyl, ethyl, n-propyl, and isopropyl.

In a moiety of Formula (5), $R^7$ can be —C(=O)—$R^{11}$, and $R^{11}$ can be $C_{3-6}$ cycloalkyl.

In a moiety of Formula (5), $R^7$ can be —C(=O)—O—$R^{10}$, and $R^{10}$ can be selected from $C_{1-6}$ alkyl and $C_{3-6}$ cycloalkyl.

In a moiety of Formula (5), $R^7$ can be —C(=O)—O—$R^{10}$, and $R^{10}$ can be $C_{1-6}$ alkyl.

In a moiety of Formula (5), $R^7$ can be —C(=O)—O—$R^{10}$, and $R^{10}$ can be selected from methyl, ethyl, n-propyl, and isopropyl.

In a moiety of Formula (5), $R^7$ can be —C(=O)—O—$R^{10}$, and $R^{10}$ can be $C_{3-6}$ cycloalkyl.

A compound of Formula (1) can be the (R) isomer and can have the structure of Formula (1a):

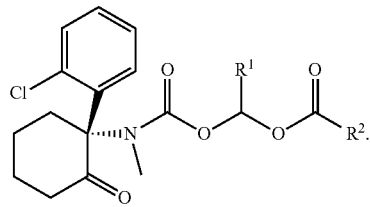

(1a)

A compound of Formula (1) can be the (S) isomer and can have the structure of Formula (1b):

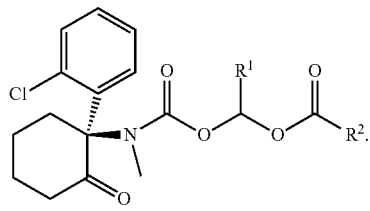

(1b)

A compound of Formula (1), a compound of Formula (1a), and a compound of Formula (1b) can be the free base.

A compound of Formula (1), a compound of Formula (1a), and a compound of Formula (1b) can be a pharmaceutically acceptable salt. For example, a compound of Formula (1), a compound of Formula (1a), and a compound of Formula (1b), can be the hydrochloride salt.

A compound of Formula (1) can be a pharmaceutically acceptable salt of a compound of Formula (1), a hydrate thereof, or a solvate of any of the foregoing.

A compound of Formula (1) can be selected from:
1-((((S)-1-(2-chlorophenyl)-2-oxocyclohexyl)(methyl)carbamoyl)oxy)ethyl acetylglycinate (3);
1-((((S)-1-(2-chlorophenyl)-2-oxocyclohexyl)(methyl)carbamoyl)oxy)ethyl (tert-butoxycarbonyl)glycinate (4);
1-((((S)-1-(2-chlorophenyl)-2-oxocyclohexyl)(methyl)carbamoyl)oxy)ethyl (tert-butoxycarbonyl)-L-valinate (5);
1-((((S)-1-(2-chlorophenyl)-2-oxocyclohexyl)(methyl)carbamoyl)oxy)ethyl 2-(3-methyloxetan-3-yl)acetate (6);
1-((((S)-1-(2-chlorophenyl)-2-oxocyclohexyl)(methyl)carbamoyl)oxy)ethyl acetyl-L-alaninate (7);
1-((((S)-1-(2-chlorophenyl)-2-oxocyclohexyl)(methyl)carbamoyl)oxy)ethyl acetyl-L-valinate (8);
1-((((S)-1-(2-chlorophenyl)-2-oxocyclohexyl)(methyl)carbamoyl)oxy)ethyl-1-methylpiperidine-4-carboxylate (17);

1-(2-(isobutyramido)acetoyloxy)ethyl (S)-1-(2-chlorophenyl)-2-oxocyclohexylmethylcarbamate (19);
(2-(3-methyloxetan-3-yl)acetoyloxy)methyl (S)-1-(2-chlorophenyl)-2-oxocyclohexylmethylcarbamate (22);
1-((((S)-1-(2-chlorophenyl)-2-oxocyclohexyl)(methyl)carbamoyl)oxy)propyl 2-(3-methyloxetan-3-yl)acetate (24);
1-(2-(3-methyloxetan-3-yl)acetoyloxy)-2-methylpropyl (S)-1-(2-chlorophenyl)-2-oxocyclohexylmethylcarbamate (26);
1-((((S)-1-(2-chlorophenyl)-2-oxocyclohexyl)(methyl)carbamoyl)oxy)propyl acetylglycinate (27); 1-(2-acetamidoacetoyloxy)-2-methylpropyl (S)-1-(2-chlorophenyl)-2-oxocyclohexylmethylcarbamate (28);
(2-acetamidoacetoyloxy)methyl (S)-1-(2-chlorophenyl)-2-oxocyclohexylmethylcarbamate (31);
((S)-2-acetamido-3-methylbutanoyloxy)methyl (S)-1-(2-chlorophenyl)-2-oxocyclohexylmethylcarbamate (32);
((S)-2-acetamidopropanoyloxy)methyl (S)-1-(2-chlorophenyl)-2-oxocyclohexylmethylcarbamate (33);
(2-(isobutyramido)acetoyloxy)methyl (S)-1-(2-chlorophenyl)-2-oxocyclohexylmethylcarbamate (34);
((S)-2-(isobutyramido)propanoyloxy)methyl (S)-1-(2-chlorophenyl)-2-oxocyclohexylmethylcarbamate (35);
((S)-2-(isobutyramido)-3-methylbutanoyloxy)methyl (S)-1-(2-chlorophenyl)-2-oxocyclohexylmethylcarbamate (36);
((((S)-1-(2-chlorophenyl)-2-oxocyclohexyl)(methyl)carbamoyl)oxy)methyl L-valinate (37);
(S)-(((1-(2-chlorophenyl)-2-oxocyclohexyl)(methyl)carbamoyl)oxy)methyl glycinate (38);
((((S)-1-(2-chlorophenyl)-2-oxocyclohexyl)(methyl)carbamoyl)oxy)methyl dimethyl-L-valinate (39);
(2-(N-methylacetamido)acetoyloxy)methyl (S)-1-(2-chlorophenyl)-2-oxocyclohexylmethylcarbamate (40);
1-(2-(N-methylacetamido)acetoyloxy)ethyl (S)-1-(2-chlorophenyl)-2-oxocyclohexylmethylcarbamate (41);
1-(2-(propionamido)acetoyloxy)ethyl (S)-1-(2-chlorophenyl)-2-oxocyclohexylmethylcarbamate (42);
(2-(propionamido)acetoyloxy)methyl (S)-1-(2-chlorophenyl)-2-oxocyclohexylmethylcarbamate (43);
((((S)-1-(2-chlorophenyl)-2-oxocyclohexyl)(methyl)carbamoyl)oxy)methyl L-alaninate (44);
1-(2-(propionamido)acetoyloxy)ethyl (S)-1-(2-chlorophenyl)-2-oxocyclohexylmethylcarbamate (45);
(2-(2,2,2-trifluoroacetamido)acetoyloxy)methyl (S)-1-(2-chlorophenyl)-2-oxocyclohexylmethylcarbamate (46);
1-((((S)-1-(2-chlorophenyl)-2-oxocyclohexyl)(methyl)carbamoyl)oxy)ethyl dimethyl-L-alaninate (47);
((S)-2-(2,2,2-trifluoroacetamido)-3-methylbutanoyloxy)methyl (S)-1-(2-chlorophenyl)-2-oxocyclohexylmethylcarbamate (48);
1-(2-(2,2,2-trifluoroacetamido)acetoyloxy)propyl (S)-1-(2-chlorophenyl)-2-oxocyclohexylmethylcarbamate (49);
((S)-2-(2,2,2-trifluoroacetamido)propanoyloxy)methyl (S)-1-(2-chlorophenyl)-2-oxocyclohexylmethylcarbamate (50);
1-(2-(2,2,2-trifluoroacetamido)acetoyloxy)-2-methylpropyl (S)-1-(2-chlorophenyl)-2-oxocyclohexylmethylcarbamate (51);
1-((S)-2-(2,2,2-trifluoroacetamido)-3-methylbutanoyloxy)ethyl (S)-1-(2-chlorophenyl)-2-oxocyclohexylmethylcarbamate (52);
1-((S)-2-(2,2,2-trifluoroacetamido)propanoyloxy)ethyl (S)-1-(2-chlorophenyl)-2-oxocyclohexylmethylcarbamate (53);
1-((S)-2-acetamido-4-methylpentanoyloxy)ethyl (S)-1-(2-chlorophenyl)-2-oxocyclohexylmethylcarbamate (57);
((S)-2-acetamido-4-methylpentanoyloxy)methyl (S)-1-(2-chlorophenyl)-2-oxocyclohexylmethylcarbamate (58);
1-(((((S)-1-(2-chlorophenyl)-2-oxocyclohexyl)(methyl)carbamoyl)oxy)ethyl 2-(3-methyloxetan-3-yl)acetate (59);
((2S,3R)-2-acetamido-3-methylpentanoyloxy)methyl (S)-1-(2-chlorophenyl)-2-oxocyclohexylmethylcarbamate (60);
1-(2-acetamidoacetoyloxy)ethyl (R)-1-(2-chlorophenyl)-2-oxocyclohexyl-methylcarbamate (62);
1-(2-(3-methyloxetan-3-yl)acetoyloxy)ethyl (R)-1-(2-chlorophenyl)-2-oxocyclohexylmethylcarbamate (63);
1-((S)-2-acetamidopropanoyloxy)ethyl (S)-1-(2-chlorophenyl)-2-oxocyclohexylmethylcarbamate (64);
1-((S)-2-acetamido-3-methylbutanoyloxy)ethyl (R)-1-(2-chlorophenyl)-2-oxocyclohexylmethylcarbamate (65);
(2-(3-methyloxetan-3-yl)acetoyloxy)methyl (R)-1-(2-chlorophenyl)-2-oxocyclohexylmethylcarbamate (66);
(2-acetamidoacetoyloxy)methyl 1-(2-chlorophenyl)-2-oxocyclohexyl-methylcarbamate (68);
((S)-2-acetamido-3-methylbutanoyloxy)methyl 1-(2-chlorophenyl)-2-oxocyclohexylmethylcarbamate (69);
((S)-2-acetamidopropanoyloxy)methyl (S)-1-(2-chlorophenyl)-2-oxocyclohexylmethylcarbamate (70);
((S)-2-acetamido-4-methylpentanoyloxy)methyl (R)-1-(2-chlorophenyl)-2-oxocyclohexylmethylcarbamate (71);
((2S,3R)-2-acetamido-3-methylpentanoyloxy)methyl 1-(2-chlorophenyl)-2-oxocyclohexylmethylcarbamate (72);
((((S)-1-(2-chlorophenyl)-2-oxocyclohexyl)(methyl)carbamoyl)oxy)methyl dimethyl-L-lloisoleucinate hydrogen chloride (74);
((((S)-1-(2-chlorophenyl)-2-oxocyclohexyl)(methyl)carbamoyl)oxy)methyl methyl-L-valinate hydrogen chloride (75);
((((S)-1-(2-chlorophenyl)-2-oxocyclohexyl)(methyl)carbamoyl)oxy)methyl dimethyl-L-leucinate hydrogen chloride (76);
((((S)-1-(2-chlorophenyl)-2-oxocyclohexyl)(methyl)carbamoyl)oxy)methyl diethyl-L-valinate hydrogen chloride (77);
((((S)-1-(2-chlorophenyl)-2-oxocyclohexyl)(methyl)carbamoyl)oxy)methyl methyl-L-alaninate 2,2,2-trifluoroacetic acid (78);
((((S)-1-(2-chlorophenyl)-2-oxocyclohexyl)(methyl)carbamoyl)oxy)methyl dipropyl-L-valinate (79);
((((S)-1-(2-chlorophenyl)-2-oxocyclohexyl)(methyl)carbamoyl)oxy)methyl L-leucinate hydrogen chloride (80);
((((S)-1-(2-chlorophenyl)-2-oxocyclohexyl)(methyl)carbamoyl)oxy)methyl isopropyl-L-valinate hydrogen chloride (81);
((((S)-1-(2-chlorophenyl)-2-oxocyclohexyl)(methyl)carbamoyl)oxy)methyl propyl-L-valinate hydrogen chloride (82);
((((S)-1-(2-chlorophenyl)-2-oxocyclohexyl)(methyl)carbamoyl)oxy)methyl ethyl-L-valinate (83);
(piperidine-4-carboxyloyloxy)methyl (S)-1-(2-chlorophenyl)-2-oxocyclohexylmethylcarbamate (86);
((((S)-1-(2-chlorophenyl)-2-oxocyclohexyl)(methyl)carbamoyl)oxy)methyl acetyl-D-prolinate (87);
((((S)-1-(2-chlorophenyl)-2-oxocyclohexyl)(methyl)carbamoyl)oxy)methyl acetyl-L-phenylalaninate (88) ((((S)-1-(2-chlorophenyl)-2-oxocyclohexyl)(methyl)carbamoyl)oxy)methyl acetyl-L-tyrosinate (89);
1-(((((S)-1-(2-chlorophenyl)-2-oxocyclohexyl)(methyl)carbamoyl)oxy)ethyl dimethyl-L-valinate (90); and
a pharmaceutically acceptable salt of any of the foregoing.

A compound of Formula (1) can be 1-((((S)-1-(2-chlorophenyl)-2-oxocyclohexyl)(methyl)carbamoyl)oxy)ethyl 2-aminonicotinate.

A compound of Formula (1) can be selected from:
1-((((S)-1-(2-chlorophenyl)-2-oxocyclohexyl)(methyl)carbamoyl)oxy)ethyl acetylglycinate (3);
1-((((S)-1-(2-chlorophenyl)-2-oxocyclohexyl)(methyl)carbamoyl)oxy)ethyl 2-(3-methyloxetan-3-yl)acetate (6);
1-((((S)-1-(2-chlorophenyl)-2-oxocyclohexyl)(methyl)carbamoyl)oxy)ethyl acetyl-L-alaninate (7);
1-(isonicotinoyloxy)ethyl (S)-1-(2-chlorophenyl)-2-oxocyclohexylmethylcarbamate (18);
1-(2-(isobutyramido)acetoyloxy)ethyl (S)-1-(2-chlorophenyl)-2-oxocyclohexylmethylcarbamate (19);
(2-(3-methyloxetan-3-yl)acetoyloxy)methyl (S)-1-(2-chlorophenyl)-2-oxocyclohexylmethylcarbamate (22);
1-((((S)-1-(2-chlorophenyl)-2-oxocyclohexyl)(methyl)carbamoyl)oxy)propyl acetylglycinate (27);
1-(2-acetamidoacetoyloxy)-2-methylpropyl (S)-1-(2-chlorophenyl)-2-oxocyclohexylmethylcarbamate (28);
((((S)-1-(2-chlorophenyl)-2-oxocyclohexyl)(methyl)carbamoyl)oxy)methyl dimethyl-L-valinate (39);
((2S,3R)-2-acetamido-3-methylpentanoyloxy)methyl (S)-1-(2-chlorophenyl)-2-oxocyclohexylmethylcarbamate (60); and
a pharmaceutically acceptable salt of any of the foregoing.

A compound provided by the present disclosure can have the structure of Formula (1):

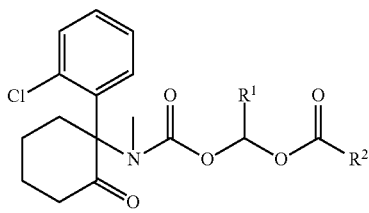

(1)

or a pharmaceutically acceptable salt thereof, wherein,
$R^1$ can be selected from hydrogen and $C_{1-6}$ alkyl; and
$R^2$ can be selected from a moiety of Formula (6):

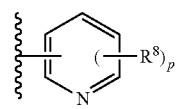

(6)

wherein,
p is an integer from 1 to 3; and
each $R^8$ is independently selected from hydrogen, $C_{1-6}$ alkyl, and $-NH_2$.

In a compound of Formula (1) in which $R^2$ is a moiety of Formula (6), the carbon atom to which $R^1$ is bonded can be in the (S) configuration.

In a compound of Formula (1) in which $R^2$ is a moiety of Formula (6), the carbon atom to which $R^1$ is bonded can be in the (R) configuration.

In a compound of Formula (1) in which $R^2$ is a moiety of Formula (6), $R^1$ can be hydrogen.

In a compound of Formula (1) in which $R^2$ is a moiety of Formula (6), $R^1$ can be $C_{1-6}$ alkyl.

In a compound of Formula (1) in which $R^2$ is a moiety of Formula (6), $R^1$ can be selected from methyl, ethyl, propyl, and isopropyl.

In a moiety of Formula (6), p can be 1.
In a moiety of Formula (6), p can be 2.
In a moiety of Formula (6), p can be 3.
In a moiety of Formula (6), each $R^8$ can be hydrogen.
In a moiety of Formula (6), each $R^8$ can independently be $C_{1-6}$ alkyl.
In a moiety of Formula (6), each $R^8$ can independently be selected from methyl, ethyl, propyl, and isopropyl.
In a moiety of Formula (6), each $R^8$ can independently be $-NH_2$.

In a compound of Formula (1), in which $R^2$ is a moiety of Formula (6), the compound can be selected from:
1-((((S)-1-(2-chlorophenyl)-2-oxocyclohexyl)(methyl)carbamoyl)oxy)ethyl nicotinate (14);
1-(isonicotinoyloxy)ethyl (S)-1-(2-chlorophenyl)-2-oxocyclohexylmethylcarbamate (18); (nicotinoyloxy)methyl (S)-1-(2-chlorophenyl)-2-oxocyclohexylmethylcarbamate (29);
(4-methylpyridine-3-carboxyloyloxy)methyl (S)-1-(2-chlorophenyl)-2-oxocyclohexylmethylcarbamate (54);
(2-methylpyridine-3-carboxyloyloxy)methyl (S)-1-(2-chlorophenyl)-2-oxocyclohexylmethylcarbamate (55);
(6-methylpyridine-3-carboxyloyloxy)methyl (S)-1-(2-chlorophenyl)-2-oxocyclohexylmethylcarbamate (56);
(S)-(((1-(2-chlorophenyl)-2-oxocyclohexyl)(methyl)carbamoyl)oxy)methyl 2-aminonicotinate (61); (nicotinoyloxy)methyl (R)-1-(2-chlorophenyl)-2-oxocyclohexylmethylcarbamate (67);
(R)-(((1-(2-chlorophenyl)-2-oxocyclohexyl)(methyl)carbamoyl)oxy)methyl 2-aminonicotinate (73); and
a pharmaceutically acceptable salt of any of the foregoing.

In a compound of Formula (1) in which $R^2$ is a moiety of Formula (6) the compound can be the (R)-isomer having the structure of Formula (1a):

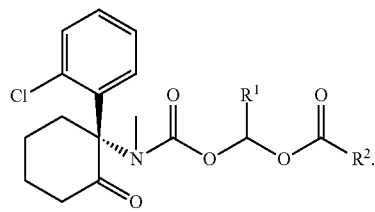

(1a)

In a compound of Formula (1) in which $R^2$ is a moiety of Formula (6) the compound can be the (S)-isomer having the structure of Formula (1b):

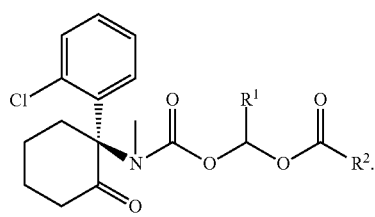

(1b)

In a compound of Formula (1) in which $R^2$ is a moiety of Formula (6) the compound can comprise the hydrochloride salt.

A compound of Formula (1) can have the structure of subgenus (2A), wherein, $R^1$ can be selected from hydrogen and methyl;
$R^2$ can be a moiety of Formula (2);
$R^3$ can be selected from hydrogen and $C_{1-4}$ alkyl;
$R^4$ can be selected from hydrogen and $C_{1-3}$ alkyl; and
$R^5$ can be selected from $C_{1-3}$ alkyl and —C(=O)—$R^{10}$, where $R^{10}$ can be selected from $C_{1-3}$ alkyl.

In a compound of subgenus (2A), $R^1$ can be hydrogen.
In a compound of subgenus (2A), $R^1$ can be methyl.
In a compound of subgenus (2A), the carbon atom to which $R^1$ is bonded can be in the (S) configuration.
In a compound of subgenus (2A), the carbon atom to which $R^1$ is bonded can be in the ® configuration.
In a compound of subgenus (2A), $R^3$ can be hydrogen.
In a compound of subgenus (2A), $R^3$ can be $C_{1-3}$ alkyl.
In a compound of subgenus (2A), the carbon atom to which $R^3$ is bonded can be in the (S) configuration.
In a compound of subgenus (2A), the carbon atom to which $R^3$ is bonded can be in t(R) configuration.
In a compound of subgenus (2A), $R^4$ can be hydrogen.
In a compound of subgenus (2A), $R^4$ can be $C_{1-3}$ alkyl.
In a compound of subgenus (2A), $R^5$ can be $C_{1-3}$ alkyl.
In a compound of subgenus (2A), $R^5$ can be —C(=O)—$R^{10}$.

A compound of Formula (1) can have the structure of subgenus (4A), wherein, $R^1$ can be selected from hydrogen and methyl;
$R^2$ can be a moiety of Formula (4);
n can be 1; and
$R^9$ can be selected from $C_{1-3}$ alkyl.

In a compound of subgenus (4A), $R^1$ can be hydrogen.
In a compound of subgenus (4A), $R^1$ can be methyl.
In a compound of subgenus (4A), the carbon atom to which $R^1$ is bonded can be in the (S) configuration.
In a compound of subgenus (4A), the carbon atom to which $R^1$ is bonded can be in the (R) configuration.
In a compound of subgenus (4A), $R^3$ can be hydrogen.
In a compound of subgenus (4A), $R^3$ can be methyl.

A compound of Formula (1) can have the structure of subgenus (5A), wherein, $R^1$ can be selected from hydrogen and methyl;
$R^2$ can be a moiety of Formula (5); and
$R^7$ can be selected from $C_{1-3}$ alkyl.

In a compound of subgenus (5A), $R^1$ can be hydrogen.
In a compound of subgenus (5A), $R^1$ can be methyl.
In a compound of subgenus (5A), the carbon atom to which $R^1$ is bonded can be in the (S) configuration.
In a compound of subgenus (5A), the carbon atom to which $R^1$ is bonded can be in the (R) configuration.
In a compound of subgenus (5A), $R^7$ can be methyl.

A compound of Formula (1) can have the structure of subgenus (6A), wherein, $R^1$ can be selected from hydrogen and methyl;
$R^2$ can be a moiety of Formula (6); and
$R^8$ is selected from —$NH_2$.

In a compound of subgenus (6A), $R^1$ can be hydrogen.
In a compound of subgenus (6A), $R^1$ can be methyl.
In a compound of subgenus (6A), the carbon atom to which $R^1$ is bonded can be in the (S) configuration.

In a compound of subgenus (6A), the carbon atom to which $R^1$ is bonded can be in the (R) configuration.

A compound of Formula (1) can exhibit a ketamine oral bioavailability (% F) of at least 10%, at least 20%, at least 30%, at least 40%, at least 50%, or at least 60%. A compound of Formula (1) can provide a ketamine oral availability, for example, from 5% to 90% from, 10% to 80%, from 15% to 70%, or from 20% to 60%.

A compound of Formula (1) or a pharmaceutically acceptable salt thereof can have a higher solubility in a 0.1N hydrochloride solution than in 50 mM acetate buffer at pH 4.5.

A ketamine derivative can comprise ((((S)-1-(2-chlorophenyl)-2-oxocyclohexyl)(methyl)carbamoyl)oxy)methyl dimethyl-L-valinate (39):

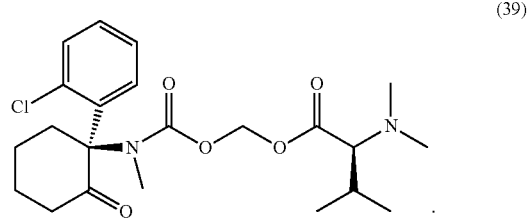 [SMILES: CC(C)[C@@H](C(=O)OCOC(=O)N(C)[C@]1(c2ccccc2Cl)CCCCC1=O)N(C)C]

(39)

or a pharmaceutically acceptable salt thereof.

The ketamine derivative of Formula (39) can be the hydrochloride salt.

The ketamine derivative of Formula (39) can be the free base.

A compound of Formula (1) can be selected from 1-((((S)-1-(2-chlorophenyl)-2-oxocyclohexyl)(methyl)carbamoyl)oxy)ethyl acetylglycinate (3) and 1-(((R)-1-(2-chlorophenyl)-2-oxocyclohexyl)(methyl)carbamoyl)oxy)ethyl acetylglycinate (62):

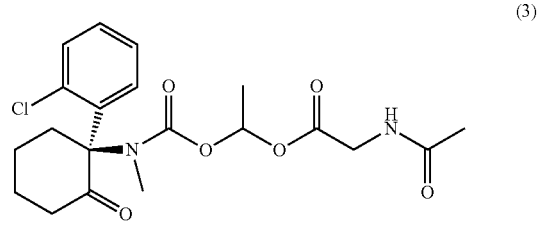

(3)

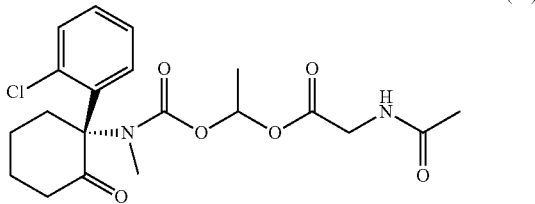

(62)

or a pharmaceutically acceptable salt thereof.

The compound of Formula (1) can be selected from 1-(((((S)-1-(2-chlorophenyl)-2-oxocyclohexyl)(methyl)carbamoyl)oxy)ethyl 2-(3-methyloxetan-3-yl)acetate (6) and 1-(((R)-1-(2-chlorophenyl)-2-oxocyclohexyl)(methyl)carbamoyl)oxy)ethyl 2-(3-methyloxetan-3-yl)acetate (63):

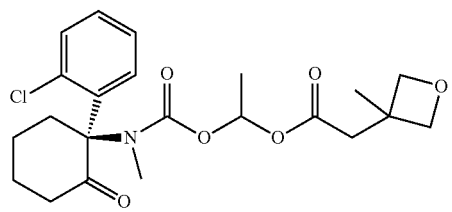

(6)

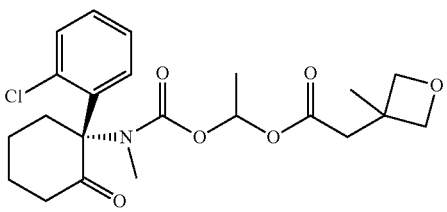

(63)

or a pharmaceutically acceptable salt of any of the foregoing.

The compound of Formula (1) can be selected from (S)-(((1-(2-chlorophenyl)-2-oxocyclohexyl)(methyl)carbamoyl)oxy)methyl 2-(3-methyloxetan-3-yl)acetate (22) and R)-(((1-(2-chlorophenyl)-2-oxocyclohexyl)(methyl)carbamoyl)oxy)methyl 2-(3-methyloxetan-3-yl)acetate (66):

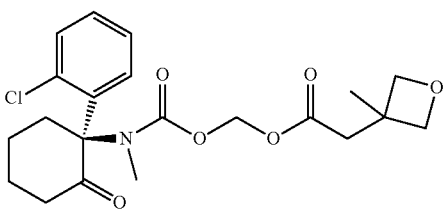

(22)

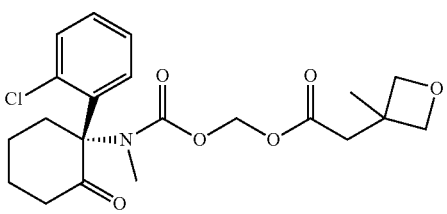

(66)

or a pharmaceutically acceptable salt of any of the foregoing.

The compound of Formula (1) can be selected from (((((S)-1-(2-chlorophenyl)-2-oxocyclohexyl)(methyl)carbamoyl)oxy)methyl dimethyl-L-valinate (39) and (((R)-1-(2-chlorophenyl)-2-oxocyclohexyl)(methyl)carbamoyl)oxy)methyl dimethyl-L-valinate (65):

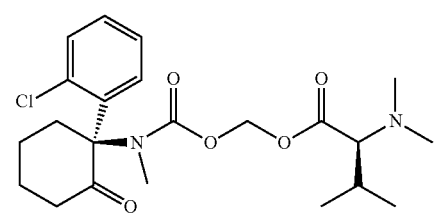

(39)

-continued

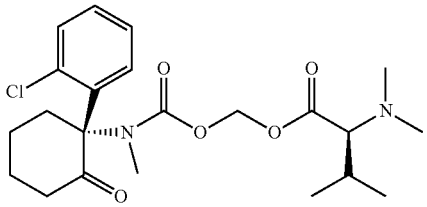

(65)

or a pharmaceutically acceptable salt of any of the foregoing.

The compound of Formula (1) can be selected from 1-(((((S)-1-(2-chlorophenyl)-2-oxocyclohexyl)(methyl)carbamoyl)oxy)ethyl acetyl-L-leucinate (57) and 1-(((R)-1-(2-chlorophenyl)-2-oxocyclohexyl)(methyl)carbamoyl)oxy)ethyl acetyl-L-leucinate (71):

(57)

(71)

or a pharmaceutically acceptable salt of any of the foregoing.

The compound of Formula (1) can be selected from 1-(((((S)-1-(2-chlorophenyl)-2-oxocyclohexyl)(methyl)carbamoyl)oxy)ethyl acetyl-L-alloisoleucinate (58) and 1-(((R)-1-(2-chlorophenyl)-2-oxocyclohexyl)(methyl)carbamoyl)oxy)ethyl acetyl-L-alloisoleucinate (72):

(58)

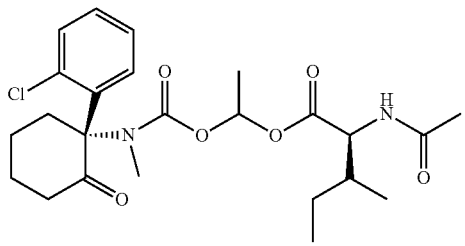

or a pharmaceutically acceptable salt of any of the foregoing.

Methods of synthesizing ketamine derivatives of Formula (1) are disclosed in U.S. Application Publication No. 2020/0231540 A1, which is incorporated by reference in its entirety.

An uncoated granule can comprise a ketamine derivative of Formula (1) and a granule binder.

An uncoated granule can comprise, for example, from 95.0 wt % to 99.5 wt % of a compound of Formula (1) or a pharmaceutically acceptable salt thereof, from 95.5 wt % to 99.0 wt %, from 96.0 wt % to 98.5 wt %, or from 96.5 wt % to 98.0 wt % of a compound of Formula (1) or a pharmaceutically acceptable salt thereof, wherein wt % is based on the total weight of the uncoated granule. An uncoated granule can comprise, for example, greater than 95 wt % of a compound of Formula (1) or a pharmaceutically acceptable salt thereof, such as greater than 96 wt %, greater than 97 wt %, greater than 98 wt %, or greater than 99 wt % of a compound of Formula (1) or a pharmaceutically acceptable salt thereof, wherein wt % is based on the total weight of the uncoated granule.

An uncoated granule can comprise a granule binder or combination of granule binders.

Examples of suitable granule binders include polyvinyl pyrrolidone, copovidone carbomer, corn starch, pregelatinized starch, carboxymethyl cellulose, hydroxypropyl methyl cellulose, polyethylene glycol, hydroxyethyl cellulose, hydroxypropyl cellulose, hydroxyethyl methyl cellulose, calcium carboxymethyl cellulose, guar galactomannan, ethylcellulose, chitosan hydrochloride, dextrin, hydroxypropyl starch, ceratonia, inulin, magnesium aluminum silicate, maltodextrin, methylcellulose, dextrates, polyethylene oxide, povidone, sodium alginate, starch, liquid glucose, sucrose, compressible sugar, zein, gelatin, polymethacrylate, sorbitol, glucose, sodium alginate, acacia, and combinations of any of the foregoing.

Examples of suitable granule binders include hydroxypropylmethyl cellulose, hydroxypropylcellulose, polyvinylpyrrolidone, or a combination of any of the foregoing.

A granule binder can comprise hydroxypropyl methylcellulose. A hydroxypropyl methylcellulose binder can have a viscosity, for example, from 2.4 mPa-sec to 3.6 mPa-sec, a 2910 substitution type, a methoxy content from 28% to 30%, and a hydroxypropyl content from 7% to 12%. A granule binder can comprise hydroxypropylmethyl cellulose E3. Hydroxypropylmethyl cellulose E3 is characterized by as 2910 substitution type and a viscosity of 3 mPa×sec in a 2 wt % aqueous solution at 20° C. An example of a hydroxypropylmethyl cellulose E3 is Pharmacoat® 603, available for Shin-Etsu Chemical Co., Ltd.

An uncoated granule can comprise, for example, from 0.5 wt % to 5 wt % of a granule binder, from 1 wt % to 4 wt %, or from 1.5 wt % to 3.5 wt % of a granule binder, wherein wt % is based on the total weight of the uncoated granule. An uncoated granule can comprise, for example, less than 5 wt % of a granule binder, less than 4 wt %, less than 3 wt %, less than 2 wt %, or less than 1 wt % of a granule binder, where wt % is based on the total weight of the uncoated granule.

An uncoated granule can comprise, for example, from 97 wt % to 99 wt % of a compound of Formula (1) or a pharmaceutically acceptable salt thereof, and from 1 wt % to 3 wt % of a granule binder, wherein wt % is based on the total weight of the uncoated granule.

An uncoated granule can comprise, for example, a mean average diameter from 100 µm to 500 µm, from 150 µm to 400 µm or from 200 µm to 300 µm, where the mean average diameter is determined by laser diffraction or by sieve analysis.

A pharmaceutical composition provided by the present disclosure can comprise, for example, from 35 wt % to 55 wt % of the uncoated granules, or from 40 wt % to 50 wt % of the uncoated granules, where wt % is based on the total weight of the pharmaceutical composition.

A pharmaceutical composition provided by the present disclosure can comprise, for example, greater than 35 wt % of the uncoated granules, greater than 40 wt %, or greater than 50 wt % of the uncoated granules, where wt % is based on the total weight of the pharmaceutical composition.

A pharmaceutical composition provided by the present disclosure can comprise, for example, less than 50 wt % of the uncoated granules, less than 45 wt %, or less than 40 wt % uncoated granules, where wt % is based on the total weight of the pharmaceutical composition.

An uncoated granule can comprise, for example, less than 1.0 wt % water, less than 0.75 wt %, less than 0.5 wt %, less than 0.25 wt %, or less than 0.1 wt % water, where wt % is based on the total weight of the granules. An uncoated granule can comprise, for example, from 0.01 wt % to 1.0 wt % water, from 0.1 wt % to 0.75 wt % water, or from 0.1 wt % to 0.5 wt % water, or from 0.1 wt % to 0.4 wt % water, where wt % is based on the total weight of the uncoated granules.

Uncoated granules can be prepared, for example, by (a) granulating a dry mixture of constituents to provide a dry granulation; and (b) adding solvent such as, for example, water, ethanol, isopropanol, and/or acetone to the dry granulation and granulating to provide a wet granulation.

Dry blending the dry mixture can comprise, for example, granulating for from 5 minutes to 20 minutes such as from 5 minutes to 15 minutes or from 5 minutes to 10 minutes, at a mixer speed, for example, from 700 rpm to 1000 rpm, such as from 800 rpm to 900 rpm; and at a chopper speed, for example, from 3,000 rpm to 4,200 rpm, such as from 3,200 rpm to 4,000 rpm, or from 3,400 rpm to 3,800 rpm.

The dry mixture obtained in step (a) can be wet granulated.

During wet granulation, water can be added to the dry mixture at a rate, for example, from 0.0025 wt %/min to 0.0075 wt %/min, where wt % is based on the total weight of the dry mixture. The wet granulation can be granulated, for example, for from 5 minutes to 20 minutes, such as from 5 minutes to 15 minutes, or from 5 minutes to 10 minutes. During wet granulation the mixer speed can be, for example, from 700 rpm to 1,000 rpm, such as from 800 rpm to 900 rpm; and the chopper speed can be, for example, from 3,000 rpm to 4,200 rpm, such as from 3,200 rpm to 4,000 rpm, or from 3,400 rpm to 3,800 rpm.

At the end of the process, the wet granulation can contain, for example, from 3 wt % to 15 wt % water, such as from 3 wt % to 12 wt %, from 3 wt % to 8 wt %, from 3.5 wt % to 6.5 wt %, or from 4 wt % water to 6 wt % water, where wt % is based on the total weight of the wet granulation.

The amount of water added is determined by weighing the amount of water incorporated into/consumed by the dry mixture.

During wet granulation the temperature of the wet granulation can be maintained, for example, between 20° C. and 25° C.

The wet granulation can then be wet massed to form smooth and high-density granules.

Wet massing can be done, for example, at a mixer speed from 400 rpm to 700 rpm such as from 500 rpm to 600 rpm, and a chopper speed, for example, from 1,300 rpm to 2,300 rpm such as from 1,500 rpm to 2,100 rpm for from 20 minutes to 100 minutes such as from 30 minutes to 90 minutes, from 30 minutes to 80 minutes, or from 30 minutes to 60 minutes.

During wet massing the temperature of the wet granulation can be maintained at a temperature, for example, from 20° C. to 25° C. such as from 22° C. to 25° C. The temperature of the granulation can be maintained, for example, by immersing the mixing bowl containing the granulation in a temperature-controlled bath.

Wet massing can be done, for example, using a granulation bowl with a mixer speed from 525 rpm to 575 rpm, and a chopper speed from 1,700 rpm to 1,900 rpm for from 20 minutes to 80 minutes such as from 25 minutes to 70 minutes, from 30 minutes to 60 minutes, or from 35 minutes to 55 minutes, at a temperature from 22° C. to 24° C.

During wet massing, the wet granulation can comprise, for example, from 1 wt % to 15 wt % water, from 2 wt % to 12 wt %, from 4 wt % to 10 wt %, or from 4 wt % to 8 wt % water, where wt % is based on the total weight of the wet granulation.

After wet massing, the wet granulation can be dried.

The wet granulation can be dried, for example, in an oven or in a fluid bed dryer until the loss on drying (LOD) or Karl Fischer analysis is less than 1.0 wt/wt %.

An uncoated granule provided by the present disclosure does not comprise a coating.

A granule provided by the present disclosure, referred to as a coated granule, can comprise one or more coatings.

A coating can have an average thickness, for example, less than 300 μm, less than 200 μm, less than 150 μm, less than 100 μm, less than 50 μm, or less than 25 μm.

A coated granule can comprise, for example, less than 50 wt %, less than 40 wt % of a coating, less than 30 wt %, less than 20 wt % or less than 10 wt % of a coating, where wt % is based on the total weight of the coated granule.

Dosage forms containing a highly water-soluble active pharmaceutical ingredient can benefit by having a coating to reduce the release rate of the active pharmaceutical ingredient and/or to increase the stability of the active pharmaceutical ingredient by minimizing water ingress.

A coating can comprise a pharmaceutically acceptable polymer, a plasticizing agent, an anti-tacking agent, a colorant or pigment, a glidant, a viscosity modifier, or a combination of any of the foregoing.

For example, a coating can comprise an immediate release coating, or a controlled-release coating. A controlled-release coating can comprise, for example, a delayed release coating, a pH-release coating, a sustained release coating, or a modified-release coating. A delayed release drug delivery system is designed to deliver drugs at a specified time or over a period of time following administration.

A coating can comprise a water-soluble coating and can include polymers such as polyvinyl alcohol, hydroxypropyl methylcellulose, polyvinylpyrrolidone, hydroxypropyl cellulose, hydroxypropyl ethylcellulose, polyethylene glycol, hydroxyethyl cellulose, and combinations of any of the foregoing.

A coating can comprise a water-insoluble coating or water-resistant coating to protect a dosage form from absorbing water during storage. Examples of suitable water-insoluble or water-resistant coatings can include polymers such as ethyl cellulose, poly-acrylates, polymethacrylates, and combinations of any of the foregoing.

A coating can provide, for example a time-dependent release, a pH-dependent release, or sustained release.

A coating can be applied to granules provided by the present disclosure by any suitable method such as by spraying a solution, suspension, or dispersion of the coating onto granules in a fluidized bed apparatus.

A coating provided by the present disclosure can comprise a controlled release polymer or combination of controlled release polymers.

Examples of suitable controlled release polymers include carbomer copolymers, shellac, carbomer homopolymers, hypromellose (hydroxypropyl methylcellulose) polymers, carbomer interpolymers, carboxymethylcellulose sodium, carrageenan, cellaburate, ethylcellulose, glyceryl monooleate, pregelatinized modified starch, glyceryl monostearate, guar gum, hydroxypropyl betadex, hydroxypropyl cellulose, polyethylene oxide, polyvinyl acetate dispersion, sodium alginate, pregelatinized starch, xanthan gum, alginic acid, ethylacrylate/methyl methacrylate copolymers, acrylic acid/allyl sucrose polymers, acrylic acid/allyl pentaerythritol polymers, acrylic acid/alkyl acrylate/allyl pentaerythritol copolymers, and a combination of any of the foregoing.

A controlled release polymer can comprise hydroxypropyl methylcellulose.

A pharmaceutical composition provided by the present disclosure can comprise a compound of Formula (1), which can be in the form of an uncoated granule comprising the compound of Formula (1) and a granule binder; a controlled release polymer such as a water-soluble polymer; microcrystalline cellulose, a surfactant, and a lubricant.

A pharmaceutical composition provided by the present disclosure can comprise, for example, from 30 wt % to 60 wt % of uncoated granules, from 35 wt % to 55 wt %, or from 40 wt % to 50 wt % of uncoated granules, where wt % is based on the total weight of the pharmaceutical composition.

A pharmaceutical composition provided by the present disclosure can comprise, for example, greater than 30 wt % of uncoated granules, greater than 35 wt %, greater than 40 wt %, greater than 45 wt %, greater than 50 wt % or greater than 55 wt % of the uncoated granules, where wt % is based on the total weight of the pharmaceutical composition.

A pharmaceutical composition provided by the present disclosure can comprise, for example, less than 60 wt %, less than 55 wt %, less than 50 wt %, less than 45 wt %, less than 40 wt %, or less than 35 wt % of the uncoated granules, where wt % is based on the total weight of the pharmaceutical composition.

A pharmaceutical composition provided by the present disclosure can comprise a controlled release polymer or a combination of controlled release polymers.

A controlled release polymer can be a water-soluble polymer.

Examples of suitable water-soluble polymers include hydroxypropyl cellulose, polyvinyl alcohol, hydroxypropylmethyl cellulose, hydroxypropylethyl cellulose, polyvinylpyrrolidone, polyethylene glycol, polyvinyl alcohol, povidone, copovidone, and poloxamer.

A water-soluble polymer can comprise hydroxypropylmethyl cellulose or a combination of different hydroxypropylmethyl cellulose polymers.

A hydroxypropyl methylcellulose-controlled release polymer can be characterized by a methoxyl content from 22% to 24%; a pH at 25° C. from 5 to 8 (2% in water); a hydroxypropyl content 7.5% to 8.5%; and a viscosity from 80 mPa-s (cP) to 120 mPa-s (Brookfield; 2% in water at 20° C.).

A hydroxypropyl methylcellulose-controlled release polymer can be characterized by a methoxyl content from 22% to 24%; a pH at 25° C. from 5 to 8 (2% in water); a hydroxypropyl content 7.5% to 8.5%; and a viscosity from 2,600 mPa-s (cP) to 5,000 mPa-s (Brookfield; 2% in water at 20° C.).

The hydroxypropylmethyl cellulose polymer can be selected from Methocel™ K100 Premium LV DC2, Methocel™ K4M Premium DC2, and a combination thereof. The Methocel™ products are available from Colorcon.

Hydroxypropyl methyl cellulose can comprise, for example, from 50 wt % to 100 wt % of a hydroxypropyl methylcellulose characterized a methoxyl content from 22% to 24%; a pH at 25° C. from 5 to 8 (2% in water); a hydroxypropyl content 7.5% to 8.5%; and a viscosity from 2,600 mPa-s (cP) to 5,000 mPa-s (Brookfield; 2% in water at 20° C.); and from 0 wt % to 50 wt % of a hydroxypropyl methylcellulose characterized by a methoxyl content from 22% to 24%; a pH at 25° C. from 5 to 8 (2% in water); a hydroxypropyl content 7.5% to 8.5%; and a viscosity from 2,600 mPa-s (cP) to 5,000 mPa-s (Brookfield; 2% in water at 20° C.);

where wt % is based on the total weight of the hydroxypropyl methylcellulose.

Hydroxypropyl methyl cellulose can comprise, for example, from 60 wt % to 100 wt % of a hydroxypropyl methylcellulose characterized a methoxyl content from 22% to 24%; a pH at 25° C. from 5 to 8 (2% in water); a hydroxypropyl content 7.5% to 8.5%; and a viscosity from 2,600 mPa-s (cP) to 5,000 mPa-s (Brookfield; 2% in water at 20° C.); and from 0 wt % to 40 wt % of a hydroxypropyl methylcellulose characterized by a methoxyl content from 22% to 24%; a pH at 25° C. from 5 to 8 (2% in water); a hydroxypropyl content 7.5% to 8.5%; and a viscosity from 2,600 mPa-s (cP) to 5,000 mPa-s (Brookfield; 2% in water at 20° C.);

where wt % is based on the total weight of the hydroxypropyl methylcellulose.

A pharmaceutical composition provided by the present disclosure can comprise, for example, from 10 wt % to 60 wt % of a water-soluble polymer such as hydroxypropylmethyl cellulose, from 10 wt % to 50 wt %, from 20 wt % to 40 wt %, from 22 wt % to 38 wt %, from 24 wt % to 36 wt %, from 26 wt % to 34 wt %, or from 28 wt %$ to 32 wt % of a water-soluble polymer such as hydroxypropylmethyl cellulose, where wt % is based on the total weight of the pharmaceutical composition.

A pharmaceutical composition provided by the present disclosure can comprise, for example, greater than 15 wt % of a water-soluble polymer such as hydroxypropylmethyl cellulose, greater than 20 wt %, greater than 25 wt %, greater than 30 wt %, or greater than 35 wt % of a water-soluble polymer, where wt % is based on the total weight of the pharmaceutical composition.

A pharmaceutical composition provided by the present disclosure can comprise, for example, less than 60 wt % of a water-soluble polymer such as hydroxypropylmethyl cellulose, less than 50 wt %, less than 35 wt %, less than 30 wt %, less than 25 wt %, or less than 20 wt % of a water-soluble polymer, where wt % is based on the total weight of the pharmaceutical composition.

A pharmaceutical composition provided by the present disclosure can comprise a surfactant or a combination of surfactants.

A suitable surfactant can form micelles at a high pH such as at greater than pH 4, greater than pH 5, or greater than pH 6.

A surfactant can comprise an anionic surfactant. Examples of suitable anionic surfactants include Typical anionic surfactants include soaps, alkylbenzene sulfonates, alkyl sulfonates, alkyl sulfonates, alkyl sulfates, salts of fluorinated fatty acids, silicones, fatty alcohol sulfates, polyoxyethylene fatty alcohol ether sulfates, α-olefin sulfonate, polyoxyethylene fatty alcohol phosphates ether, alkyl alcohol amide, alkyl sulfonic acid acetamide, alkyl succinate sulfonate salts, amino alcohol alkylbenzene sulfonates, naphthenates, alkylphenol sulfonate and polyoxyethylene monolaurate.

Other examples of suitable anionic surfactants include sodium lauryl sulfate, sodium laureth sulfate, ammonium lauryl sulfate, ammonium laureth sulfate, sodium stearate, potassium cocoate, sodium myristyl, palmityl sulfate, and disodium lauryl sulfosuccinate.

An anionic surfactant can comprise an anionic sulfate/sulfonate surfactant.

Examples of suitable anionic sulfate/surfactants include sodium lauryl sulfate, sodium laureth sulfate, ammonium lauryl sulfate, ammonium laureth sulfate, palmityl sulfate, and disodium lauryl sulfosuccinate.

An anionic sulfate/sulfonate surfactant can comprise sodium lauryl sulfate.

Sodium lauryl sulfate can be characterized by a critical micelle concentration, for example, from 1.5 g/L to 3.0 g/L such as from 1.7 g/L to 2.8 g/L or from 1.9 g/L to 2.6 g/L at 20° C., where the critical micelle concentration is determined using a force tensiometer.

A pharmaceutical composition provided by the present disclosure can comprise, for example, from 5 wt % to 15 wt % of an anionic sulfate/sulfonate surfactant, from 7 wt % to 13 wt %, or from 9 wt % to 11 wt % of an anionic sulfate/sulfonate surfactant, where wt % is based on the total weight of the pharmaceutical composition.

A pharmaceutical composition provided by the present disclosure can comprise, for example, greater than 5 wt % of an anionic sulfate/sulfonate surfactant, greater than 7 wt %, greater than 9 wt %, greater than 11 wt %, or greater than 13 wt % of an anionic sulfate/sulfonate surfactant, where wt % is based on the total weight of the pharmaceutical composition.

A pharmaceutical composition provided by the present disclosure can comprise, for example, less than 15 wt % of an anionic sulfate/sulfonate surfactant, less than 13 wt %, less than 11 wt %, less than 9 wt %, or less than 7 wt % of an anionic sulfate/sulfonate surfactant, where wt % is based on the total weight of the pharmaceutical composition.

A pharmaceutical composition provided by the present disclosure can comprise, for example, from 30 wt % to 60 wt % of uncoated granules, from 10 wt % to 60 wt % of a controlled release polymer such as a water-soluble polymer, and from 5 wt % to 15 wt % of an anionic sulfate/sulfonate surfactant, where wt % is based on the total weight of the pharmaceutical composition.

A pharmaceutical composition provided by the present disclosure can comprise, for example, from 35 wt % to 55 wt % of uncoated granules, from 15 wt % to 35 wt % of a controlled release polymer such as a water-soluble polymer, and from 7 wt % to 13 wt % of an anionic sulfate/sulfonate surfactant, where wt % is based on the total weight of the pharmaceutical composition.

A pharmaceutical composition provided by the present disclosure can comprise, for example, from 40 wt % to 50 wt % of uncoated granules, from 20 wt % to 30 wt % of a controlled release polymer such as a water-soluble polymer, and from 9 wt % to 11 wt % of an anionic sulfate/sulfonate surfactant, wherein wt % is based on the total weight of the pharmaceutical composition.

A pharmaceutical composition provided by the present disclosure can have a water content, for example, less than 3 wt %, less than 2.5 wt %, less than 2.0 wt %, less than 1.5 wt %, less than 1.0 wt %, or less than 0.5 wt %, where wt % is based on the total weight of the pharmaceutical composition. A pharmaceutical composition provided by the present disclosure can have a water content, for example, from 0.1 wt % to 3 wt %, from 0.1 wt % to 2 wt %, or from 0.1 wt % to 1.0 wt %, where wt % is based on the total weight of the composition.

A pharmaceutical composition provided by the present disclosure can comprise a filler or combination of filler.

Examples of suitable filler include microcrystalline cellulose, powdered cellulose, anhydrous lactose, lactose monohydrate, spray-dried lactose, mannitol, starch, pregelatinized starch, maize starch, corn starch, sorbitol, sucrose, compressible sugar, confectioner's sugar, sugar spheres, dextrate, dextrin, dextrose, calcium phosphate, dibasic, anhydrous, calcium carbonate, maltose, maltodextrin, kaolin, calcium phosphate, dibasic, dihydrate, tribasic calcium phosphate, calcium sulfate, cellaburate, calcium lactate, cellulose acetate, silicified microcrystalline cellulose, cellulose acetate, corn syrup, pregelatinized starch and corn starch, corn syrup, solids, erythritol, ethylcellulose, ethyl acrylate and methyl methacrylate copolymer dispersion, fructose, isomaltose, alpha-lactalbumin, lactitol, magnesium carbonate, magnesium oxide, methacrylic acid and ethyl acrylate copolymer, methacrylic acid and methyl methacrylate copolymer, polydextrose, sodium chloride, simethicone, pregelatinized modified starch, starch, pea, hydroxypropyl pea starch, starch, pregelatinized hydroxypropyl pea, potato starch, starch, hydroxypropyl potato, pregelatinized hydroxypropyl potato starch, starch, tapioca, wheat starch, starch hydrolysate, hydrogenated, pullulan, talc, amino methacrylate copolymer, trehalose, xylitol, and combinations of any of the foregoing.

A filler can comprise microcrystalline cellulose.

Microcrystalline cellulose can have an average particle size, for example, from 80 μm to 120 μm or from 90 μm to 110 μm, as determined using sieve analysis or laser diffraction.

Microcrystalline cellulose can comprise, for example, Avicel® PH 102.

A pharmaceutical composition provided by the present disclosure can comprise, for example, from 5 wt % to 35 wt % of a filler, from 10 wt % to 30 wt %, from 10 wt % to 20 wt %, from 25 wt % to 35 wt %, or from 15 wt % to 25 wt % of a filler, where wt % is based on the total weight of the pharmaceutical composition.

A pharmaceutical composition provided by the present disclosure can comprise, for example, greater than 5 wt % of a filler, greater than 10 wt %, greater than 15 wt %, greater than 20 wt %, greater than 25 wt %, or greater than 30 wt % of a filler, where wt % is based on the total weight of the pharmaceutical composition.

A pharmaceutical composition provided by the present disclosure can comprise, for example, less than 35 wt % of a filler, less than 30 wt % less than 25 wt %, less than 20 wt %, or less than 15 wt % of a filler, where wt % is based on the total weight of the pharmaceutical composition.

A pharmaceutical composition provided by the present disclosure can comprise a lubricant or combination of lubricants.

Examples of suitable lubricants include magnesium stearate, magnesium silicate, calcium stearate, sodium lauryl sulfate, sodium stearyl fumarate, magnesium lauryl sulfate, stearic acid, calcium stearate, glyceryl behenate, behenoyl polyoxylglycerides, glyceryl dibehenate, lauric acid, glyceryl monostearate, glyceryl tristearate, myristic acid, palmitic acid, poloxamer, polyethylene glycol, polysorbate, polyoxyl 10 oleyl ether, polyoxyl 15 hydroxystearate, polysorbate, potassium benzoate, sodium benzoate, sorbitan monolaurate, sorbitan monooleate, sodium stearate, sorbitan monopalmitate, sorbitan monostearate, zinc stearate, sorbitan sequioleate, sorbitan trioleate, talc, and combinations of any of the foregoing.

A lubricant can comprise magnesium stearate.

A pharmaceutical composition provided by the present disclosure can comprise, for example, from 0.1 wt % to 3.5 wt % of a lubricant, from 0.2 wt % to 2.0 wt %, from 0.2 wt % to 1.0 wt %, or from 0.3 wt % to 0.7 wt % of a lubricant, where wt % is based on the total weight of the pharmaceutical composition.

A pharmaceutical composition provided by the present disclosure can comprise, for example, greater than 0.1 wt % of a lubricant, greater than 0.25 wt %, greater than 0.5 wt %, or greater than 1.0 wt % of a lubricant, where wt % is based on the total weight of the pharmaceutical composition.

A pharmaceutical composition provided by the present disclosure can comprise, for example, less than 1.5 wt % of a lubricant, less than 1.0 wt %, or less than 0.5 wt % of a lubricant, where wt % is based on the total weight of the pharmaceutical composition.

A pharmaceutical composition provided by the present disclosure in the form of a granulation can be prepared as described in the examples.

A pharmaceutical composition provided by the present disclosure in the form of a granulation can have a bulk density, for example, from 0.45 g/mL to 0.51 g/mL, from 0.46 g/mL to 0.50 g/mL, or from 0.47 g/mL to 0.49 g/mL, where bulk density is determined using a bulk density cylinder.

A pharmaceutical composition provided by the present disclosure in the form of a granulation can have an angle of repose, for example, from 35 degrees to 45 degrees, from 36 degrees to 44 degrees, or from 38 degrees to 42 degrees.

A pharmaceutical composition provided by the present disclosure in the form of a granulation can have an intrinsic flowability value, for example, from 7 to 14, from 8 to 13, or from 9 to 12, where the intrinsic flowability value is determined according to USP <1174> using a Flodex™ instrument.

A pharmaceutical composition provided by the present disclosure can comprise a diluent, a disintegrant, a glidant, a coloring agent, a flavoring agent, a sweetening agent, a release-modifying agent, or a combination of any of the foregoing.

An oral dosage form provided by the present disclosure can comprise a pharmaceutical composition provided by the present disclosure. Examples of suitable oral dosage forms include tablets, lozenges, capsules, sachets, solutions, and suspensions.

An oral dosage form can comprise, for example, a solid oral dosage form, such as a tablet.

An oral dosage form can comprise, for example, an uncoated tablet, a coated tablet, an immediate-release coated tablet, an enteric-coated tablet, a dispersible tablet, a modified-release tablet such as a sustained release tablet, a delated release tablet, or a controlled release tablet, an effervescent tablet, a lozenge, or a sublingual tablet.

An oral dosage form can provide a therapeutically effective amount of a compound of Formula (1) or a metabolite thereof for treating a disease in a patient.

An oral dosage form provided by the present disclosure can comprise, for example, from 1 mg ketamine equivalents to 100 mg ketamine equivalents such as from 10 mg to 90 mg, from 20 mg to 80 mg, from 30 mg to 70 mg, or from 40 mg to 60 mg ketamine equivalents. An oral dosage form provided by the present disclosure can comprise, for example, greater than 10 mg ketamine equivalents, greater than 20 mg, greater than 40 mg, greater than 60 mg, or greater than 80 mg ketamine equivalents. An oral dosage form provided by the present disclosure can comprise, for example, less than 100 mg ketamine equivalents, less than 80 mg, less than 60 mg, less than 40 mg, or less than 20 mg ketamine equivalents.

An oral dosage form can comprise, for example, from 10 mg to 500 mg of a compound of Formula (1), from 50 mg to 450 mg, from 100 mg to 400 mg, or from 150 mg to 350 mg of a compound of Formula (1). An oral dosage form can comprise, for example, greater than 10 mg of a compound of Formula (1), greater than 50 mg, greater than 100 mg, greater than 200 mg, greater than 300 mg, or greater than 400 mg of a compound of Formula (1).

An oral dosage form can comprise, for example, from 1 mg to 500 mg equivalents ketamine, from 10 mg to 400 mg equivalents, or from 50 mg equivalents to 300 mg equivalents ketamine. An oral dosage form can comprise, for example, from 1 mg to 1,000 mg of a compound of Formula (1), from 20 mg to 800 mg, or from 100 mg to 600 mg of a compound of Formula (1).

A solid oral dosage form such as a tablet can be prepared, for example, by compressing a pharmaceutical granulation provided by the present disclosure in a tablet press using 9 mm tooling, a press speed of 20 RPM, and a compression force of about 28 kN.

A solid oral dosage form such as a tablet provided by the present disclosure can have a hardness, for example, from 4 kP to 10 kP, from 8 kP to 10 kP or from 8.5 kP to 9.5 kP, where hardness is determined according to USP <1217> (Tablet Breaking Force).

A solid oral dosage form such as a tablet provided by the present disclosure can have a thickness for example, from 5 mm to 10 mm, from 6 mm to 9 mm, or from 7 mm to 8 mm, where hardness is determined according to USP <1217> using diametral compression.

A solid oral dosage form such as a tablet provided by the present disclosure can have a weight, for example, from 245 mg to 255 mg.

A solid oral dosage form such as a tablet provided by the present disclosure can have a weight, for example, of less than 0.2 such as about 0.1 where friability is determined using an ionic sifter.

A tablet provided by the present disclosure can comprise an immediate release coating or a seal coating.

An immediate release coating refers to a coating that completely dissolves to release ketamine, for example, in less than 10 minutes, less than 8 minutes, less than 6 minutes, less than 5 minutes, or less than 4 minutes, when tested in a USP Type 2 dissolution apparatus in a buffered solution at pH 4.5 at a temperature of 37° C. and a paddle speed of 100 rpm.

An immediate release coating can comprise a water-soluble polymer such as, for example, hydroxypropylcellulose, polyvinyl alcohol, hydroxypropylmethylcellulose, hydroxypropylethylcellulose, polyvinylpyrrolidone, or polyethyleneglycol.

A solid oral dosage form such as a tablet provided by the present disclosure can exhibit a zero-order release profile of the compound of Formula (1) or a pharmaceutically acceptable salt thereof over at least 6 hours, at least 8 hours, or at least 10 hours in a two-stage dissolution medium as determined using a USP I dissolution apparatus with an agitation rate of 100 RPM at a temperature of 37° C., wherein, the first stage comprises immersing the solid dosage in 0.1N hydrochloric acid for 1 hour; and the second stage comprises immersing the oral dosage form in a 50 mM acetate buffer at pH 4.5 for the duration.

A solid oral dosage form such as a tablet provided by the present disclosure can be characterized by a dissolution profile of a compound of Formula (1) or a pharmaceutically acceptable salt thereof in a two-stage dissolution medium as determined using a USP I dissolution apparatus with an agitation rate of 100 RPM and at a temperature of 37° C., wherein, from 20% to 40% of the compound of Formula (1) is released at 2 hours;

from 30% to 50% of the compound of Formula (1) is released at 4 hours;

from 70% to 80% of the compound of Formula (1) is released at 8 hours;

from 80% to 100% of the compound of Formula (1) is released at 12 hours;

from 80% to 100% of the compound of Formula (1) is released at 16 hours;

the first stage comprises immersing the oral dosage form in 0.1N hydrochloric acid for 1 hour;

the second stage comprises immersing the oral dosage form in a 50 mM acetate buffer at pH 4.5 for the duration; and percent (%) is based on the total amount of the compound of Formula (1) or a pharmaceutically acceptable salt thereof in the oral dosage form, A solid oral dosage form provided by the present disclosure can be characterized by a dissolution profile of a compound of Formula (1) or a pharmaceutically acceptable salt thereof in a two-stage dissolution medium as determined using a USP I dissolution apparatus with an agitation rate of 100 RPM at a temperature of 37° C., wherein, from 30% to 40% of the compound of Formula (1) is released at 2 hours;

from 50% to 70% of the compound of Formula (1) is released at 4 hours;

from 70% to 90% of the compound of Formula (1) is released at 8 hours;

greater than 90% of the compound of Formula (1) is released at 12 hours;

the first stage comprises immersing the oral dosage form in 0.1N hydrochloric acid for 1 hour;

the second stage comprises immersing the oral dosage form in a 50 mM acetate buffer at pH 4.5 for the duration; and percent (%) is based on the total amount of the compound of Formula (1) or a pharmaceutically acceptable salt thereof in the oral dosage form.

A solid oral dosage form provided by the present disclosure can be characterized by a dissolution profile of a compound of Formula (1) or a pharmaceutically acceptable salt thereof in a two-stage dissolution medium as determined using a USP I dissolution apparatus with an agitation rate of 100 RPM at a temperature of 37° C., wherein, from 15% to 25% of the compound of Formula (1) is released at 2 hours;

from 20% to 35% of the compound of Formula (1) is released at 4 hours;

from 50% to 60% of the compound of Formula (1) is released at 8 hours;

from 70% to 85% of the compound of Formula (1) is released at 12 hours;

from 80% to 100% is of the compound of Formula (1) released at 16 hours;

the first stage comprises immersing the oral dosage form in 0.1N hydrochloric acid for 1 hour;

the second stage comprises immersing the oral dosage form in a 50 mM acetate buffer at pH 4.5 for the duration; and percent (%) is based on the total amount of the compound of Formula (1) or a pharmaceutically acceptable salt thereof in the oral dosage form.

A solid oral dosage form such as a tablet provided by the present disclosure can be characterized by a dissolution profile of a compound of Formula (1) or a pharmaceutically acceptable salt thereof in a two-stage dissolution medium as determined using a USP I dissolution apparatus with an agitation rate of 100 RPM at a temperature of 37° C., that is bioequivalent to any one of the dissolution profiles shown in FIG. 1, where the first stage comprises immersing the oral dosage form in 0.1N hydrochloric acid for 1 hour; the second stage comprises immersing the oral dosage form in a 50 mM acetate buffer at pH 4.5 for the duration.

A solid oral dosage form such as a tablet provided by the present disclosure can be characterized by a dissolution profile of a compound of Formula (1) or a pharmaceutically acceptable salt thereof in a two-stage dissolution medium as determined using a USP I dissolution apparatus with an agitation rate of 100 RPM at a temperature of 37° C., that is bioequivalent to any one of the dissolution profiles shown in FIG. 1, where the first stage comprises immersing the oral dosage form in 0.1N hydrochloric acid for 1 hour; the second stage comprises immersing the oral dosage form in a 50 mM acetate buffer at pH 4.5 for the duration.

Following oral administration of a solid oral dosage form such as a tablet provided by the present disclosure to a population of fasted, healthy subjects, the plasma esketamine concentration can be bioequivalent to any one of the pharmacokinetic profiles presented in FIGS. 4A, 5, 6A, and 7A, and as summarized in any one of Tables 8-11.

Following oral administration of a solid oral dosage form such as a tablet provided by the present disclosure to a population of fasted, healthy subjects, the plasma noresketamine concentration can be bioequivalent to any one of the pharmacokinetic profiles presented in FIGS. 4B, 5, 6B, and 7B, and as summarized in any one of Tables 8-11.

Following oral administration of a solid oral dosage form such as a tablet comprising 100 mg of a compound of Formula (1) provided by the present disclosure to a population of fasted, healthy subjects, the Cmax of the mean plasma esketamine concentration can be, for example, from 5 ng/mL to 10 ng/mL, from 6 ng/mL to 9 ng/mL, or from 6.5 ng/mL to 8.5 ng/mL.

Following oral administration of a solid oral dosage form such as a tablet comprising 100 mg of a compound of Formula (1) provided by the present disclosure to a population of fasted, healthy subjects, the Cmax of the mean plasma noresketamine concentration can be, for example, from 40 ng/mL to 80 ng/mL, from 45 ng/mL to 75 ng/mL, from 50 ng/mL to 70 ng/mL, or from 55 ng/mL to 65 ng/mL.

Following oral administration of a solid oral dosage form such as a tablet comprising 100 mg of a compound of Formula (1) provided by the present disclosure to a population of fasted, healthy subjects, the Cmax of the mean plasma esketamine concentration can be, for example, less than 11 ng/mL, less than 9 ng/mL, less than 7 ng/mL or less than 5 ng/mL.

Following oral administration of a solid oral dosage form such as a tablet comprising 100 mg of a compound of Formula (1) provided by the present disclosure to a population of fasted, healthy subjects, the Cmax of the mean plasma noresketamine concentration can be, for example, less than 100 ng/mL, less than 80 ng/mL, or less than 60 ng/mL.

Following oral administration of a solid oral dosage form such as a tablet comprising 100 mg of a compound of Formula (1) provided by the present disclosure to a population of fasted, healthy subjects, the Tmax of the mean plasma esketamine concentration can be, for example, from 2 minutes to 6 minutes, from 2.5 minutes to 5.5 minutes, of from 3 minutes to 5 minutes.

Following oral administration of a solid oral dosage form such as a tablet comprising 100 mg of a compound of Formula (1) provided by the present disclosure to a population of fasted, healthy subjects, the Tmax of the mean plasma noresketamine concentration can be, for example, from 3 minutes to 6 minutes from 3.5 minutes to 5.5 minutes, or from 4 minutes to 5 minutes.

Following oral administration of a solid oral dosage form such as a tablet comprising 100 mg of a compound of Formula (1) provided by the present disclosure to a population of fasted, healthy subjects, the t½ of the mean plasma esketamine concentration can be, for example, from 5 minutes to 15 minutes, from 6 minutes to 12 minutes, from 7 minutes to 11 minutes, or from 8 to 10 minutes.

Following oral administration of a solid oral dosage form such as a tablet comprising 100 mg of a compound of Formula (1) provided by the present disclosure to a population of fasted, healthy subjects, the t½ of the mean plasma noresketamine concentration can be, for example, from 8 minutes to 12 minutes from 8.5 minutes to 11.5 minutes, or from 9 minutes to 11 minutes.

Following oral administration of a solid oral dosage form such as a tablet comprising 100 mg of a compound of Formula (1) provided by the present disclosure to a population of fasted, healthy subjects, the mean plasma esketamine AUC0-inf can be, for example, from 60 hr×ng/mL to 120 hr×ng/mL, from 70 hr×ng/mL to 110 hr×ng/mL, or from 80 hr×ng/mL to 100 hr×ng/mL.

Following oral administration of a solid oral dosage form such as a tablet comprising 100 mg of a compound of Formula (1) provided by the present disclosure to a population of fasted, healthy subjects, the mean plasma esketamine AUC0-inf can be, for example, greater than 50 hr×ng/mL, greater than 100 hr×ng/mL, greater than 150 hr×ng/mL, or greater than 200 hr×ng/mL.

Following oral administration of a solid oral dosage form such as a tablet comprising 100 mg of a compound of Formula (1) provided by the present disclosure to a population of fasted, healthy subjects, the mean plasma noresketamine AUC0-inf can be, for example, from 850 hr×ng/mL to 1,000 hr×ng/mL, from 875 hr×ng/mL to 975 hr×ng/mL, or from 850 hr×ng/mL to 950 hr×ng/mL.

Following oral administration of a solid oral dosage form such as a tablet comprising 100 mg of a compound of Formula (1) provided by the present disclosure to a population of fasted, healthy subjects, the mean plasma noresketamine AUC0-inf can be, for example, greater than 600 hr×ng/mL, greater than 800 hr×ng/mL, greater than 1,000 hr×ng/mL, or greater than 1,200 hr×ng/mL.

Following oral administration of a solid oral dosage form such as a tablet comprising 100 mg of a compound of Formula (1) provided by the present disclosure to a population of fasted, healthy subjects, the mean plasma esketamine AUC0-12 can be, for example, from 20 hr×ng/mL to 40 hr×ng/mL, from 22 38 hr×ng/mL to 38 hr×ng/mL, from 24 hr×ng/mL to 36 hr×ng/mL, or from 26 hr×ng/mL to 34 hr×ng/mL.

Following oral administration of a solid oral dosage form such as a tablet comprising 100 mg of a compound of Formula (1) provided by the present disclosure to a population of fasted, healthy subjects, the mean plasma esketamine AUC0-12 can be, for example, greater than 20 hr×ng/mL, greater than 30 hr×ng/mL, greater than 40 hr×ng/mL, or greater than 50 hr×ng/mL.

Following oral administration of a solid oral dosage form such as a tablet comprising 100 mg of a compound of Formula (1) provided by the present disclosure to a population of fasted, healthy subjects, the mean plasma noresketamine AUC0-12 can be, for example, from 300 hr×ng/mL to 500 hr×ng/mL, from 325 hr×ng/mL to 475 hr×ng/mL, from 350 hr×ng/mL to 450 hr×ng/mL, or from 375 hr×ng/mL to 425.

Following oral administration of a solid oral dosage form such as a tablet comprising 100 mg of a compound of Formula (1) provided by the present disclosure to a population of fasted, healthy subjects, the mean plasma noresketamine AUC0-12 can be, for example, greater than 200 hr×ng/mL, greater than 300 hr×ng/mL, greater than 400 hr×ng/mL, or greater than 500 hr×ng/mL.

Following oral administration of a solid oral dosage form such as a tablet comprising 100 mg of a compound of Formula (1) provided by the present disclosure to a population of fasted, healthy subjects, the mean plasma esketamine Cmax/Cave(0-12h) can be, for example, from 2 to 4, from 2.2 to 3.8, from 2.4 to 3.6, or from 2.6 to 3.4.

Following oral administration of a solid oral dosage form such as a tablet comprising 100 mg of a compound of Formula (1) provided by the present disclosure to a population of fasted, healthy subjects, the mean plasma noresketamine Cmax/Cave(0-12h) can be, for example, from, 1.5 to 3, from 1.7 to 2.8, from 1.9 to 2.6, or from 2.1 to 2.4.

Following oral administration of a solid oral dosage form such as a tablet comprising 100 mg of a compound of Formula (1) provided by the present disclosure to a population of fasted, healthy subjects, the mean plasma esketamine Cmax/Cave(0-12h) can be, for example, less than 4.0, less than 3.5, less than 3.0, or less than 2.5.

Following oral administration of a solid oral dosage form such as a tablet comprising 100 mg of a compound of Formula (1) provided by the present disclosure to a population of fasted, healthy subjects, the mean plasma noresketamine Cmax/Cave(0-12h) can be, for example, less than 3.0, less than 2.5, or less than 2.0.

Following oral administration of a solid oral dosage form such as a tablet comprising from 100 mg to 400 mg of a compound of Formula (1) provided by the present disclosure to a population of fasted, healthy subjects, the Cmax of the mean plasma esketamine concentration can be, for example, from 5 ng/mL to 35 ng/mL, from 10 ng/mL to 30 ng/mL, or from 15 ng/mL to 25 ng/mL.

Following oral administration of a solid oral dosage form such as a tablet comprising from 100 mg to 400 mg of a compound of Formula (1) provided by the present disclosure to a population of fasted, healthy subjects, the Cmax of the mean plasma noresketamine concentration is, for example, from 50 ng/mL to 300 ng/mL, from 100 ng/mL to 250 ng/mL, or from 100 ng/mL to 200 ng/mL.

Following oral administration of a solid oral dosage form such as a tablet comprising from 100 mg to 400 mg of a compound of Formula (1) provided by the present disclosure to a population of fasted, healthy subjects, the Cmax of the mean plasma esketamine concentration can be, for example, less than 50 ng/mL, less than 40 ng/mL, less than 35 ng/mL, less than 30 ng/mL, less than 25 ng/mL, less than 20 ng/mL, or less than 15 ng/mL.

Following oral administration of a solid oral dosage form such as a tablet comprising from 100 mg to 400 mg of a compound of Formula (1) provided by the present disclosure to a population of fasted, healthy subjects, the Cmax of the mean plasma noresketamine concentration is, for example, less than 350 ng/mL, less than 300 ng/mL, less than 250 ng/mL, less than 200 ng/mL, less than 150 ng/mL, less than 100, or less than 50 ng/mL.

Following oral administration of a solid oral dosage form such as a tablet comprising from 100 mg to 400 mg of a compound of Formula (1) provided by the present disclosure to a population of fasted, healthy subjects, the Tmax of the mean plasma esketamine concentration can be, for example, from 2 minutes to 5 minutes, from 2.5 minutes to 5.0 minutes, of from 3.0 minutes to 4.0 minutes.

Following oral administration of a solid oral dosage form such as a tablet comprising from 100 mg to 400 mg of a compound of Formula (1) provided by the present disclosure to a population of fasted, healthy subjects, the Tmax of the mean plasma noresketamine concentration can be, for example, from 3 minutes to 8 minutes from 3.0 minutes to 7.0 minutes, or from 3.0 minutes to 5.0 minutes.

Following oral administration of a solid oral dosage form such as a tablet comprising from 100 mg to 400 mg of a compound of Formula (1) provided by the present disclosure to a population of fasted, healthy subjects, the t½ of the mean plasma esketamine concentration can be, for example, from 7 minutes to 11 minutes, from 6 minutes to 10 minutes, or from 7 to 9 minutes.

Following oral administration of a solid oral dosage form such as a tablet comprising from 100 mg to 400 mg of a compound of Formula (1) provided by the present disclosure to a population of fasted, healthy subjects, the t½ of the mean plasma noresketamine concentration can be, for example, from 5.0 minutes to 12.0 minutes from 6.0 minutes to 11.0 minutes, or from 9.0 minutes to 11.0 minutes.

Following oral administration of a solid oral dosage form such as a tablet comprising from 100 mg to 400 mg of a compound of Formula (1) provided by the present disclosure to a population of fasted, healthy subjects, the mean plasma esketamine AUC0-inf can be, for example, from 50 hr×ng/ mL to 300 hr×ng/mL, from 100 hr×ng/mL to 250 hr×ng/mL, or from 150 hr×ng/mL to 200 hr×ng/mL.

Following oral administration of a solid oral dosage form such as a tablet comprising from 100 mg to 400 mg of a compound of Formula (1) provided by the present disclosure to a population of fasted, healthy subjects, the mean plasma esketamine AUC0-inf can be, for example, greater than 50 hr×ng/mL, greater than 100 hr×ng/mL, greater than 150 hr×ng/mL, greater than 200 hr×ng/mL, or greater than 250 hr×ng/mL.

Following oral administration of a solid oral dosage form such as a tablet comprising from 100 mg to 400 mg of a compound of Formula (1) provided by the present disclosure to a population of fasted, healthy subjects, the mean plasma noresketamine AUC0-inf can be, for example, from 500 hr×ng/mL to 3,500 hr×ng/mL, from 1,000 hr×ng/mL to 3,000 hr×ng/mL, or from 1,500 hr×ng/mL to 2,500 hr×ng/mL.

Following oral administration of a solid oral dosage form such as a tablet comprising from 100 mg to 400 mg of a compound of Formula (1) provided by the present disclosure to a population of fasted, healthy subjects, the mean plasma noresketamine AUC0-inf can be, for example, greater than 500 hr×ng/mL, greater than 1,000 hr×ng/mL, greater than 1,500 hr×ng/mL, greater than 2,000 hr×ng/mL, greater than 2,500 hr×ng/mL, greater than 3,000 hr×ng/mL, or greater than 3,500 hr×ng/mL.

Following oral administration of a solid oral dosage form such as a tablet comprising from 100 mg to 400 mg of a compound of Formula (1) provided by the present disclosure to a population of fasted, healthy subjects, the mean plasma esketamine $AUC_{0-12}$ can be, for example, from 20 hr×ng/mL to 300 hr×ng/mL, from 50 hr×ng/mL to 200 hr×ng/mL, or from 100 hr×ng/mL to 150 hr×ng/mL.

Following oral administration of a solid oral dosage form such as a tablet comprising from 100 mg to 400 mg of a compound of Formula (1) provided by the present disclosure to a population of fasted, healthy subjects, the mean plasma esketamine AUC0-12 can be, for example, greater than 20 hr×ng/mL, greater than 50 hr×ng/mL, greater than 100 hr×ng/mL, greater than 150 hr×ng/mL, or greater than 200 hr×ng/mL.

Following oral administration of a solid oral dosage form such as a tablet comprising from 100 mg to 400 mg of a compound of Formula (1) provided by the present disclosure to a population of fasted, healthy subjects, the mean plasma noresketamine AUC0-12h can be, for example, from 200 hr×ng/mL to 2,500 hr×ng/mL, from 300 hr×ng/mL to 2,000 hr×ng/mL, or from 500 hr×ng/mL to 1,500 hr×ng/mL.

Following oral administration of a solid oral dosage form such as a tablet comprising from 100 mg to 400 mg of a compound of Formula (1) provided by the present disclosure to a population of fasted, healthy subjects, the mean plasma noresketamine AUC0-12h can be, for example, greater than 200, greater than 500 hr×ng/mL, greater than 1,000 hr×ng/mL, greater than 1,500 hr×ng/mL, greater than 2,000 hr×ng/mL, or greater than 2,500 hr×ng/mL.

Following oral administration of a solid oral dosage form such as a tablet comprising from 100 mg to 400 mg of a compound of Formula (1) provided by the present disclosure to a population of fasted, healthy subjects, the mean plasma esketamine Cmax/Cave(0-12h) can be, for example, from 1.0 to 4.0, from 1.4 to 3.6, from 1.8 to 3.2, or from 2.2 to 3.0.

Following oral administration of a solid oral dosage form such as a tablet comprising from 100 mg to 400 mg a compound of Formula (1) provided by the present disclosure to a population of fasted, healthy subjects, the mean plasma noresketamine Cmax/Cave(0-12h) can be, for example, from, 1.0 to 2.2, from 1.2 to 2.0, or from 1.4 to 1.8.

Following oral administration of a solid oral dosage form such as a tablet comprising from 100 mg to 400 mg of a compound of Formula (1) provided by the present disclosure to a population of fasted, healthy subjects, the mean plasma esketamine Cmax/Cave(0-12h) can be, for example, less than 4.0, less than 3.5, less than 3.0, less than 2.5, or less than 2.

Following oral administration of a solid oral dosage form such as a tablet comprising from 100 mg to 400 mg a compound of Formula (1) provided by the present disclosure to a population of fasted, healthy subjects, the mean plasma noresketamine Cmax/Cave(0-12h) can be, for example, less than 2.5, less than 2.0, or less than 1.5.

Oral dosage forms such as tablet dosage forms provided by the present disclosure can provide a dose-proportional amount of esketamine and noresketamine in the blood of a patient.

Oral dosage forms such as tablet dosage forms provided by the present disclosure can provide a dose-proportional amount of esketamine in the blood of a patient such as from 10 hr×ng/mL to 1,000 hr×ng/mL, from 20 hr×ng/mL to 800 hr×ng/mL, or from 50 hr×ng/mL to 600 hr×ng/mL esketamine.

Oral dosage forms such as tablet dosage forms provided by the present disclosure can provide a dose-proportional amount of noresketamine in the blood of a patient such as from 10 hr×ng/mL to 10,000 hr×ng/mL, from 50 hr×ng/mL to 8,000 hr×ng/mL, or from 100 hr×ng/mL to 6,000 hr×ng/mL noresketamine.

A pharmaceutical composition and oral dosage form provided by the present disclosure can be used to treat a disease known to be treated by ketamine or determined to be treated by ketamine.

A pharmaceutical composition and oral dosage form provided by the present disclosure can be used to treat a disease known to be or determined to be treated by ketamine and one or more additional therapeutic agents.

For example, a pharmaceutical composition and oral dosage form provided by the present disclosure can be used to treat a neurological disease, a psychiatric disease, or pain.

A pharmaceutical composition and oral dosage form provided by the present disclosure can be used to treat a neurological disease such as a neurological disease of the central nervous system.

Examples of suitable neurological diseases include Alzheimer's disease; amyotrophic lateral sclerosis; back pain; Bell's palsy; birth defects of the brain and spinal cord; brain aneurysm; brain injury; brain tumor; cerebral palsy; chronic fatigue syndrome; concussion; dementia; disk disease of the neck and lower back; dizziness; dystonia; epilepsy; Guillain-Barré syndrome; cluster headache; tension headache; migraine; motor neuron disease amyotrophic lateral sclerosis; multiple sclerosis; muscular dystrophy; neuralgia; neurofibromatosis; neuropathy; neuromuscular and related diseases; Parkinson's disease; progressive supranuclear palsy; psychiatric conditions such as severe depression, obsessive-compulsive disorder; sciatica; scoliosis; seizures; shingles; spinal cord injury; spinal deformity; spinal disorders; spine tumor; stroke; traumatic brain injury; and vertigo.

A pharmaceutical composition and oral dosage form provided by the present disclosure can be used to treat a psychiatric disease.

Example of suitable psychiatric diseases include alcohol or substance use disorder; anxiety disorders including generalized anxiety disorder, panic disorder, phobias, and social anxiety disorder; adult attention deficit/hyperactivity disorder; bipolar disorder including major depressive episode, hypomanic episode, manic episode, and mixed specifier (formerly mixed episode); depression including postpartum depression and seasonal affective disorder; eating disorders; obsessive-compulsive disorder; opioid use disorder symptoms; posttraumatic stress disorder; schizophrenia; dissociative disorders; feeding and eating disorders; sexual and paraphilic disorders; sleep and wake disorders; childhood mental disorders including autism spectrum disorder such as Asperger's disorder, autistic disorder, and Rett's disorder, attention deficit/hyperactivity disorder, and autism; personality disorders including antisocial personality disorder, avoidant personality disorder, borderline personality disorder, dependent personality disorder, histrionic personality disorder, multiple personality disorder, dissociative identity disorder, narcissistic personality disorder, obsessive-compulsive personality disorder, paranoid personality disorder, schizoid personality disorder, and schizotypal personality disorder; and other mental disorders including acute stress disorder, Alzheimer's disease, Parkinson's disease, and psychotic disorder.

A psychiatric disease can be selected from an alcohol abuse disorder, a substance abuse disorder, an anxiety disorder, an adult attention deficit/hyperactivity disorder, a bipolar disorder, an obsessive-compulsive disorder, an opioid use disorder, posttraumatic stress disorder, schizophrenia, a dissociative disorder, a feeding and eating disorder, a sexual and paraphilic disorder, a sleep and wake disorder, a childhood mental disorder, and a personality disorder.

A psychiatric disease can be selected from a mood disorder, a substance abuse disorder and suicidal ideation.

A psychiatric disease can be a mood disorder selected from post-traumatic stress syndrome, anxiety, bipolar disorder, and obsessive-compulsive disorder.

A pharmaceutical composition and oral dosage form provided by the present disclosure can be administered with another drug known to be useful in treating major depressive disorder.

Examples of drugs known to be useful in treating major depressive disorder include selective serotonin reuptake inhibitors such as citalopram, escitalopram, and sertraline, and antidepressants such as bupropion, mirtazapine, imipramine, and nortriptyline; brexpiprazole, brintellix, budeprion, buproban, bupropion, citalopram, duloxetine, desvenlafaxine, venlafaxine, escitalopram, luomilnacipran, fluoxetine, milnacipran, mirtazapine, nefazodone, olanzapine, tranylcypromine, paroxetine, paroxetine mesylate, and trazodone.

A pharmaceutical composition and oral dosage form provided by the present disclosure can be used to treat pain.

Examples of pain include acute pain, addiction, advanced prostate cancer, AIDs-related pain, ankylosing spondylitis, arachnoiditis, arthritis, arthrofibrosis, ataxic cerebral palsy, autoimmune atrophic gastritis, autoimmune diseases, avascular necrosis, back pain, Bechet's disease (syndrome), breakthrough pain, burning mouth syndrome, bursitis, cerebral autosomal dominant arteriopathy, cancer pain, carpal tunnel, cauda equina syndrome, central pain syndrome, cerebral palsy, cerebrospinal fluid leaks, cervical stenosis, Charcot-Marie-Tooth disease, chronic fatigue syndrome, chronic functional abdominal pain, chronic pain, chronic pancreatitis, coccyx, collapsed lung (pneumothorax), complementary and alternative medicine, complex regional pain syndrome, corneal neuropathic pain, Crohn's disease, degenerative disc disease, dependence (physical), depression, Dercum's disease, dermatomyositis, diabetic peripheral neuropathy, dystonia, Ehlers-Danlos syndrome, endometriosis, eosinophilia-myalgia syndrome, erythromelalgia, failed back surgery syndrome, fibromyalgia, gout, growing pains, headaches, herniated disc, hydrocephalus, intercostal neuralgia, interstitial cystitis, irritable bowel syndrome, juvenile dermatomyositis, knee injury, leg pain, loin pain-hematuria syndrome, lupus, Lyme disease, medullary sponge kidney, meralgia paresthetica, mesothelioma, migraine, mitochondrial disorders, multiple sclerosis, musculoskeletal pain, myofascial pain, myositis, neck pain, neuropathic pain, NSAIDs, occipital neuralgia, osteoarthritis, Paget's disease, parsonage turner syndrome, patient rights, pelvic pain, peripheral neuropathy, phantom limb pain, pinched nerve, polycystic kidney disease, polymyalgia rheumatica, polymyositis, porphyria, post herniorrhaphy pain syndrome, post mastectomy pain syndrome, post stroke pain, post thoracotomy pain syndrome, postherpetic neuralgia (shingles), post-polio health international, post-polio syndrome, post-traumatic stress disorder, primary lateral sclerosis, psoriatic arthritis, pudendal neuralgia, radiculopathy, Raynaud's disease, restless leg syndrome, rheumatoid arthritis, sacroiliac joint dysfunction, sarcoidosis, Scheuermann's kyphosis disease, sciatica, scoliosis, shingles (herpes zoster), sickle cell, Sjogren's syndrome, sleep apnea, spasmodic torticollis, sphincter of Oddi dysfunction, spinal cerebellum ataxia, spinal cord injury, spinal stenosis, syringomyelia, Tarlov cysts, tethered cord syndrome, thoracic outlet syndrome, TMJ, tolerance, transverse myelitis, trigeminal neuralgia, trigger points, ulcerative colitis, vascular pain, vulvodynia, and whiplash.

Ketamine is an NMDA (N-methyl-D-aspartate) receptor antagonist. Thus, a compound provided by the present disclosure which, following oral administration, releases ketamine into the systemic circulation can be useful in treating diseases for which ketamine and other NMDA receptor antagonists are useful in treating.

NMDA receptor antagonists are known to be useful in treating or are believed to be useful in treating, for example, acute pain, acute traumatic pain, alcohol use disorder, Alzheimer's disease, anxiety disorders, anxious depression, autism spectrum disorder, bipolar depression, bipolar I disorder, bipolar II disorder, chronic pain, cancer pain, cognitive symptom, cortical spreading depolarization, cortical spreading depression, violent/aggressive behavior, depression, fracture pain, head and neck cancer, headache, Huntington's disease, intractable pain, major depression disorder, migraine, mood disorders, neuropathic pain, obsessive compulsive disorder, obstructive sleep apnea syndrome, pancreatic cancer pain, Parkinson's disease, perinatal depression, post-operative cognitive dysfunction, postoperative pain, postpartum depression, post-traumatic stress disorder, pressure ulcer, psychotic-like symptoms, refractory cancer pain, Rett syndrome, schizophrenia, sleep apnea, social anxiety disorder, stress disorders, subarachnoid hemorrhage, substance use disorders, suicide, suicidal ideation, systemic lupus erythematosus, traumatic brain injury, treatment resistant depression, and unipolar depression.

A pharmaceutical composition and oral dosage form provided by the present disclosure can be sued to treat an anxiety disorder, a seasonal affective disorder, mania, a bipolar disorder, obsessive-compulsive disorder, insomnia and fatigue resulting from jet lag, mental schizophrenia, seizure, panic attack, melancholia, alcohol addiction, drug addiction, alcoholism, substance abuse, drug addiction withdrawal symptoms, insomnia, a psychotic disorder, epilepsy, somnipathy, sleep disorder, sleep apnea syndrome, a mandatory eating disorder, fibromyalgia, stress, obesity, Parkinson's disease, a cognitive disorder, a memory disorder, premenstrual tension syndrome, a migraine headache, memory loss, Alzheimer silent disease or a disorder related to normal or pathological aging.

A pharmaceutical composition or oral dosage form provided by the present disclosure can be used to treat a disease for which the etiology of the disease is associated with the NMDA receptor.

A pharmaceutical composition or oral dosage form provided by the present disclosure can be administered to a patient in combination with a drug known to be useful in treating a side effective of ketamine. Examples of side effects of ketamine include sleepiness, dizziness, poor coordination, blurred vision, dissociative symptom, impairment of attention and concentration, anxiety, and confusion.

Drugs known to be useful in treating a side effect of ketamine include, for example, clonidine.

Methods provided by the present disclosure include providing a therapeutically effective amount of ketamine in the systemic circulation of a patient comprising administering to a pharmaceutical composition and oral dosage form provided by the present disclosure.

A pharmaceutical composition and oral dosage form provided by the present disclosure can be administered orally.

A pharmaceutical composition and oral dosage form provided by the present disclosure, when orally administered, provide an enhanced oral bioavailability of ketamine compared to the oral bioavailability of orally administered ketamine.

In humans, orally administered (50 mg tablet) (S)-ketamine and (R)-ketamine has an oral bioavailability of about 18% with a CMX of about 41 ng/mL, a $T_{max}$ of about 31 min, and an $AUC_{0-inf}$ ng×h/mL. Yanagihara et al., *Biopharmaceutics & Drug Disposition*, 24, p. 37-43 (2003).

For example, a compound of Formula (1) can exhibit a ketamine oral bioavailability (% F) of at least 10%, at least 20%, at least 30%, at least 40%, at least 50%, or at least 60%. A compound of Formula (1) can provide a ketamine oral availability, for example, from 5% to 90% from, 10% to 80%, from 15% to 70%, or from 20% to 60%.

Single and multiple doses of ketamine for treating diseases such as depression can range, for example from 50 mg to 300 mg per day.

A pharmaceutical composition and oral dosage form provided by the present disclosure can be administered in conjunction with an agent known or believed to be effective in treating the disease being treated with ketamine.

For example, a pharmaceutical composition and oral dosage form provided by the present disclosure can be co-administered with other NMDA receptor antagonists including, for example, competitive antagonists such as AP5 (APV, R-2-amino-5-phosphonopentanoate), AP7 (2-amino-7-phosphonoheptanoic acid), copene (3-[(R)-2-carboxypiperazin-4-yl]-prop-2-enyl-1-phosphonic acid), selfotel, and aspartame; uncompetitive channel blockers including minocycline, amantadine, atomoxetine, AZD6765, agmatine, chloroform, dextrallorphan, dextromethorphan, dextrorphan, diphenidine, dizocilpine (MK-801), ethanol, eticyclidine, gacyclidine, ketamine, magnesium, memantine, methoxetamine, nitromemantine, nitrous oxide, PD-137889, phencyclidine, rolicyclidine, tenocyclidine, methoxydine, tiletamine, neramexane, eliprodil, etoxadrol, dexoxadrol, WMS-2539, NEFA, remacemide, delucemine, and 8A-PDHQ, non-competitive antagonists such as aptiganel, HU-211, huperzine A, ibogaine, remacemide, rhynchophylline, and gabapentin; glycine antagonists such as apastinel, NRX-1074, 7-chlorokynurenic acid, 4-chlorokynurenine, 5,7-dichlorokynurenic acid, kynurenic acid, TK-40, 1-aminocyclopropanecarboxylic acid, 1-phenylalanine, and xenon; or a combination of any of the foregoing.

A dose of compound of Formula (1) and appropriate dosing intervals may be selected to maintain a sustained therapeutically effective concentration of the compound of ketamine in the blood of a patient, and in certain embodiments, without exceeding a minimum adverse concentration.

A therapeutically effective concentration of ketamine in the blood or plasma of a patient can be less than an amount that causes unacceptable adverse effects including adverse effects to homeostasis. A therapeutically effective concentration of ketamine in the blood or plasma of a patient can be an amount sufficient to restore and/or maintain homeostasis in the patient. For example, following administration of a therapeutically effective dose of a compound of Formula (1), a therapeutically effective amount of ketamine can be maintained for greater than 1 hour, greater than 2 hours, greater than 3 hours, greater than 4 hours, greater than 5 hours, greater than 6 hours, greater than 7 hours, or greater than 8 hours. For example, following administration of a therapeutically effective dose of a compound of Formula (1), a therapeutically effective amount of ketamine can be maintained, for example, from 1 hour to 10 hours, from 2 hours to 8 hours, from 2 hours to 6 hours, or from 2 hours to 4 hours.

A therapeutically effective plasma ketamine concentration of a patient can be, for example, greater than 5 ng/mL, greater than 10 ng/mL, greater than 20 ng/mL, greater than 50 ng/mL, greater than 100 ng/mL, greater than 150 ng/mL, or greater than 200 ng/mL, where the disease or condition, for example, is pain or depression.

A therapeutically effective plasma ketamine concentration for treating, for example, pain or depression can range from 1 ng/mL to 250 ng/mL, form 5 ng/mL to 200 ng/mL, from 10 ng/mL to 175 ng/mL, or from 50 ng/mL to 175 ng/mL.

A therapeutically effective $AUC_{0-inf}$ plasma ketamine concentration for treating, for example, pain or depression can range, for example, from 10 ng×h/mL to 500 ng×h/mL, from 50 ng×h/mL to 400 ng×h/mL, or from 100 ng×h/mL to 300 ng×h/mL.

A dose of a compound of Formula (1) for treating a disease such as, for example, pain or depression, can range from 0.1 mg-equivalents ketamine/kg to 3 mg-equivalents/kg, from 0.5 mg-equivalents/kg to 2.5 mg/kg, or from 1 mg-equivalents/kg to 2 mg/kg. A dose of a compound of Formula (1) for treating a disease such as, for example, pain or depression, can be greater than 0.1 mg-equivalents ketamine/kg, greater than 0.5 mg-equivalents/kg, greater than 1 mg-equivalents/kg, or greater than 2 mg-equivalents/kg.

A dose of a compound of Formula (1) for treating a disease such as, for example, pain or depression, can range from 10 mg-equivalents ketamine to 250 mg-equivalents, from 20 mg-equivalents to 200 mg-equivalents, or from 25 mg-equivalents to 100 mg-equivalents.

A dose of a compound of Formula (1) for treating a disease such as, for example, pain or depression can be greater than 10 mg-equivalents ketamine, greater than 25 mg-equivalents, greater than 50 mg-equivalents, greater than 75 mg-equivalents, greater than 100 mg-equivalents, greater than 150 mg-equivalents, greater than 200 mg-equivalents, or greater than 250 mg-equivalents.

An oral dosage form provided by the present disclosure can be administered at appropriate intervals for an appropriate duration to treat a disease.

An oral dosage form can be determined, for example, once per day, twice per day, three times per day, or four times per day.

An oral dosage form can be administered, for example, for from 1 to 7 days, for from 1 to 8 weeks, or from 1 month to 3 months.

A dosing interval and the dose administered can vary during the treatment.

A pharmaceutical composition and oral dosage form provided by the present disclosure can be included in a kit that may be used to administer the pharmaceutical composition or oral dosage form to a patient for therapeutic purposes. A kit may include a pharmaceutical composition or oral dosage form comprising a compound of Formula (1) suitable for administration to a patient and instructions for administering the pharmaceutical composition or oral dosage form to the patient. A kit for use in treating a disease such as a psychiatric disease, a neurological disease or pain in a patient can comprise a pharmaceutical composition or oral dosage form provided by the present disclosure, a pharmaceutically acceptable vehicle for administering the pharmaceutical composition or oral dosage form, and instructions for administering the pharmaceutical composition or oral dosage form to a patient. Instructions supplied with a kit may be printed and/or supplied, for example, as an electronic-readable medium, a video cassette, an audiotape, a flash memory device, or may be published on an internet web site or distributed to a patient and/or health care provider as an electronic communication.

Aspects of the Invention

The invention is further defined by the following aspects:

Aspect 1. A pharmaceutical composition comprising:
granules comprising a compound of Formula (1):

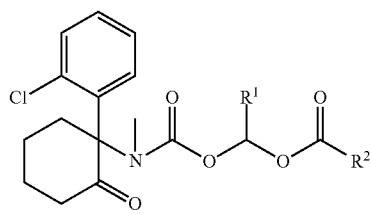
(1)

or a pharmaceutically acceptable salt thereof, wherein,
$R^1$ is selected from hydrogen and $C_{1-6}$ alkyl; and
$R^2$ is selected from a moiety of Formula (2), a moiety of Formula (3), a moiety of Formula (4), and a moiety of Formula (5):

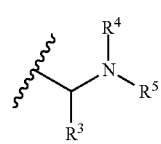
(2)

-continued

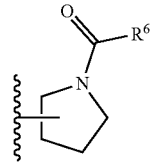
(3)

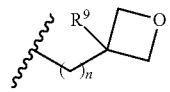
(4)

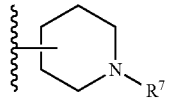
(5)

wherein,
$R^3$ is selected from hydrogen, $C_{1-6}$ alkyl, $C_{7-12}$ alkylarene, and substituted $C_{7-12}$ alkylarene;
$R^4$ is selected from hydrogen and $C_{1-6}$ alkyl;
$R^5$ is selected from hydrogen, $C_{1-6}$ alkyl, —C(=O)—$R^{10}$, and —C(=O)—O—$R^{10}$, wherein $R^{10}$ is selected from $C_{1-6}$ alkyl, $C_{3-6}$ cycloalkyl, and —$CF_3$;
$R^6$ is selected from $C_{1-6}$ alkyl and $C_{1-6}$ alkoxy;
n is an integer from 0 to 3;
$R^7$ is selected from hydrogen, $C_{1-6}$ alkyl, —C(=O)—$R^{11}$, and —C(=O)—O—$R^{10}$, wherein,
$R^{10}$ is selected from $C_{1-6}$ alkyl and $C_{3-6}$ cycloalkyl; and
$R^{11}$ is selected from —$NH_2$, —$CF_3$, $C_{1-6}$ alkyl, and $C_{3-6}$ cycloalkyl; and
$R^9$ is selected from hydrogen and $C_{1-3}$ alkyl;
a controlled release polymer; and
an anionic sulfate/sulfonate surfactant.

Aspect 2. The composition of aspect 1, wherein the compound of Formula (1) is selected from 1-((((S)-1-(2-chlorophenyl)-2-oxocyclohexyl)(methyl)carbamoyl)oxy) ethyl acetylglycinate (3) and 1-((((R)-1-(2-chlorophenyl)-2-oxocyclohexyl)(methyl)carbamoyl)oxy)ethyl acetylglycinate (62):

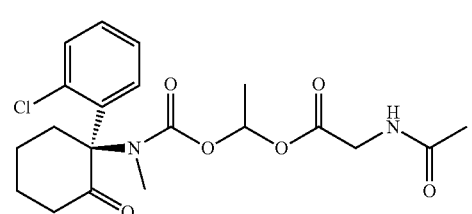
(3)

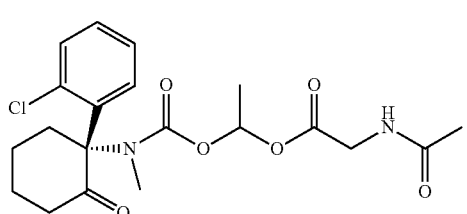
(62)

or a pharmaceutically acceptable salt of any of the foregoing.

Aspect 3. The composition of aspect 1, wherein the compound of Formula (1) is selected from 1-((((S)-1-(2-chlorophenyl)-2-oxocyclohexyl)(methyl)carbamoyl)oxy)ethyl 2-(3-methyloxetan-3-yl)acetate (6) and 1-((((R)-1-(2-chlorophenyl)-2-oxocyclohexyl)(methyl)carbamoyl)oxy)ethyl 2-(3-methyloxetan-3-yl)acetate (63):

(6)

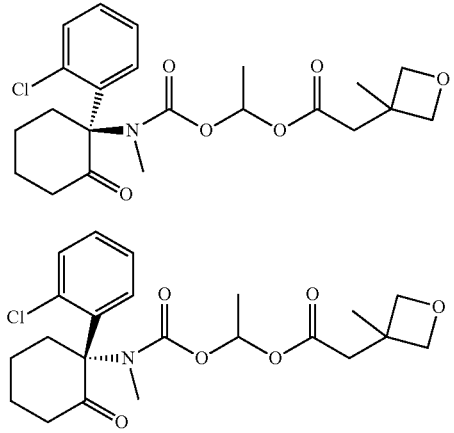

(63)

or a pharmaceutically acceptable salt of any of the foregoing.

Aspect 4. The composition of aspect 1, wherein the compound of Formula (1) is selected from (S)-(((1-(2-chlorophenyl)-2-oxocyclohexyl)(methyl)carbamoyl)oxy)methyl 2-(3-methyloxetan-3-yl)acetate (22) and (R)-(((1-(2-chlorophenyl)-2-oxocyclohexyl)(methyl)carbamoyl)oxy)methyl 2-(3-methyloxetan-3-yl)acetate (66):

(22)

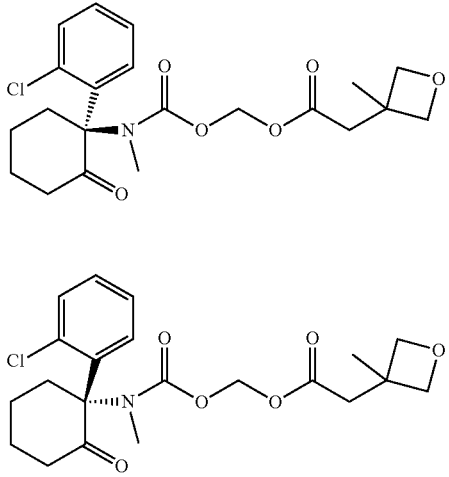

(66)

or a pharmaceutically acceptable salt of any of the foregoing.

Aspect 5. The composition of aspect 1, wherein the compound of Formula (1) is selected from ((((S)-1-(2-chlorophenyl)-2-oxocyclohexyl)(methyl)carbamoyl)oxy)methyl dimethyl-L-valinate (39) and ((((R)-1-(2-chlorophenyl)-2-oxocyclohexyl)(methyl)carbamoyl)oxy)methyl dimethyl-L-valinate (65):

(39)

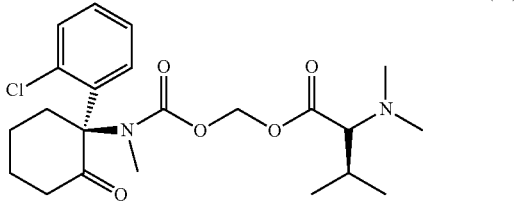

(65)

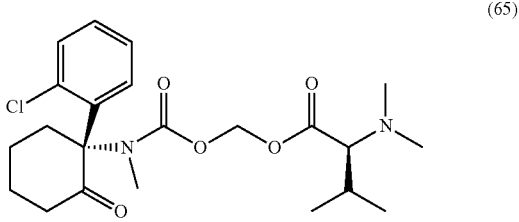

or a pharmaceutically acceptable salt of any of the foregoing.

Aspect 6. The composition of aspect 1, wherein the compound of Formula (1) is selected from 1-((((S)-1-(2-chlorophenyl)-2-oxocyclohexyl)(methyl)carbamoyl)oxy)ethyl acetyl-L-leucinate (58) and 1-((((R)-1-(2-chlorophenyl)-2-oxocyclohexyl)(methyl)carbamoyl)oxy)ethyl acetyl-L-leucinate (71):

(58)

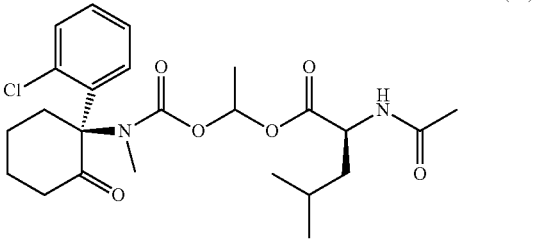

(71)

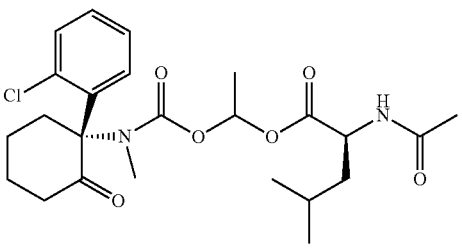

or a pharmaceutically acceptable salt of any of the foregoing.

Aspect 7. The composition of aspect 1, wherein the compound of Formula (1) is selected from 1-((((S)-1-(2-chlorophenyl)-2-oxocyclohexyl)(methyl)carbamoyl)oxy)ethyl acetyl-L-alloisoleucinate (59) and 1-((((R)-1-(2-chlorophenyl)-2-oxocyclohexyl)(methyl)carbamoyl)oxy)ethyl acetyl-L-alloisoleucinate (72):

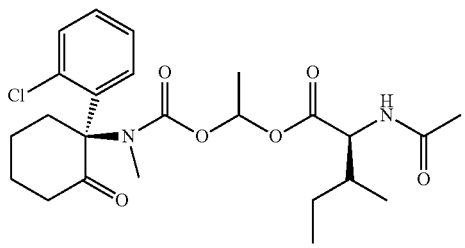
(59)

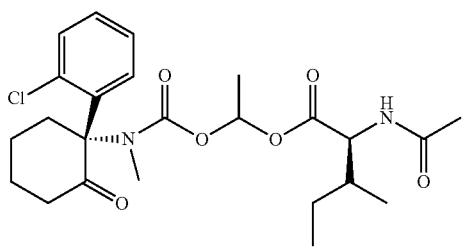
(72)

or a pharmaceutically acceptable salt of any of the foregoing.

Aspect 8. The composition of aspect 1, wherein the compound of Formula (1) is ((((S)-1-(2-chlorophenyl)-2-oxocyclohexyl)(methyl)carbamoyl)oxy)methyl dimethyl-L-valinate (39) or a pharmaceutically acceptable salt thereof.

Aspect 9. The composition of any one of aspects 1 to 8, wherein the compound of Formula (1) comprises the hydrochloride salt.

Aspect 10. The composition of any one of aspects 1 to 8, wherein the compound of Formula (1) comprises the free base.

Aspect 11. The composition of any one of aspects 1 to 10, wherein the compound of Formula (1) or a pharmaceutically acceptable salt thereof has a higher solubility in 0.1N hydrochloride than in a 50 mM acetate buffer at pH 4.5.

Aspect 12. The composition of any one of aspects 1 to 11, wherein the granules comprise greater than 95 wt % of the compound of Formula (1) or a pharmaceutically acceptable salt thereof, wherein wt % is based on the total weight of the granules.

Aspect 13. The composition of any one of aspects 1 to 12, wherein the granules comprise a granule binder.

Aspect 14. The composition of aspect 13, wherein the granule binder comprises hydroxypropylmethyl cellulose, hydroxypropylcellulose, polyvinylpyrrolidone, or a combination of any of the foregoing.

Aspect 15. The composition of any one of aspects 13 to 14, wherein the granules comprise from 0.5 wt % to 5.0 wt % of the granule binder, wherein wt % is based on the total weight of the granules.

Aspect 16. The composition of any one of aspects 1 to 15, wherein the granules comprise:
from 97 wt % to 99 wt % of the compound of Formula (1) or a pharmaceutically acceptable salt thereof, and
from 1 wt % to 3 wt % of a granule binder,
wherein wt % is based on the total weight of the granules.

Aspect 17. The composition of any one of aspects 1 to 16, wherein the granules have a mean average diameter from 100 µm to 500 µm.

Aspect 18. The composition of any one of aspects 1 to 17, wherein the composition comprises from 35 wt % to 55 wt % of the granules, wherein wt % is based on the total weight of the composition.

Aspect 19. The composition of any one of aspects 1 to 18, wherein the controlled release polymer comprises carbomer copolymers, shellac, carbomer homopolymers, hypromellose (hydroxypropyl methylcellulose) polymers, carbomer interpolymers, carboxymethylcellulose sodium, carrageenan, cellaburate, ethylcellulose, glyceryl monooleate, pregelatinized modified starch, glyceryl monostearate, guar gum, hydroxypropyl betadex, hydroxypropyl cellulose, polyethylene oxide, polyvinyl acetate dispersion, sodium alginate, pregelatinized starch, xanthan gum, alginic acid, ethylacrylate/methyl methacrylate copolymers, acrylic acid/allyl sucrose polymers, acrylic acid/allyl pentaerythritol polymers, acrylic acid/alkyl acrylate/allyl pentaerythritol copolymers, or a combination of any of the foregoing.

Aspect 20. The composition of any one of aspects 1 to 19, wherein the controlled release polymer comprises hydroxypropylmethyl cellulose.

Aspect 21. The composition of aspect 20, wherein the hydroxypropylmethyl cellulose is characterized by a weight average molecular weight from 900,000 Daltons to 1,100,000 Daltons, a methoxyl content from 20% to 24%; a pH at 25° C. from 5 to 8; a hydroxypropyl content 7% to 12%; a viscosity from 75,000 mPa-s (cP) to 140,000 mPa-s (cP) of a 2% aqueous solution at 20° C.

Aspect 22. The composition of any one of aspects 20 to 21, wherein the hydroxypropylmethyl cellulose is characterized by a weight average molecular weight from 300,000 Daltons to 500,000 Daltons, a methoxyl content from 19% to 24%; a pH at 25° C. from 5 to 8; a hydroxypropyl content 7% to 12%; a viscosity from 2,700 mPa-s (cP) to 5,040 mPa-s (cP) of a 2% aqueous solution at 20° C.

Aspect 23. The composition of any one of aspects 20 to 22, wherein the hydroxypropyl methyl cellulose comprises:
from 50 wt % to 80 wt % of a hydroxypropylmethyl cellulose characterized by a weight average molecular weight from 900,000 Daltons to 1,100,000 Daltons; and
from 20 wt % to 50 wt % of a hydroxypropylmethyl cellulose characterized by a weight average molecular weight from 300,000 Daltons to 500,000 Daltons;
wherein wt % is based on the total weight of the hydroxypropylmethyl cellulose.

Aspect 24. The composition of any one of aspects 1 to 23, wherein the composition comprises from 10 wt % to 40 wt % of the controlled release polymer, wherein wt % is based on the total weight of the composition.

Aspect 25. The composition of any one of aspects 1 to 24, wherein the anionic sulfate/sulfonate surfactant is characterized by a critical micelle concentration from 2 g/L to 3 g/L (6.9 mmol/L to 10.4 mmol/L) at 20° C.

Aspect 26. The composition of any one of aspects 1 to 25, wherein the anionic sulfate/sulfonate surfactant comprises sodium lauryl sulfate.

Aspect 27. The composition of aspect 26, wherein the sodium lauryl sulfate is characterized by a critical micelle concentration from 2.2 g/L to 2.5 g/L at 20° C.

Aspect 28. The composition of any one of aspects 1 to 27, wherein the composition comprises from 5 wt % to 15 wt % of the anionic sulfate/sulfonate surfactant, wherein wt % is based on the total weight of the composition.

Aspect 29. The composition of any one of aspects 1 to 28, wherein the composition comprises:
from 30 wt % to 60 wt % of the granules;
from 10 wt % to 40 wt % of the controlled release polymer; and
from 5 wt % to 15 wt % of the anionic sulfate/sulfonate surfactant, wherein wt % is based on the total weight of the composition.

Aspect 30. The composition of any one of aspects 1 to 29, wherein the composition comprises a filler.

Aspect 31. The composition of aspect 30, wherein the filler comprises microcrystalline cellulose.

Aspect 32. The composition of any one of aspects 30 to 31, wherein the composition comprises from 5 wt % to 35 wt % of the filler, where wt % is based on the total weight of the composition.

Aspect 33. The composition of any one of aspects 1 to 32, wherein the composition comprises a lubricant.

Aspect 34. The composition of aspect 33, wherein the lubricant comprises magnesium stearate.

Aspect 35. The composition of any one of aspects 32 to 33, wherein the composition comprises from 0.1 wt % to 1.5 wt % of the lubricant, wherein wt % is based on the total weight of the composition.

Aspect 36. An oral dosage form comprising the composition of any one of aspects 1 to 35.

Aspect 37. The composition of aspect 36, wherein the oral dosage form comprises a solid oral dosage form.

Aspect 38. The composition of aspect 36, wherein the oral dosage from comprises a tablet.

Aspect 39. The oral dosage form of any one of aspects 36 to 38, wherein the oral dosage form comprises from 25 mg to 400 mg of the compound of Formula (1) or a pharmaceutically acceptable salt thereof.

Aspect 40. The oral dosage form of any one of aspects 36 to 39, wherein the oral dosage form exhibits a zero-order release profile over at least six hours of the compound of Formula (1) or a pharmaceutically acceptable salt thereof in a two-stage dissolution medium as determined using a USP I dissolution apparatus with an agitation rate of 100 RPM and at a temperature of 37° C., wherein, the first stage comprises immersing the solid dosage from in 0.1N hydrochloric acid for 1 hour; and the second stage comprises immersing the oral dosage form in a 50 mM acetate buffer at pH 4.5 for the duration.

Aspect 41. The oral dosage form of any one of aspects 36 to 40, wherein the oral dosage form is characterized by a dissolution profile of the compound of Formula (1) or a pharmaceutically acceptable salt thereof in a two-stage dissolution medium as determined using a USP I dissolution apparatus with an agitation rate of 100 RPM and at a temperature of 37° C., wherein, from 20% to 40% of the compound of Formula (1) is released at 2 hours;

from 30% to 50% of the compound of Formula (1) is released at 4 hours;

from 70% to 80% of the compound of Formula (1) is released at 8 hours;

from 80% to 100% of the compound of Formula (1) is released at 12 hours;

from 80% to 100% of the compound of Formula (1) is released at 16 hours;

the first stage comprises immersing the oral dosage from in 0.1N hydrochloric acid for 1 hour;

the second stage comprises immersing the oral dosage from in a 50 mM acetate buffer at pH 4.5 for the duration; and percent (%) is based on the total amount of the compound of Formula (1) or a pharmaceutically acceptable salt thereof in the oral dosage form, Aspect 42. The oral dosage form of any one of aspects 36 to 40, wherein the solid dosage form is characterized by a dissolution profile of the compound of Formula (1) or a pharmaceutically acceptable salt thereof in a two-stage dissolution medium as determined using a USP I dissolution apparatus with an agitation rate of 100 RPM and at a temperature of 37° C., wherein, from 30% to 40%, is of the compound of Formula (1) released at 2 hours;

from 50% to 70% is of the compound of Formula (1) released at 4 hours;

from 70% to 90% is of the compound of Formula (1) released at 8 hours;

greater than 90% is of the compound of Formula (1) released at 12 hours;

the first stage comprises immersing the oral dosage form in 0.1N hydrochloric acid for 1 hour;

the second stage comprises immersing the oral dosage form in a 50 mM acetate buffer at pH 4.5 for the duration; and percent (%) is based on the total amount of the compound of Formula (1) or a pharmaceutically acceptable salt thereof in the oral dosage form.

Aspect 43. The oral dosage form of any one of aspects 36 to 40, wherein the solid dosage form is characterized by a dissolution profile of the compound of Formula (1) or a pharmaceutically acceptable salt thereof in a two-stage dissolution medium as determined using a USP I dissolution apparatus with an agitation rate of 100 RPM and at a temperature of 37° C., wherein, from 15% to 25% is of the compound of Formula (1) released at 2 hours from 20% to 35% is of the compound of Formula (1) released at 4 hours;

from 50% to 60% is of the compound of Formula (1) released at 8 hours;

from 70% to 85% is of the compound of Formula (1) released at 12 hours;

from 80% to 100% is of the compound of Formula (1) released at 16 hours;

the first stage comprises immersing the oral dosage form in 0.1N hydrochloric acid for 1 hour;

the second stage comprises immersing the oral dosage form in a 50 mM acetate buffer at pH 4.5 for the duration; and percent (%) is based on the total amount of the compound of Formula (1) or a pharmaceutically acceptable salt thereof in the oral dosage form.

Aspect 44. The oral dosage form of any one of aspects 36 to 40, wherein the dissolution profile is bioequivalent to the any one of the dissolution profiles shown in FIG. 1.

Aspect 45. A kit comprising the pharmaceutical composition of any one of aspects 1 to 35 or an oral dosage form of any one of aspects 36 to 44.

Aspect 46. A method of treating a disease in a patient comprising orally administering to a patient in need of such treatment a therapeutically effective amount of the pharmaceutical composition of any one of aspects 1 to 35, wherein the disease is selected from a neurological disease, a psychiatric disease, and pain.

Aspect 47. A method of treating a disease in a patient comprising orally administering to a patient in need of such treatment a therapeutically effective amount of the pharmaceutical composition of any one of aspects 1 to 35, wherein the disease is treated by inhibiting NMDA receptors.

Aspect 48. A method of treating a disease in a patient comprising orally administering to a patient in need of such treatment a therapeutically effective amount of the oral dosage form of any one of aspects 36 to 44, wherein the disease is selected from a neurological disease, a psychiatric disease, and pain.

Aspect 49. A method of treating a disease in a patient comprising orally administering to a patient in need of such treatment a therapeutically effective amount of the oral dosage form of any one of aspects 36 to 44, wherein the disease is treated by inhibiting NMDA receptors.

Aspect 50. Use of the pharmaceutical composition of aspect 1 in the manufacture of a medicament for treating a disease in a patient, wherein the disease is selected from a neurological disease, a psychiatric disease, and pain.

Aspect 51. Use of the pharmaceutical composition of any one of aspects 1 to 35 in the manufacture of a medicament for treating a disease in a patient, wherein the disease is treated by inhibiting NMDA receptors.

Aspect 1A. A pharmaceutical composition comprising:
(a) a compound of Formula (1):

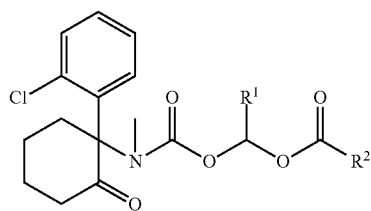

(1)

or a pharmaceutically acceptable salt thereof, wherein,
$R^1$ is selected from hydrogen and $C_{1-6}$ alkyl; and
$R^2$ is selected from a moiety of Formula (2), a moiety of Formula (3), a moiety of Formula (4), and a moiety of Formula (5):

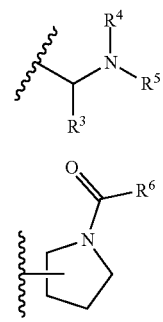

(2)

(3)

(4)

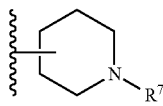

(5)

wherein,
$R^3$ is selected from hydrogen, $C_{1-6}$ alkyl, $C_{7-12}$ alkylarene, and substituted $C_{7-12}$ alkylarene;
$R^4$ is selected from hydrogen and $C_{1-6}$ alkyl;
$R^5$ is selected from hydrogen, $C_{1-6}$ alkyl, —C(=O)—$R^{10}$, and —C(=O)—O—$R^{10}$, wherein $R^{10}$ is selected from $C_{1-6}$ alkyl, $C_{3-6}$ cycloalkyl, and —CF$_3$;
$R^6$ is selected from $C_{1-6}$ alkyl and $C_{1-6}$ alkoxy;
n is an integer from 0 to 3;

$R^7$ is selected from hydrogen, $C_{1-6}$ alkyl, —C(=O)—$R^1$, and —C(=O)—O—$R^{10}$, wherein,
$R^{10}$ is selected from $C_{1-6}$ alkyl and $C_{3-6}$ cycloalkyl; and
$R^{11}$ is selected from —NH$_2$, —CF$_3$, $C_{1-6}$ alkyl, and $C_{3-6}$ cycloalkyl; and
$R^9$ is selected from hydrogen and $C_{1-3}$ alkyl;
(b) a controlled release polymer; and
(c) an anionic sulfate/sulfonate surfactant.

Aspect 2A. The pharmaceutical composition of aspect 1A, wherein the compound of Formula (1) is selected from 1-((((S)-1-(2-chlorophenyl)-2-oxocyclohexyl)(methyl)carbamoyl)oxy)ethyl acetylglycinate (3) and 1-((((R)-1-(2-chlorophenyl)-2-oxocyclohexyl)(methyl)carbamoyl)oxy)ethyl acetylglycinate (62):

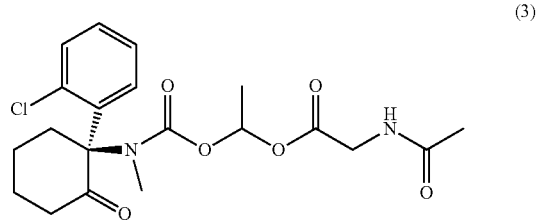

(3)

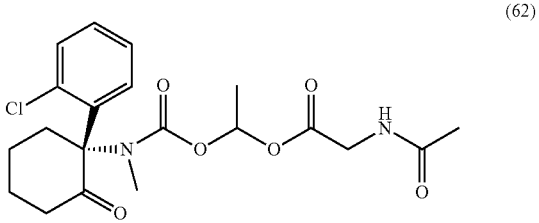

(62)

or a pharmaceutically acceptable salt of any of the foregoing.

Aspect 3A. The pharmaceutical composition of aspect 1A, wherein the compound of Formula (1) is selected from 1-((((S)-1-(2-chlorophenyl)-2-oxocyclohexyl)(methyl)carbamoyl)oxy)ethyl 2-(3-methyloxetan-3-yl)acetate (6) and 1-((((R)-1-(2-chlorophenyl)-2-oxocyclohexyl)(methyl)carbamoyl)oxy)ethyl 2-(3-methyloxetan-3-yl)acetate (63):

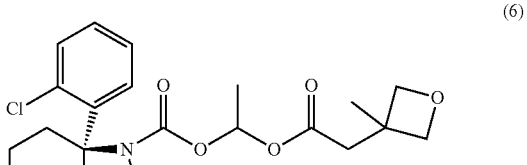

(6)

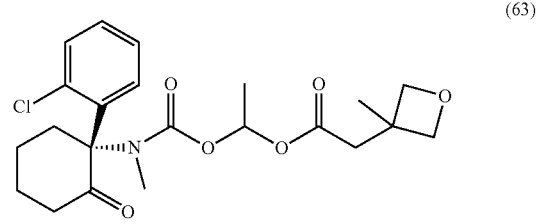

(63)

or a pharmaceutically acceptable salt of any of the foregoing.

Aspect 4A. The pharmaceutical composition of aspect 1A, wherein the compound of Formula (1) is selected from (S)-(((1-(2-chlorophenyl)-2-oxocyclohexyl)(methyl)carbamoyl)oxy)methyl 2-(3-methyloxetan-3-yl)acetate (22) and (R)-(((1-(2-chlorophenyl)-2-oxocyclohexyl)(methyl)carbamoyl)oxy)methyl 2-(3-methyloxetan-3-yl)acetate (66):

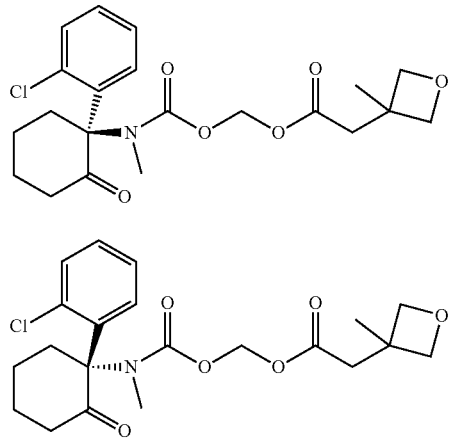

(22)

(66)

or a pharmaceutically acceptable salt of any of the foregoing.

Aspect 5A. The pharmaceutical composition of aspect 1A, wherein the compound of Formula (1) is selected from (((((S)-1-(2-chlorophenyl)-2-oxocyclohexyl)(methyl)carbamoyl)oxy)methyl dimethyl-L-valinate (39) and ((((R)-1-(2-chlorophenyl)-2-oxocyclohexyl)(methyl)carbamoyl)oxy) methyl dimethyl-L-valinate (65):

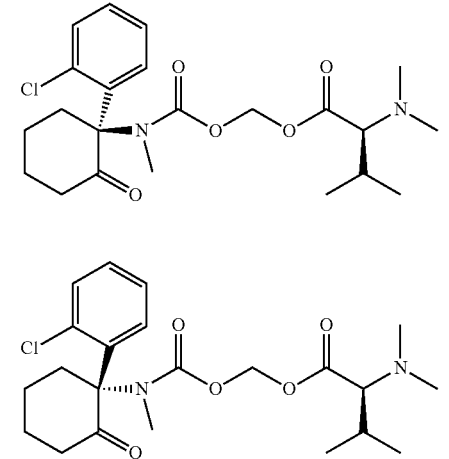

(39)

(65)

or a pharmaceutically acceptable salt of any of the foregoing.

Aspect 6A. The pharmaceutical composition of aspect 1A, wherein the compound of Formula (1) is selected from 1-(((((S)-1-(2-chlorophenyl)-2-oxocyclohexyl)(methyl)carbamoyl)oxy)ethyl acetyl-L-leucinate (58) and 1-(((((R)-1-(2-chlorophenyl)-2-oxocyclohexyl)(methyl)carbamoyl)oxy) ethyl acetyl-L-leucinate (71):

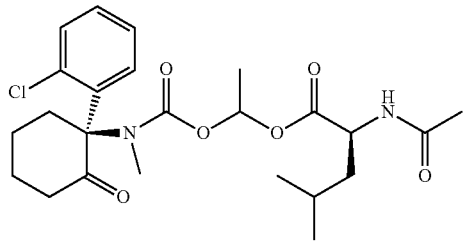

(58)

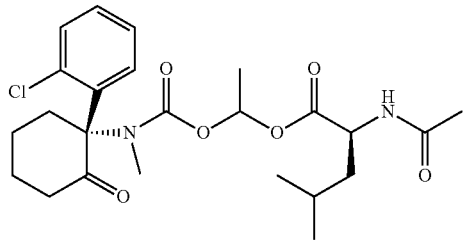

(71)

or a pharmaceutically acceptable salt of any of the foregoing.

Aspect 7A. The pharmaceutical composition of aspect 1A, wherein the compound of Formula (1) is selected from 1-(((((S)-1-(2-chlorophenyl)-2-oxocyclohexyl)(methyl)carbamoyl)oxy)ethyl acetyl-L-alloisoleucinate (59) and 1-(((((R)-1-(2-chlorophenyl)-2-oxocyclohexyl)(methyl)carbamoyl)oxy)ethyl acetyl-L-alloisoleucinate (72):

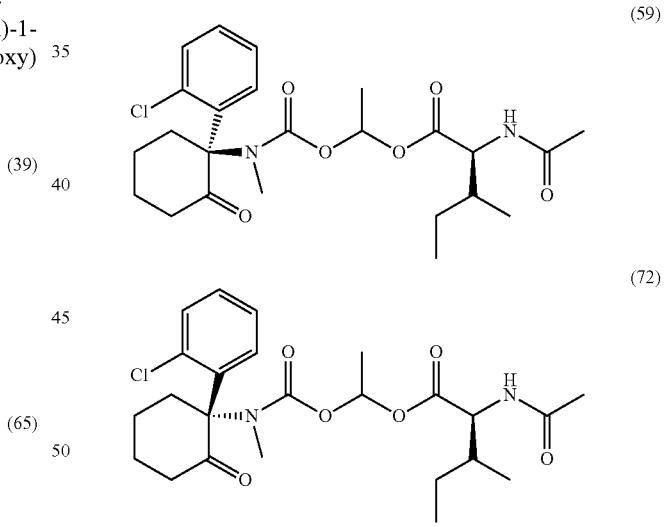

(59)

(72)

or a pharmaceutically acceptable salt of any of the foregoing.

Aspect 8A. The pharmaceutical composition of aspect 1A, wherein the compound of Formula (1) is ((((S)-1-(2-chlorophenyl)-2-oxocyclohexyl)(methyl)carbamoyl)oxy) methyl dimethyl-L-valinate (39) or a pharmaceutically acceptable salt thereof.

Aspect 9A. The pharmaceutical composition of any one of aspects 1A to 8A, wherein the compound of Formula (1) comprises the hydrochloride salt.

Aspect 10A. The pharmaceutical composition of any one of aspects 1A to 8A, wherein the compound of Formula (1) comprises the free base.

Aspect 11A. The pharmaceutical composition of any one of aspects 1A to 10A, wherein the compound of Formula (1) or a pharmaceutically acceptable salt thereof has a higher solubility in 0.1N hydrochloride than in a 50 mM acetate buffer at pH 4.5.

Aspect 12A. The pharmaceutical composition of any one of aspects 1A to 11A, wherein the pharmaceutical composition comprises granules, wherein the granules comprise greater than 95 wt % of the compound of Formula (1) or a pharmaceutically acceptable salt thereof, wherein wt % is based on the total weight of the granules.

Aspect 13A. The pharmaceutical composition of any one of aspects 12A to 12A, wherein the granules comprise a granule binder.

Aspect 14A. The pharmaceutical composition of aspect 13A, wherein the granule binder comprises hydroxypropylmethyl cellulose, hydroxypropylcellulose, polyvinylpyrrolidone, or a combination of any of the foregoing.

Aspect 15A. The pharmaceutical composition of aspect 14A, wherein the granule binder comprises hydroxypropylmethyl cellulose.

Aspect 16A. The pharmaceutical composition of aspect 15A, wherein the hydroxypropylmethyl cellulose is characterized by as 2910 substitution type and a viscosity of 3 mPaxsec in a 2 wt % aqueous solution at 20° C.

Aspect 17A. The pharmaceutical composition of any one of aspects 12A to 16A, wherein the granules comprise from 0.5 wt % to 5.0 wt % of the granule binder, wherein wt % is based on the total weight of the granules.

Aspect 18A. The pharmaceutical composition of any one of aspects 12A to 17A, wherein the granules comprise:
from 97 wt % to 99 wt % of the compound of Formula (1) or a pharmaceutically acceptable salt thereof, and
from 1 wt % to 3 wt % of the granule binder, wherein wt % is based on the total weight of the granules.

Aspect 19A. The pharmaceutical composition of any one of aspects 12A to 18A, wherein the granules have a mean diameter from 100 μm to 500 μm.

Aspect 20A. The pharmaceutical composition of any one of aspects 1A to 19A, wherein the pharmaceutical composition comprises from 35 wt % to 55 wt % of the granules, wherein wt % is based on the total weight of the pharmaceutical composition.

Aspect 21A. The pharmaceutical composition of any one of aspects 1A to 20A, wherein the controlled release polymer comprises carbomer copolymers, shellac, carbomer homopolymers, hypromellose (hydroxypropyl methylcellulose) polymers, carbomer interpolymers, carboxymethylcellulose sodium, carrageenan, cellaburate, ethylcellulose, glyceryl monooleate, pregelatinized modified starch, glyceryl monostearate, guar gum, hydroxypropyl betadex, hydroxypropyl cellulose, polyethylene oxide, polyvinyl acetate dispersion, sodium alginate, pregelatinized starch, xanthan gum, alginic acid, ethylacrylate/methyl methacrylate copolymers, acrylic acid/allyl sucrose polymers, acrylic acid/allyl pentaerythritol polymers, acrylic acid/alkyl acrylate/allyl pentaerythritol copolymers, or a combination of any of the foregoing.

Aspect 22A. The pharmaceutical composition of any one of aspects 1A to 20A, wherein the controlled release polymer comprises hydroxypropylmethyl cellulose.

Aspect 23A. The pharmaceutical composition of aspect 22A, wherein the hydroxypropylmethyl cellulose is characterized by a methoxyl content from 22% to 24%; a pH in a 2% water at 25° C. from 5 to 8; a hydroxypropoxyl content 7.5% to 9.5%; a viscosity from 80 mPa-s (cP) to 120 mPa-s (cP) as a 2% aqueous solution at 20° C.

Aspect 24A. The pharmaceutical composition of any one of aspects 22A to 23A, wherein the hydroxypropylmethyl cellulose is characterized by a methoxyl content from 22% to 24%; a pH in 2% water at 25° C. from 5 to 8; a hydroxypropoxyl content 7.5% to 9.5%; a viscosity (Brookfield) from 2,600 mPa-s (cP) to 5,000 mPa-s (cP) as a 2% aqueous solution at 20° C.

Aspect 25A. The pharmaceutical composition of any one of aspects 22A to 24A, wherein the hydroxypropylmethyl cellulose comprises:
from 50 wt % to 100 wt % of a hydroxypropylmethyl cellulose characterized by a methoxyl content from 22% to 24%; a pH in a 2% water at 25° C. from 5 to 8; a hydroxypropoxyl content 7.5% to 9.5%; a viscosity from 80 mPa-s (cP) to 120 mPa-s (cP) as a 2% aqueous solution at 20° C.; and
from 0 wt % to 50 wt % of a hydroxypropylmethyl cellulose characterized by a methoxyl content from 22% to 24%; a pH in 2% water at 25° C. from 5 to 8; a hydroxypropoxyl content 7.5% to 9.5%; a viscosity (Brookfield) from 2,600 mPa-s (cP) to 5,000 mPa-s (cP) as a 2% aqueous solution at 20° C.;
wherein wt % is based on the total weight of the hydroxypropylmethyl cellulose.

Aspect 26A. The pharmaceutical composition of any one of aspects 1A to 25A, wherein the pharmaceutical composition comprises from 10 wt % to 60 wt % of the controlled release polymer, wherein wt % is based on the total weight of the pharmaceutical composition.

Aspect 27A. The pharmaceutical composition of any one of aspects 1A to 26A, wherein the anionic sulfate/sulfonate surfactant is characterized by a critical micelle concentration of from 2 g/L to 3 g/L (6.9 mmol/L to 10.4 mmol/L) at 20° C.

Aspect 28A. The pharmaceutical composition of any one of aspects 1A to 27A, wherein the anionic sulfate/sulfonate surfactant comprises sodium lauryl sulfate.

Aspect 29A. The pharmaceutical composition of aspect 28A, wherein the sodium lauryl sulfate is characterized by a critical micelle concentration of from 2.2 g/L to 2.5 g/L at 20° C.

Aspect 30A. The pharmaceutical composition of any one of aspects 1A to 29A, wherein the pharmaceutical composition comprises from 5 wt % to 15 wt % of the anionic sulfate/sulfonate surfactant, wherein wt % is based on the total weight of the pharmaceutical composition.

Aspect 31A. The pharmaceutical composition of any one of aspects 1A to 30A, wherein the pharmaceutical composition comprises a filler.

Aspect 32A. The pharmaceutical composition of aspect 31A, wherein the filler comprises microcrystalline cellulose.

Aspect 33A. The pharmaceutical composition of any one of aspects 31A to 32A, wherein the pharmaceutical composition comprises from 5 wt % to 35 wt % of the filler, wherein wt % is based on the total weight of the pharmaceutical composition.

Aspect 34A. The pharmaceutical composition of any one of aspects 1A to 33A, wherein the pharmaceutical composition comprises a lubricant.

Aspect 35A. The pharmaceutical composition of aspect 34A, wherein the lubricant comprises magnesium stearate.

Aspect 36A. The pharmaceutical composition of any one of aspects 34A to 35A, wherein the pharmaceutical composition comprises from 0.1 wt % to 1.5 wt % of the lubricant, wherein wt % is based on the total weight of the pharmaceutical composition.

Aspect 37A. The pharmaceutical composition of any one of aspects 1A to 36A, wherein the pharmaceutical composition comprises:
from 30 wt % to 60 wt % of the granules;
from 10 wt % to 60 wt % of the controlled release polymer; and
from 5 wt % to 15 wt % of the anionic sulfate/sulfonate surfactant,
wherein wt % is based on the total weight of the pharmaceutical composition.

Aspect 38A. The pharmaceutical composition of any one of aspects 1A to 36A, wherein the pharmaceutical composition comprises:
from 35 wt % to 55 wt % of the granules;
from 20 wt % to 40 wt % of the controlled release polymer;
from 10 wt % to 20 wt % of a filler;
from 5 wt % to 15 wt % of the anionic sulfate/sulfonate surfactant; and
from 0.1 wt % to 1.0 wt % of a lubricant,
wherein wt % is based on the total weight of the pharmaceutical composition.

Aspect 39A. The pharmaceutical composition of aspect 38A, wherein,
the controlled release polymer comprises hydroxypropylmethyl cellulose;
the filler comprises microcrystalline cellulose;
the anionic sulfate/sulfonate surfactant comprises sodium lauryl sulfate; and
the lubricant comprises magnesium stearate.

Aspect 40A. The pharmaceutical composition of any one of aspects 1A to 39A, wherein the pharmaceutical composition comprises a granulation.

Aspect 41A. The pharmaceutical composition of any one of aspects 1A to 39A, wherein the pharmaceutical composition comprises a tablet oral dosage form.

Aspect 42A. An oral dosage form prepared from the pharmaceutical composition of any one of aspects 1A to 41A.

Aspect 43A. An oral dosage form comprising the pharmaceutical composition of any one of aspects 1A to 41A.

Aspect 44A. The oral dosage form of aspect 43A, wherein the oral dosage form comprises a solid oral dosage form.

Aspect 45A. The oral dosage form of aspect 43A, wherein the oral dosage form comprises a tablet.

Aspect 46A. The oral dosage form of any one of aspects 42A to 45A, wherein the oral dosage form comprises from 25 mg to 400 mg of the compound of Formula (1) or a pharmaceutically acceptable salt thereof.

Aspect 47A. The oral dosage form of any one of aspects 42A to 46A, wherein the oral dosage form comprises:
from 35 wt % to 55 wt % of the compound of Formula (1); and
from 0.5 wt % to 1.5 wt % of hydroxypropylmethyl cellulose E3;
wherein wt % is based on the total weight of the oral dosage form.

Aspect 48A. The oral dosage form of any one of aspects 42A to 46A, wherein the oral dosage form comprises:
from 35 wt % to 55 wt % of the compound of Formula (1);
from 0.5 wt % to 1.5 wt % of hydroxypropylmethyl cellulose E3;
from 20 wt % to 40 wt % of a controlled release polymer;
from 10 wt % to 20 wt % of microcrystalline cellulose;
from 5 wt % to 15 wt % of sodium lauryl sulfate; and
from 0.1 wt % to 1.0 wt % of magnesium stearate,
wherein wt % is based on the total weight of the tablet dosage form.

Aspect 49A. The oral dosage form of aspect 48A, wherein the controlled release polymer is selected from hydroxypropylmethyl cellulose K100 Premium LV DC2, hydroxypropylmethyl cellulose K4M Premium DC2, or a combination thereof.

Aspect 50A. The oral dosage form of any one of aspects 46A and 49A, wherein the compound of Formula (1) comprises ((((S)-1-(2-chlorophenyl)-2-oxocyclohexyl)(methyl)carbamoyl)oxy)methyl dimethyl-L-valinate (39).

Aspect 51A. The oral dosage form of any one of aspects 46A and 49A, wherein the compound of Formula (1) comprises ((((S)-1-(2-chlorophenyl)-2-oxocyclohexyl)(methyl)carbamoyl)oxy)methyl dimethyl-L-valinate (39) HCl.

Aspect 52A. The oral dosage form of any one of aspects 45A to 51A, wherein the tablet oral dosage form exhibits a zero-order release profile of the compound of Formula (1) or a pharmaceutically acceptable salt thereof over a duration of six hours in a two-stage dissolution medium as determined using a USP I dissolution apparatus with an agitation rate of 100 RPM and at a temperature of 37° C., wherein,
the first stage comprises immersing the tablet dosage form in 0.1N hydrochloric acid for 1 hour; and
the second stage comprises immersing the tablet dosage form in a 50 mM acetate buffer at pH 4.5 for the duration.

Aspect 53A. The oral dosage form of aspect 52A, wherein the tablet oral dosage form is characterized by a dissolution profile of the compound of Formula (1) or a pharmaceutically acceptable salt thereof in a two-stage dissolution medium as determined using a USP I dissolution apparatus with an agitation rate of 100 RPM and at a temperature of 37° C., wherein,
from 20% to 40% of the compound of Formula (1) is released at 2 hours;
from 30% to 50% of the compound of Formula (1) is released at 4 hours;
from 70% to 80% of the compound of Formula (1) is released at 8 hours;
from 80% to 100% of the compound of Formula (1) is released at 12 hours;
from 80% to 100% of the compound of Formula (1) is released at 16 hours;
the first stage comprises immersing the oral dosage form in 0.1N hydrochloric acid for 1 hour;
the second stage comprises immersing the oral dosage form in a 50 mM acetate buffer at pH 4.5 for the duration; and
percent (%) is based on the total amount of the compound of Formula (1) or a pharmaceutically acceptable salt thereof in the oral dosage form before the immersion.

Aspect 54A. The oral dosage form of aspect 52A, wherein the tablet oral dosage form is characterized by a dissolution profile of the compound of Formula (1) or a pharmaceutically acceptable salt thereof in a two-stage dissolution medium as determined using a USP I dissolution apparatus with an agitation rate of 100 RPM and at a temperature of 37° C., wherein,
from 30% to 40% of the compound of Formula (1) is released at 2 hours;
from 50% to 70% of the compound of Formula (1) is released at 4 hours;
from 70% to 90% of the compound of Formula (1) is released at 8 hours;
greater than 90% of the compound of Formula (1) is released at 12 hours;

the first stage comprises immersing the oral dosage form in 0.1N hydrochloric acid for 1 hour;

the second stage comprises immersing the oral dosage form in a 50 mM acetate buffer at pH 4.5 for the duration; and percent (%) is based on the total amount of the compound of Formula (1) or a pharmaceutically acceptable salt thereof in the oral dosage form before the immersion.

Aspect 55A. The oral dosage form of aspect 52A, wherein the tablet oral dosage form is characterized by a dissolution profile of the compound of Formula (1) or a pharmaceutically acceptable salt thereof in a two-stage dissolution medium as determined using a USP I dissolution apparatus with an agitation rate of 100 RPM and at a temperature of 37° C., wherein, from 15% to 25% of the compound of Formula (1) is released at 2 hours;

from 20% to 35% of the compound of Formula (1) is released at 4 hours;

from 50% to 60% of the compound of Formula (1) is released at 8 hours;

from 70% to 85% of the compound of Formula (1) is released at 12 hours;

from 80% to 100% of the compound of Formula (1) is released at 16 hours;

the first stage comprises immersing the oral dosage form in 0.1N hydrochloric acid for 1 hour;

the second stage comprises immersing the oral dosage form in a 50 mM acetate buffer at pH 4.5 for the duration; and percent (%) is based on the total amount of the compound of Formula (1) or a pharmaceutically acceptable salt thereof in the oral dosage form before the immersion.

Aspect 56A. The oral dosage form of aspect 52A, wherein the two-stage dissolution profile is bioequivalent to any one of the dissolution profiles shown in FIG. 1.

Aspect 57A. The oral dosage form of any one of aspects 45A to 56A, wherein, following oral administration of a tablet dosage form comprising 100 mg of a compound of Formula (1) to a population of fasted, healthy subjects, the AUC0-inf of the plasma esketamine concentration is from 60 hr×ng/mL to 120 hr×ng/mL; and/or the AUC0-inf of the plasma noresketamine concentration is from 850 hr×ng/mL to 1,000 hr×ng/mL.

Aspect 58A. The oral dosage form of any one of aspects 45A to 57A, wherein, following oral administration of a tablet oral dosage form comprising 100 mg of a compound of Formula (1) to a population of fasted, healthy subjects, the maximum plasma esketamine concentration is from 5 ng/mL to 10 ng/mL; and/or the maximum plasma norketamine concentration is from 40 ng/mL to 80 ng/mL.

Aspect 59A. The oral dosage form of any one of aspects 45A to 58A, wherein, following oral administration of a tablet oral dosage form comprising from 100 mg to 400 mg of a compound of Formula (1) to a population of fasted, healthy subjects, the maximum plasma esketamine concentration is less than 30 ng/mL; and/or the maximum plasma noresketamine concentration is less than 250 ng/mL.

Aspect 60A. The oral dosage form of any one of aspects 45A to 59A, wherein, following oral administration of a tablet oral dosage form comprising from 100 mg to 400 mg of a compound of Formula (1) to a population of fasted, healthy subjects, the ratio of Cmax/Cave(0h-24h) for esketamine is from 2 to 4, wherein, Cmax is the maximum plasma esketamine concentration; and Cave(0h-24h) is the average plasma esketamine concentration at from 0 hours to 24 hours following oral administration of the tablet dosage form.

Aspect 61A. The oral dosage form of any one of aspects 45A to 60A, wherein, following oral administration of a tablet oral dosage form comprising from 100 mg to 400 mg of a compound of Formula (1) to a population of fasted, healthy subjects, the ratio of Cmax/Cave(0h-24h) for esketamine is from 2.5 to 3.5, wherein, Cmax is the maximum plasma esketamine concentration; and Cave(0h-24h) is the average plasma esketamine concentration from 0 hours to 24 hours following oral administration of the tablet dosage form.

Aspect 62A. The oral dosage form of any one of aspects 45A to 61A, wherein, following oral administration of a tablet oral dosage form comprising from 100 mg to 400 mg of a compound of Formula (1) to a population of fasted, healthy subjects, the ratio of Cmax/Cave(0h-24h) for noresketamine is from 1 to 3, wherein, Cmax is the maximum plasma noresketamine concentration; and Cave(0h-24h) is the average plasma noresketamine concentration from 0 hours to 24 hours following oral administration of the tablet dosage form.

Aspect 63A. The oral dosage form of any one of aspects 45A to 62A, wherein, following oral administration of a tablet oral dosage form comprising from 100 mg to 400 mg of a compound of Formula (1) to a population of fasted, healthy subjects, the ratio of Cmax/Cave(0h-24h) for noresketamine is from 1.5 to 2.5, wherein, Cmax is the maximum plasma noresketamine concentration; and Cave(0h-24h) is the plasma noresketamine concentration from 0 hours to 24 hours following oral administration of the tablet dosage form.

Aspect 64A. The oral dosage form of any one of aspects 52A to 63A, wherein, the compound of Formula (1) comprises ((((S)-1-(2-chlorophenyl)-2-oxocyclohexyl)(methyl)carbamoyl)oxy)methyl dimethyl-L-valinate (39).

Aspect 65A. The oral dosage form of any one of aspects 52A to 63A, wherein, the compound of Formula (1) comprises ((((S)-1-(2-chlorophenyl)-2-oxocyclohexyl)(methyl)carbamoyl)oxy)methyl dimethyl-L-valinate (39) HCl.

Aspect 66A. A kit comprising the pharmaceutical composition of any one of aspects 1A to 41A or the oral dosage form of any one of aspects 42A to 65A.

Aspect 67A. A method of treating a disease in a patient comprising orally administering to a patient in need of such treatment a therapeutically effective amount of the pharmaceutical composition of any one of aspects 1A to 41A or the oral dosage form of any one of aspects 42A to 65A, wherein the disease is selected from a neurological disease, a psychiatric disease, and pain.

Aspect 68A. The method of aspect 67A, wherein the disease is depression.

Aspect 69A. The method of aspect 68A, wherein the depression is selected from major depressive disorder, dysthymia, persistent depression disorder, bipolar disorder, seasonal affective disorder, psychotic depression, peripartum depression, premenstrual dysphoric disorder, situational depression, atypical depression, treatment resistant depression, endogenous depression, cyclothymic disorder, and disruptive mood dysregulation disorder.

Aspect 70A. The method of aspect 68A, wherein the depression is major depressive disorder.

Aspect 71A. A method of treating a disease in a patient comprising orally administering to a patient in need of such treatment a therapeutically effective amount of the pharmaceutical composition of any one of aspects 1A to 41A, wherein the disease is treated by inhibiting NMDA receptors.

Aspect 72A. A method of treating a disease in a patient comprising orally administering to a patient in need of such treatment a therapeutically effective amount of the oral dosage form of any one of aspects 42A to 65A, wherein the disease is selected from a neurological disease, a psychiatric disease, and pain.

Aspect 73A. The method of aspect 72A, wherein the disease is depression.

Aspect 74A. The method of aspect 73A, wherein the depression is selected from major depressive disorder, dysthymia, persistent depression disorder, bipolar disorder, seasonal affective disorder, psychotic depression, peripartum depression, premenstrual dysphoric disorder, situational depression, atypical depression, treatment resistant depression, endogenous depression, cyclothymic disorder, and disruptive mood dysregulation disorder.

Aspect 75A. The method of aspect 73A, wherein the depression is major depressive disorder.

Aspect 76A. A method of treating a disease in a patient comprising orally administering to a patient in need of such treatment a therapeutically effective amount of the oral dosage form of any one of aspects 42A to 65A, wherein the disease is treated by inhibiting NMDA receptors.

Aspect 77A. Use of the pharmaceutical composition of the pharmaceutical composition of any one of aspects 1 to 41 in the manufacture of a medicament for treating a disease in a patient, wherein the disease is selected from a neurological disease, a psychiatric disease, and pain.

Aspect 78. The use of aspect 77A, wherein the disease is depression.

Aspect 79A. The use of aspect 78, wherein the depression is selected from major depressive disorder, dysthymia, persistent depression disorder, bipolar disorder, seasonal affective disorder, psychotic depression, peripartum depression, premenstrual dysphoric disorder, situational depression, atypical depression, treatment resistant depression, endogenous depression, cyclothymic disorder, and disruptive mood dysregulation disorder.

Aspect 80A. The use of aspect 78A, wherein the depression is major depressive disorder.

Aspect 81A. Use of the pharmaceutical composition of any one of aspects 1A to 41A in the manufacture of a medicament for treating a disease in a patient, wherein the disease is treated by inhibiting NMDA receptors.

EXAMPLES

The following examples describe in detail pharmaceutical compositions provided by the present disclosure and oral dosage forms provided by the present disclosure. It will be apparent to those skilled in the art that many modifications, both to materials and methods, may be practiced without departing from the scope of the disclosure.

In the examples, ketamine derivative Compound (39) was formulated as the hydrochloride salt.

The pharmacokinetic parameters disclosed in the present application were calculated using Phoenix® WinNonlin® version 8.2 software used for non-compartmental analysis, pharmacokinetic/pharmacodynamic, and toxicokinetic modeling, available from Certara Corporation, Menlo Park, Calif. Pharmacokinetic parameters were computed for each subject based on actual rather than protocol-nominal elapsed times. Area-Under-the-Curve (AUC) parameters were computed using the linear trapezoidal rule from time zero to the target time point. For example, the AUC was computed for durations from time zero to 6 hours ($AUC_{0-6h}$) and from time zero to infinity ($AUC_{0-inf}$). For $AUC_{0-6}$, if the actual elapsed time at the 6-hour collection time was not exactly 6 hours, the concentration at 6 hours post-dose was estimated by extrapolation using the half-life slope estimate. $AUC_{0-inf}$ was computed using the following formula: $AUC_{0-inf} = AUC_{0-last} + C_{plast}/slope$, where $AUC_{0-last}$ is the AUC from time zero to the time point of the last measurable concentration ($C_{plast}$) and slope is the half-life slope. The half-life slope was computed using linear regression on the terminal portion of the natural log concentration vs time profile.

Example 1

Granulation

To prepare a granulation, a ketamine derivative of Formula (1), a binder, and water in the amounts shown in Table 1 were blended using a GMX Granumeist® High Shear Granulator were blended.

TABLE 1

Granulation properties.

| Constituent | Material | Amount (wt %) |
|---|---|---|
| Ketamine Derivative | Compound (39) | 98 |
| Binder | Pharmacoat ® 603 | 2 |
| Water | USP | 18.2 |
| Total | | [1] 100 |

[1] Water not included

The dry materials were added to a GMX bowl and mixed for 1 min with an impeller speed of 870 RPM. Atomized water was added to the GMX bowl at 1.0 g/min while mixing with an impeller speed of 850 RPM and a chopper speed of 3600 rpm. The material was wet massed for 5 min between water additions at 560 rpm, and oven dried for about 14 hours at 40° C., LOD 0.2%.

The milled granules had a mean particle diameter of about 250 μm when sieved through a 30 mesh screen. The properties of a milled granulation are shown in Table 2.

TABLE 2

Granulation properties.

| Property | Value |
|---|---|
| Bulk density | 0.45 g/mL |
| Tapped density | 0.62 g/mL |
| Compressibility Index | 28.0 |
| Angle of Repose | 41.2° |
| Flow through Orifice | 16 mm |

Example 2

Pharmaceutical Compositions Containing Sodium Lauryl Sulfate

Pharmaceutical compositions with and without sodium lauryl sulfate were prepared as described in Example 3 and tablets prepared as described in Example 4. The constituents of the tablets are provided in Table 3.

TABLE 3

Pharmaceutical composition constituents.

| Material | D (wt %) | E (wt %) | F (wt %) |
|---|---|---|---|
| [1] Compound (39) | 44.38 | 43.38 | 43.38 |
| [2] Hydroxypropylmethyl cellulose | 30.0 | 30.0 | 40.0 |
| [3] Microcrystalline cellulose | 15.12 | 25.12 | 5.12 |
| [4] Sodium lauryl sulfate | 10.0 | 0.0 | 10.0 |
| [5] Magnesium Stearate | 0.5 | 0.5 | 0.5 |

[1] Granules having 98 wt % ketamine derivative (39) from Example 1.
[2] Methocel® K100 Premium DC available from Colorcon, Inc.
[3] Microcrystalline cellulose, Avicel® PH 102 available from Dupont.
[4] Sodium lauryl sulfate, Kolliphore® SLS, available from BASF.
[5] Magnesium stearate, available from Mallinckrodt.

Figure 2:
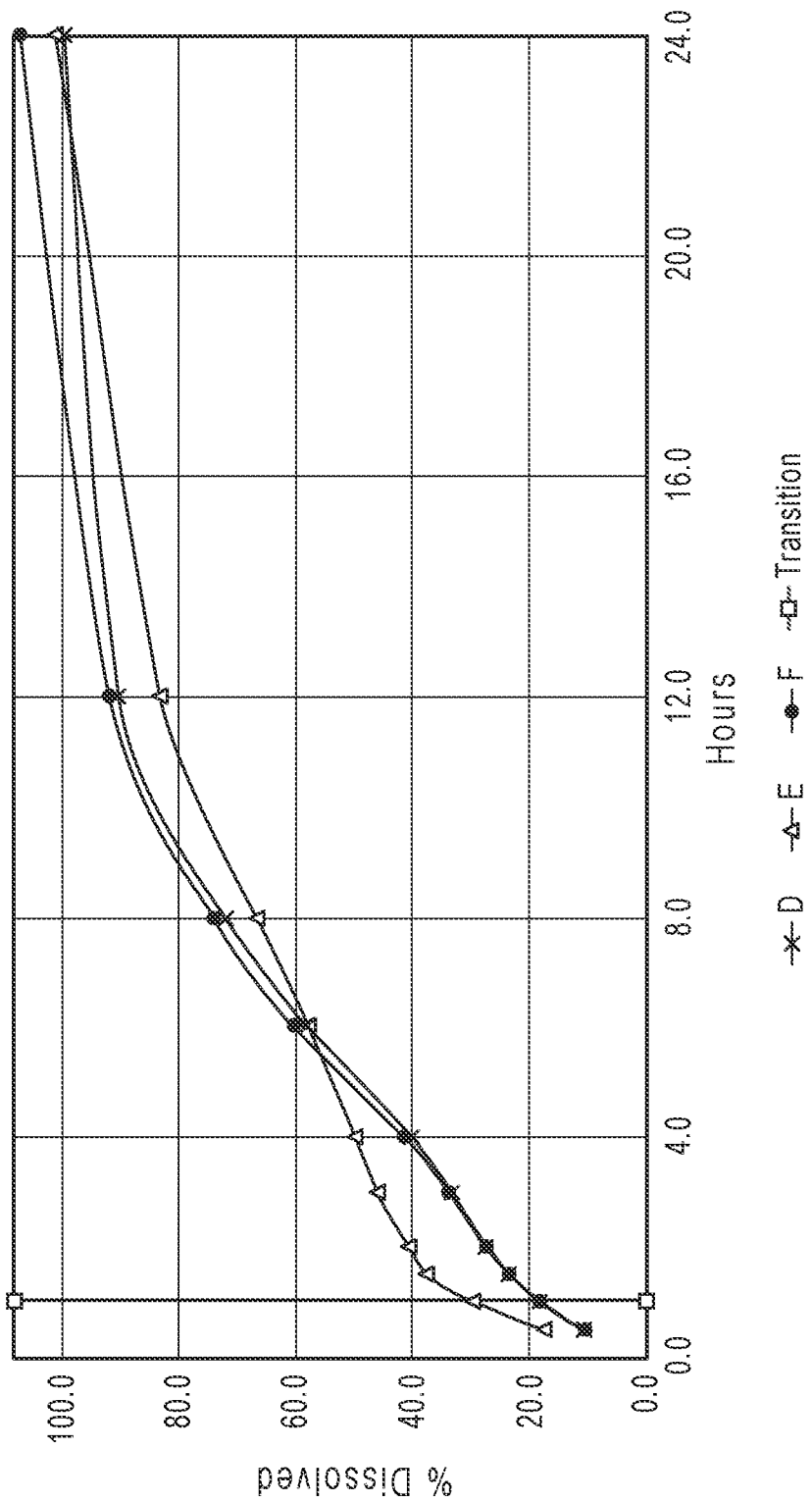
FIG. 2 shows dissolution profiles for examples of oral dosage forms with and without sodium lauryl sulfate.

The two-stage dissolution profiles showing the amount of compound (39) released overtime for the sodium lauryl sulfate-containing tablets are shown in FIG. 2. The transition line indicates the time when the dissolution medium was changed from 0.1N HCl to a 50 mM pH 4.5 acetate buffer.

The two-stage dissolution profiles were obtain as described in Example 5.

As shown in FIG. 2, sodium lauryl sulfate reduces the solubility of compound (39) in the acid stage. At pH 4.5 the dissolution rate is approximately independent of the amount of sodium lauryl sulfate suggesting that there is no ionic interaction between sodium lauryl sulfate and compound (39).

Example 3

Pharmaceutical Composition

The constituents of examples of pharmaceutical compositions are shown in Table 4.

TABLE 4

Pharmaceutical composition constituents.

| Constituent | Material | A (wt %) | B (wt %) | C (wt %) |
|---|---|---|---|---|
| Granules | [1] Compound (39) | 44.4 | 44.4 | 44.4 |
| Controlled Release Polymer | [2] HPMC K100 DC | 30.0 | 20.0 | 20.0 |
|  | [3] HPMC K4M DC | 0.0 | 0.0 | 10.0 |
| Anionic sulfate/ sulfonate surfactant | [4] Sodium lauryl sulfate | 10.0 | 10.0 | 10.0 |
| Filler | [5] Microcrystalline cellulose | 15.1 | 25.1 | 15.1 |
| Lubricant | [6] Magnesium Stearate | 0.5 | 0.5 | 0.5 |
|  | Total | 100.0 | 100.0 | 100.0 |

[1] Granules having 98 wt % ketamine derivative (39) from Example 1.
[2] HPMC K100 DC, Methocel® K100 Premium LV DC available from Colorcon, Inc.
[3] HPMC K4M DC, Methocel® K4M Premium DC2 available from Colorcon, Inc.
[4] Sodium lauryl sulfate, Kolliphore® SLS, available from BASF.
[5] Microcrystalline cellulose, Avicel® PH 102 available from Dupont.
[6] Magnesium stearate, available from Mallinckrodt.

A pharmaceutical composition was prepared be first passing the granulation and the sodium lauryl sulfate through a 35-mesh screen. The screened materials, the hydroxypropyl methylcellulose, and the microcrystalline cellulose were added to a 250 mL jar and attached to a V-blender. The formulation was blended for 5 minutes. Magnesium stearate, passed through a 35-mesh screen was added, and the formulation blended for an additional 1 minute to provide the pharmaceutical composition.

Example 4

Oral Dosage Form

Oral tablets were prepared by hand using a Piccola B/D tablet press equipped with a 9 mm round tooling by compacting the pharmaceutical composition of Example 2 with a compression force of 1700 PSI to provide oral tablets having an average hardness from about 8 kP to 10 kP.

The oral tablets had a weight of about 250 mg, and a thickness of about 4.1 mm.

Example 5

Dissolution Profiles of Oral Dosage Form

A two-stage dissolution apparatus was used to measure the dissolution profile of the tablets.

In the first stage, the tablets were immersed in 0.1N HCl a dissolution medium for 1 hour.

The dissolution medium was then immediately charged to a 50 mM acetate buffer at pH 4.5 immediately following 1 hour sampling via addition of 100 mM acetate buffer with appropriate pH and continued through 18 hours. The conditions of the dissolution apparatus are shown in Table 5.

TABLE 5

Dissolution apparatus conditions.

| Condition | Setting |
|---|---|
| Apparatus | USP I baskets |
| Agitation Rate | 100 RPM |
| Vessel Temperature | 37° C. |
| Sample Times—Stage 1 | 0.1N HCl |
|  | Sampled at 0.5 and 1 hours |
| Sample Times—Stage 2 | 50 mM pH 4.5 acetate buffer |
|  | Sampled at 1.5, 2, 3, 4,6, 8, and 12 and 18 hours |
| Sample Volume | 10 mL Autosampler |
| Dissolution Media Volume—Stage 1 | 500 mL |
| Dissolution Media Volume—Stage 2 | 1,000 mL |
| Filter | 45 µm in-line |
| Auto-sampler Settings | Flushing 6 mL, twice, offset 3 mL |
|  | Replace OFF, Recycle ON |

Dissolution profiles showing the amount of compound (39) released over time for tablets prepared using pharmaceutical compositions (A), (B), and (C) are shown in FIG. 1.

Example 6

Modified Release Dosage Forms

Modified release tablets were prepared by first preparing a granulation of Compound (39) and hydroxypropylmethyl cellulose E3 (Pharmacoat® 603). The granulation included 98% of Compound (39). The granulation, hydroxypropylmethyl cellulose, sodium lauryl sulfate, and microcrystalline cellulose in the amounts listed in Table 6 were combined, mixed using a V-blender, and sieved through a 35-mesh screen. The sieved formulation was then blended for 20 minutes using a V-blender. Magnesium stearate was sieved through a 35-mesh screen and added to the blended formulation. The formulation with the added magnesium stearate was blended for an additional 2 minutes.

TABLE 6

Constituents of modified release formulations.

| Material | MR1 mg/tablet | MR1 % w/w | MR2 mg/tablet | MR2 % w/w | MR3 mg/tablet | MR3 % w/w |
|---|---|---|---|---|---|---|
| [1] Compound (39) HCl | 107.75 | 43.1 | 107.75 | 43.5 | 107.75 | 43.1 |
| [2] HPMC E3 | 2.20 | 0.9 | 2.20 | 0.9 | 2.20 | 0.9 |
| [3] Microcrystalline cellulose | 37.80 | 15.1 | 62.80 | 25.1 | 37.80 | 15.1 |
| [4] HPMC K100 | 75.00 | 30.0 | 50.00 | 20.0 | 50.00 | 20.0 |
| [5] HPMC K4M | — | — | — | — | 25.00 | 10.0 |
| [6] Sodium lauryl sulfate | 25.00 | 10.0 | 25.00 | 10.0 | 25.00 | 10.0 |
| [7] Magnesium Stearate | 1.25 | 0.5 | 1.25 | 0.5 | 1.25 | 0.5 |

[1] Ketamine prodrug, Compound (39).
[2] HPMC E3, Pharmacoat ® 603 available from Shin-Etsu Chemical Co., Ltd.
[3] Microcrystalline cellulose, Avicel ® PH 102 available from Dupont.
[4] HPMC K100 DC, Methocel ® K100 Premium LV DC available from Colorcon, Inc.
[5] HPMC K4M DC, Methocel ® K4M Premium DC2 available from Colorcon, Inc.
[6] Sodium lauryl sulfate, Kolliphore ® SLS, available from BASF.
[7] Magnesium stearate, available from Mallinckrodt.

Not that compound (39) and HPMC E3 constitute the granules. The mean particle diameter of the blended formulation was from about 45 μm to 110 μm as determined using sieve analysis or laser diffraction. Certain properties of the blended formulation are shown in Table 7.

TABLE 7

Properties of blended formulations.

| Test | unit | MR1 | MR2 | MR3 |
|---|---|---|---|---|
| Bulk density | g/mL | 0.47 | 0.47 | 0.48 |
| Angle of repose | deg | 40 | 39 | 39 |
| Flodex | mm | 10 | 12 | 12 |

Bulk density was determined using a bulk density cylinder.

Angle of repose was determined according to USP <1174>.

Intrinsic flowability was determined according to USP <1174> using a Flodex™ instrument.

Tablets were prepared using a Piccola B/D tablet press equipped with a 9 mm tooling, a press speed of 20 RPM, a compression force of 28 kN. The tablets had an average weight of 251 mg, an average hardness of from 6.3 kP to 6.5 kP, an average thickness from 3.63 mm to 3.75, and a friability of 0.1%.

Hardness was determined according to USP <1217> using diametral compression.

Friability was determined using a sonic sifter.

Each of the modified release tablets contained 43 wt % or 107.75 mg of Compound (39) equal to 58.3 mg equivalents of esketamine.

Two-stage dissolution profiles for the tablets are shown in FIG. 1.

Two-stage dissolution profiles for the tablets were obtained using a USP 1 dissolution apparatus. The tablets were first added to 500 mL of a 0.1N hydrochloric acid solution and agitated at 100 RPM for 1 hour at 37° C. Samples (1 mL) were withdrawn at 0, 0.5 and 1 hours. The acid solution was then replaced with 1,000 mL of a 50 mM pH 4.5 acetate buffer solution and the tablets agitated at 100 RPM for up to 24 hours at 37° C. Samples (1 mL) were withdrawn at 1.5, 2, 3, 4, 6, 8, 12, 16, 20, and 24 hours. Solution samples were withdrawn at intervals and the concentration of Compound (39) was measured using high pressure liquid chromatography mass spectroscopy.

As shown in FIG. 1, MR1 tablets are characterized by a relative intermediate release rate, MR2 tablets by a fast release rate, and MR3 tablets by a slow release rate.

Figure 3:
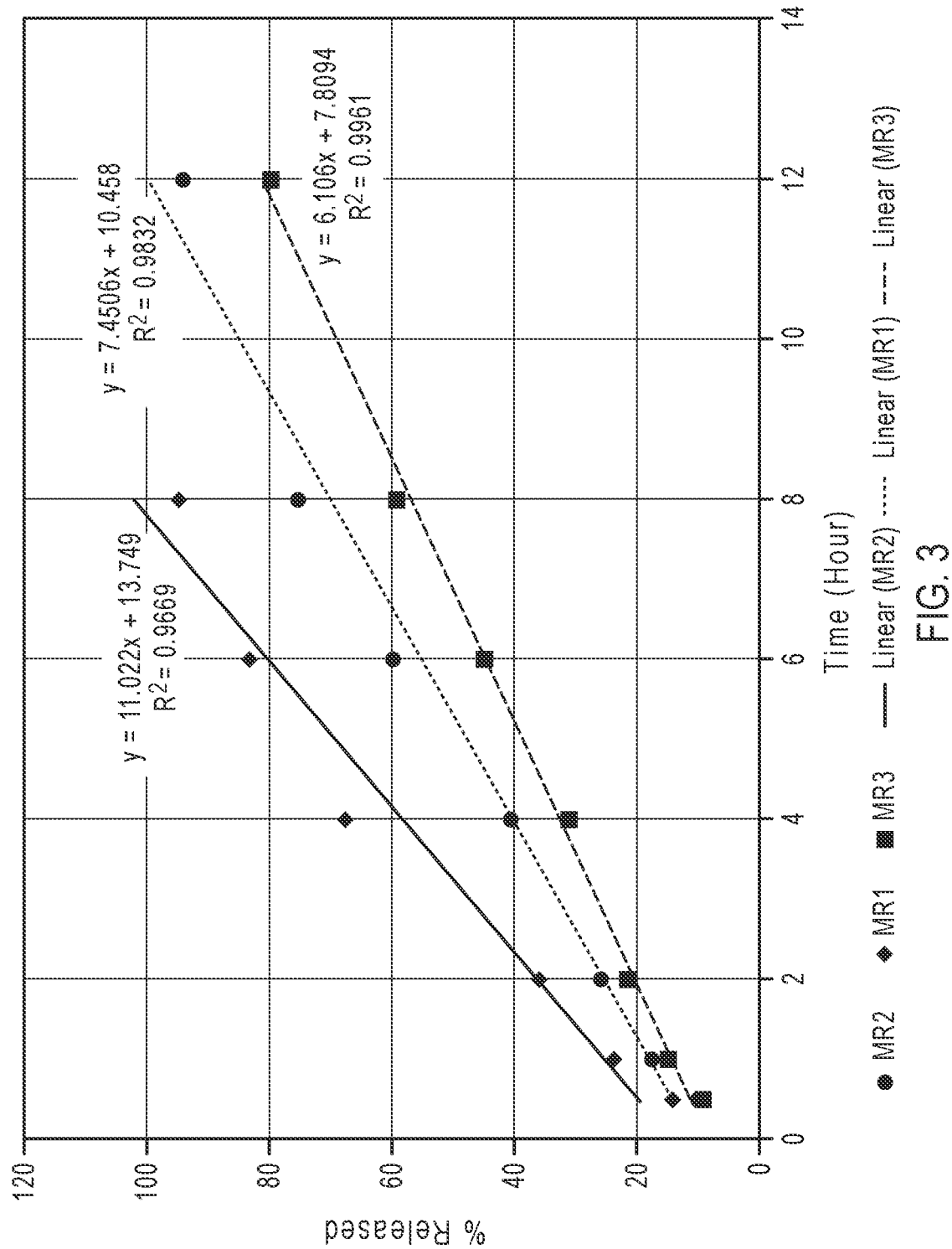
FIG. 3 shows regression curves for the dissolution profiles shown in FIG. 1.

As shown in FIG. 3, the dissolution profiles exhibited a zero-order release profile.

Example 7

Ketamine/Pharmacokinetics

The pharmacokinetics of ketamine following oral administration of the modified release tablets was determined.

Participants in each study part were required to fast for at least 10 hours overnight (clear liquids were allowed) and randomized on Day 1 prior to study drug administration. Fasting was required for 4 hours post-dose. Blood samples for pharmacokinetic measurements were collected immediately before and at 0.5h 1h, 1.5h, 2h, 2.5h, 3h, 4h, 6h, 8h, 10h, 12h, 18h, 24h, 36h, 42h, and 48h after dosing.

The plasma concentration of compound (39), esketamine and noresketamine was determined using validated liquid chromatography mass spectrometry.

The first study was an open-label, sequential, crossover assessment of single 100 mg oral doses of compound (39) in immediate release (IR) and modified release (MR) prototype formulations. Twelve (12) healthy participants received 1 dose (either an IR capsule or one of three MR tablets MR1, MR2, and MR3)) every other day (48 hours between doses) in the morning. The 12 participants were randomly assigned to one of four formulation testing sequences (ABCD, BCDA, CDAB, DABC). Participants were dosed in the mornings of Day 1, 3, 5 and 7, for a total of 4 dosing days.

Figure 4A:
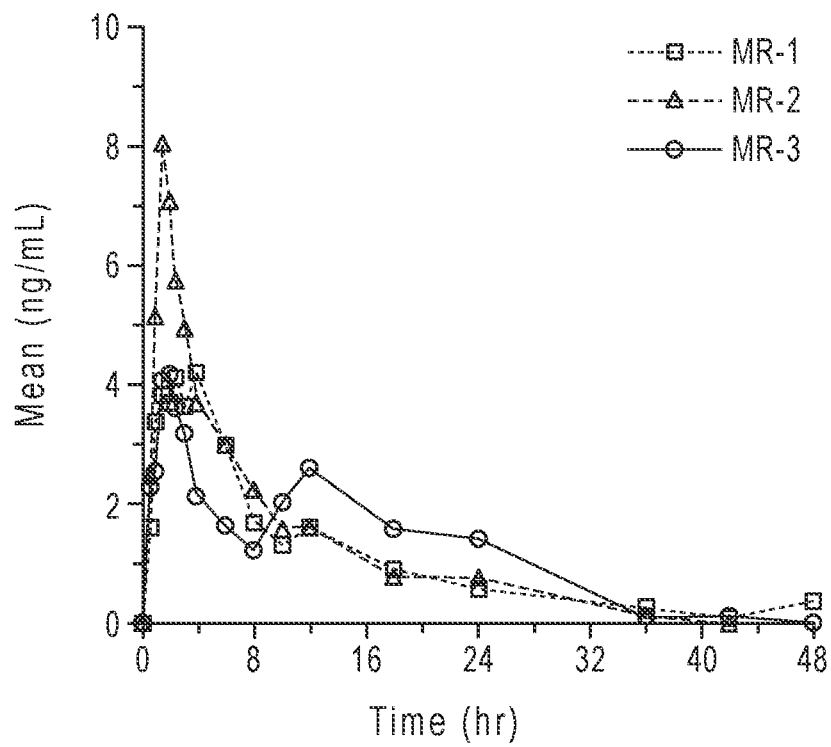
FIG. 4A shows plasma esketamine concentration-time curves following oral administration of tablets comprising 100 mg compound (39).
Figure 4B:
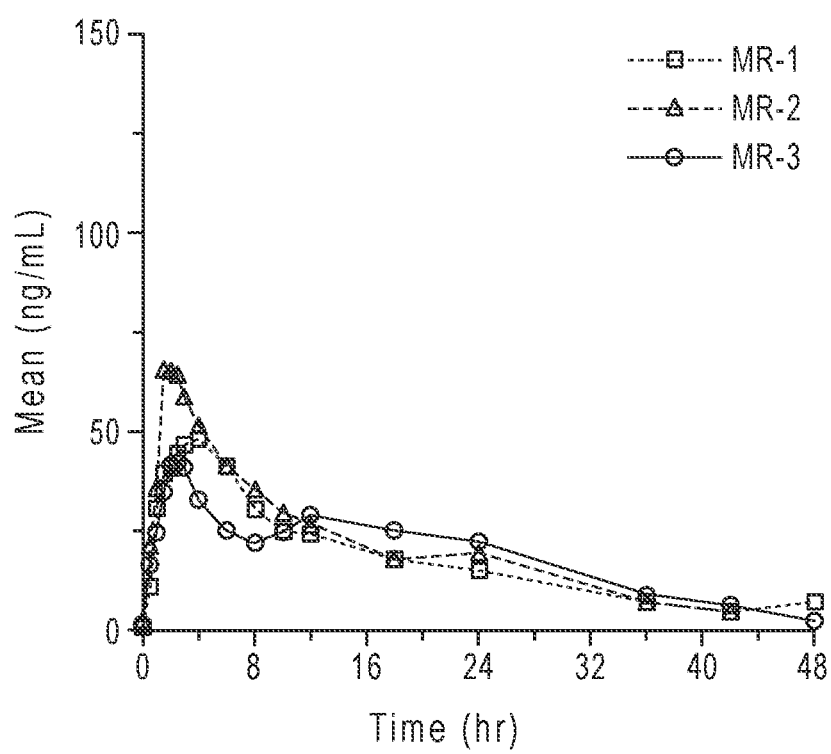
FIG. 4B shows plasma noresketamine concentration-time curves following oral administration of tablets comprising 100 mg compound (39).

The pharmacokinetic profiles for esketamine and noresketamine following oral administration of modified release tablets comprising 100 mg compound (39) are shown in FIG. 4A and in FIG. 4B, respectively. The pharmacokinetic parameters are summarized in FIG. 5.

In a second study, 5 cohorts of 8 participants each were randomized with 6 participants receiving a dose of compound (39) and 2 participants receiving a placebo. The active participant received ascending oral doses from 100 to 400 mg of compound (39) in one of three modified release tablets.

Modified release tablets (MRI tablet dosage forms) containing 100 mg, 200 mg, 300 mg, or 400 mg of compound

(39) were administered to groups of 6 fasted, healthy subjects once a day for seven (7).

Figure 6A:
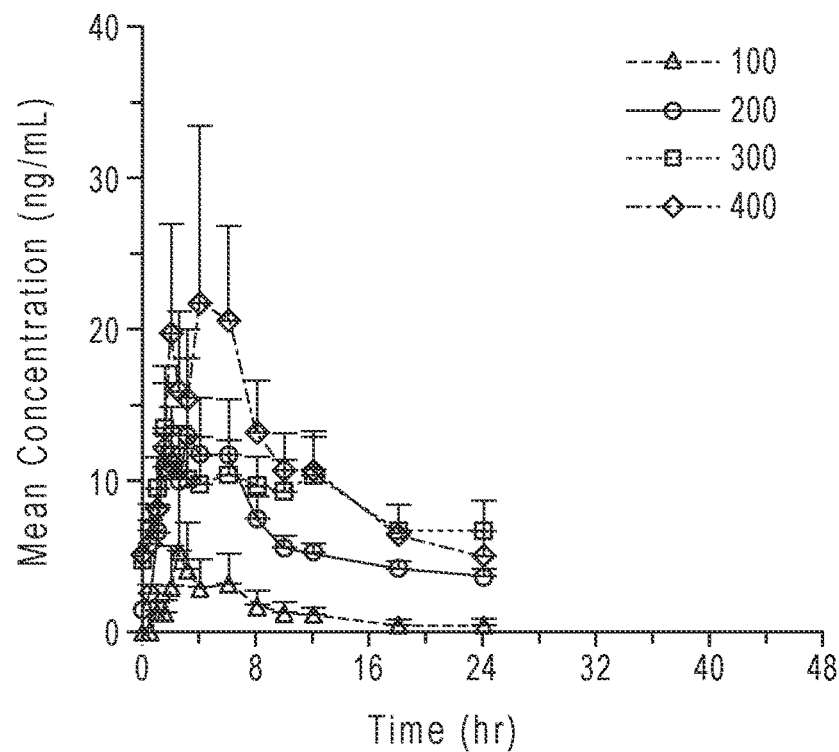
FIG. 6A shows plasma esketamine concentration-time curves following oral administration of tablets comprising 100 mg, 200 mg, 300 mg, or 400 mg compound (39) on day 1.
Figure 6B:
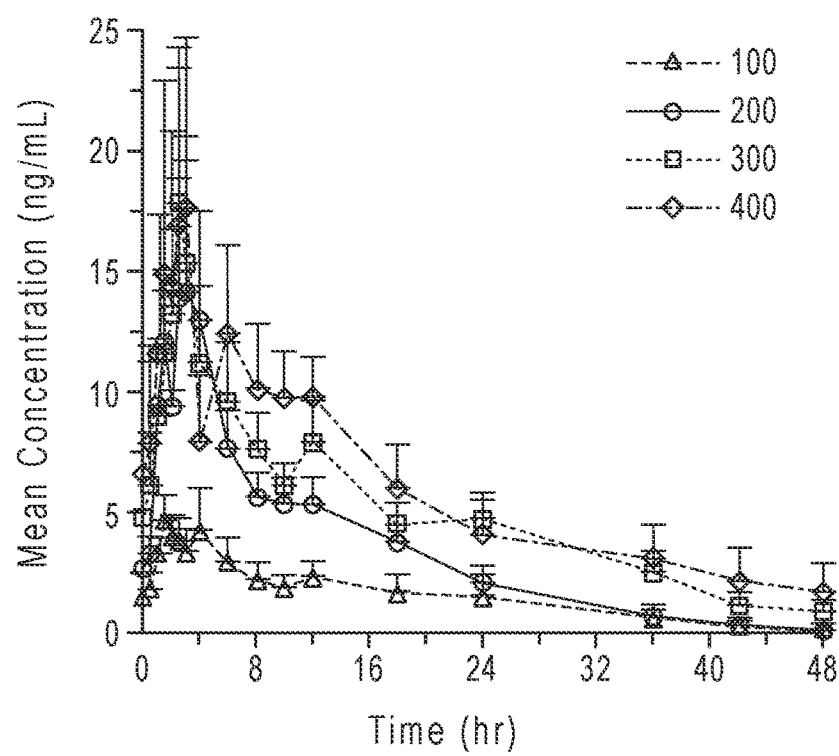
FIG. 6B shows plasma esketamine concentration-time curves following oral administration of tablets comprising 100 mg, 200 mg, 300 mg, or 400 mg compound (39) on day 7.

The pharmacokinetic profiles for the mean (+/−SEM) plasma esketamine concentration following administration of a modified release tablet comprising 100 mg, 200 mg, 300 mg, or 400 mg of compound (39) during the first day are shown in FIG. 6A, and during day 7 of the study in FIG. 6B.

Figure 7A:
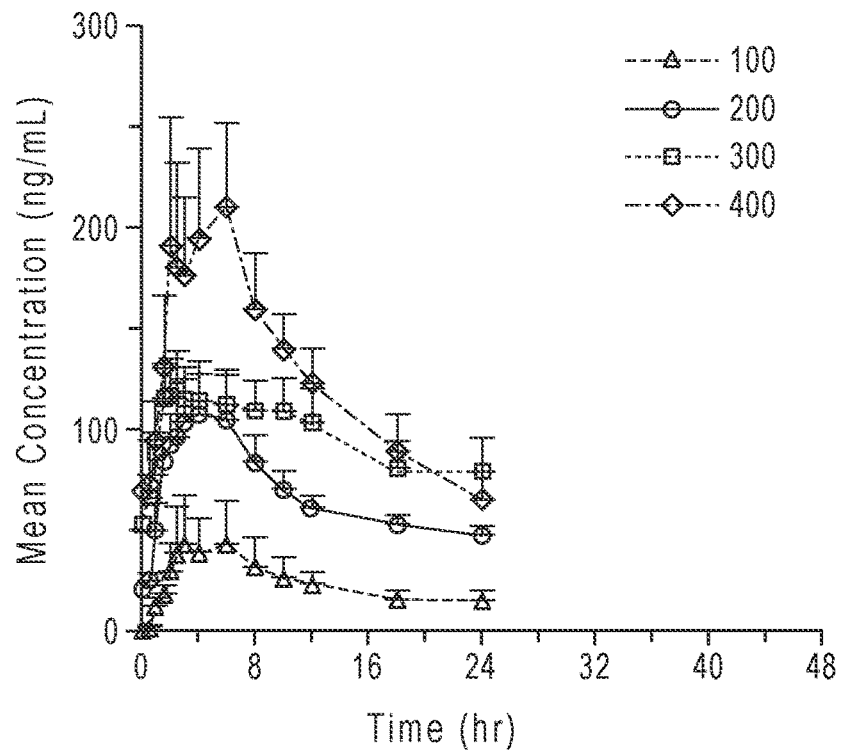
FIG. 7A shows plasma noresketamine concentration-time curves following oral administration of tablets comprising 100 mg, 200 mg, 300 mg, or 400 mg compound (39) on day 1.
Figure 7B:
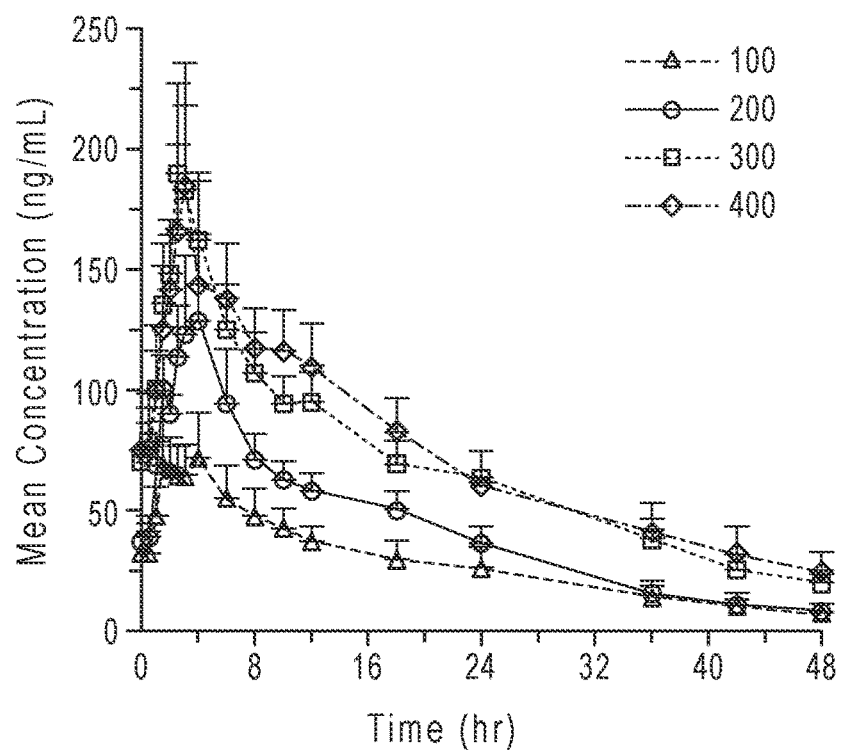
FIG. 7B shows plasma noresketamine concentration-time curves following oral administration of tablets comprising 100 mg, 200 mg, 300 mg, or 400 mg compound (39) on day 7.

The pharmacokinetic profiles for the mean (+/−SEM) plasma noresketamine concentration following administration of a modified release tablet comprising 200 mg of compound (39) during the first day are shown in FIG. 7A, and during day 7 of the study in FIG. 7B.

The pharmacokinetic parameters for the plasma esketamine and plasma noresketamine concentration-time profiles shown in FIGS. 6A-7B are provided in Tables 8-11.

TABLE 8

Summary of PK parameter for 100 mg dose of compound (39) in an MR1 tablet dosage form.

| Study | | | | Esketamine | | | Noresketamine | | |
|---|---|---|---|---|---|---|---|---|---|
| Dose (mg) | Day | Parameter | Units | N | Mean | SE | N | Mean | SE |
| 100 | 1 | Tmax | hr | 6 | 3.9 | 1.8 | 6 | 7.8 | 3.6 |
| | | Cmax | ng/mL | 6 | 8.3 | 4.6 | 6 | 64.2 | 26.5 |
| | | AUC0-last | hr × ng/mL | 6 | 32.7 | 17.7 | 6 | 574.6 | 177.0 |
| | | AUC0-inf | hr × ng/mL | 2 | 99.0 | 36.1 | 2 | 621.3 | 377.7 |
| | | AUC0-4 | hr × ng/mL | 6 | 10.2 | 7.4 | 6 | 101.7 | 45.1 |
| | | AUC0-5 | hr × ng/mL | 6 | 13.3 | 8.9 | 6 | 141.6 | 59.0 |
| | | AUC0-6 | hr × ng/mL | 6 | 16.4 | 10.1 | 6 | 183.8 | 72.2 |
| | | AUC0-7 | hr × ng/mL | 6 | 19.3 | 11.3 | 6 | 224.1 | 86.1 |
| | | AUC0-8 | hr × ng/mL | 6 | 21.4 | 12.3 | 6 | 258.8 | 99.5 |
| | | AUC0-12 | hr × ng/mL | 6 | 27.1 | 14.8 | 6 | 366.1 | 136.5 |
| | | C4 | ng/mL | 6 | 3.0 | 1.8 | 6 | 38.9 | 17.1 |
| | | C5 | ng/mL | 6 | 3.1 | 1.8 | 6 | 41.1 | 17.6 |
| | | C6 | ng/mL | 6 | 3.2 | 2.0 | 6 | 43.2 | 20.9 |
| | | C7 | ng/mL | 6 | 2.5 | 1.5 | 6 | 37.5 | 17.7 |
| | | C8 | ng/mL | 6 | 1.8 | 1.0 | 6 | 31.8 | 14.5 |
| | | t½ | hr | 2 | 7.9 | 5.1 | 2 | 5.8 | 1.3 |
| | 7 | Tmax | hr | 6 | 5.5 | 2.1 | 6 | 2.2 | 0.5 |
| | | Tlag | hr | 6 | 0.2 | 0.2 | 6 | 0.0 | 0.0 |
| | | Tmin | hr | 5 | 6.8 | 4.7 | 6 | 14.1 | 4.8 |
| | | Cmax | ng/mL | 6 | 6.3 | 1.5 | 6 | 88.5 | 20.2 |
| | | AUC0-last | hr × ng/mL | 6 | 72.9 | 28.1 | 6 | 1376.8 | 314.5 |
| | | AUC0-inf | hr × ng/mL | 3 | 138.7 | 45.8 | 6 | 1547.7 | 415.2 |
| | | AUC0-4 | hr × ng/mL | 6 | 14.1 | 3.6 | 6 | 231.8 | 45.4 |
| | | AUC0-5 | hr × ng/mL | 6 | 18.1 | 4.8 | 6 | 299.2 | 58.4 |
| | | AUC0-6 | hr × ng/mL | 6 | 21.5 | 5.8 | 6 | 358.4 | 70.9 |
| | | AUC0-7 | hr × ng/mL | 6 | 24.3 | 6.7 | 6 | 411.7 | 82.4 |
| | | AUC0-8 | hr × ng/mL | 6 | 26.8 | 7.4 | 6 | 461.3 | 93.2 |
| | | AUC0-12 | hr × ng/mL | 6 | 35.5 | 9.3 | 6 | 632.2 | 123.1 |
| | | C4 | ng/mL | 6 | 4.3 | 1.8 | 6 | 71.5 | 18.5 |
| | | C5 | ng/mL | 6 | 3.7 | 1.3 | 6 | 63.3 | 15.6 |
| | | C6 | ng/mL | 6 | 3.0 | 1.0 | 6 | 55.2 | 13.0 |
| | | C7 | ng/mL | 6 | 2.7 | 0.8 | 6 | 51.5 | 12.1 |
| | | C8 | ng/mL | 6 | 2.3 | 0.7 | 6 | 47.8 | 11.2 |
| | | Cavg | ng/mL | 5 | 2.7 | 0.7 | 6 | 41.7 | 7.8 |
| | | Cmin | ng/mL | 5 | 1.4 | 0.7 | 6 | 23.2 | 8.2 |
| | | t½ | hr | 3 | 9.8 | 4.1 | 6 | 10.5 | 1.9 |

TABLE 9

Summary of PK parameter for 200 mg dose of compound (39) in an MR1 tablet dosage form.

| Study | | | | Esketamine | | | Noresketamine | | |
|---|---|---|---|---|---|---|---|---|---|
| Dose (mg) | Day | Parameter | Units | N | Mean | SE | N | Mean | SE |
| 200 | 1 | Tmax | hr | 6 | 3.3 | 0.9 | 6 | 3.9 | 1.0 |
| | | Cmax | ng/mL | 6 | 19.9 | 4.6 | 6 | 139.3 | 21.1 |
| | | AUC0-last | hr × ng/mL | 6 | 156.0 | 17.5 | 6 | 1633.7 | 150.7 |
| | | AUC0-inf | hr × ng/mL | 2 | 226.4 | 42.6 | 1 | 2242.0 | — |
| | | AUC0-4 | hr × ng/mL | 6 | 36.7 | 7.2 | 6 | 309.9 | 45.5 |
| | | AUC0-5 | hr × ng/mL | 6 | 48.5 | 10.0 | 6 | 417.0 | 57.7 |
| | | AUC0-6 | hr × ng/mL | 6 | 60.2 | 12.0 | 6 | 522.7 | 66.4 |
| | | AUC0-7 | hr × ng/mL | 6 | 70.9 | 13.7 | 6 | 622.1 | 76.0 |
| | | AUC0-8 | hr × ng/mL | 6 | 79.5 | 15.2 | 6 | 710.8 | 85.8 |
| | | AUC0-12 | hr × ng/mL | 6 | 103.6 | 17.9 | 6 | 994.4 | 115.3 |
| | | C4 | ng/mL | 6 | 11.8 | 3.8 | 6 | 107.9 | 19.8 |

TABLE 9-continued

Summary of PK parameter for 200 mg dose of compound (39) in an MR1 tablet dosage form.

| Dose (mg) | Study Day | Parameter | Units | Esketamine N | Mean | SE | Noresketamine N | Mean | SE |
|---|---|---|---|---|---|---|---|---|---|
| | | C5 | ng/mL | 6 | 11.8 | 3.2 | 6 | 106.4 | 18.1 |
| | | C6 | ng/mL | 6 | 11.8 | 3.6 | 6 | 104.9 | 22.2 |
| | | C7 | ng/mL | 6 | 9.6 | 2.6 | 6 | 94.1 | 17.8 |
| | | C8 | ng/mL | 6 | 7.5 | 1.6 | 6 | 83.2 | 13.6 |
| | | t½ | hr | 2 | 8.6 | 1.0 | 1 | 11.0 | — |
| | 7 | Tmax | hr | 6 | 2.1 | 0.5 | 6 | 2.3 | 0.5 |
| | | Tmin | hr | 6 | 13.7 | 4.9 | 6 | 13.7 | 4.9 |
| | | Cmax | ng/mL | 6 | 20.0 | 4.5 | 6 | 155.4 | 29.2 |
| | | AUC0-last | hr × ng/mL | 6 | 160.7 | 16.9 | 6 | 2036.3 | 198.9 |
| | | AUC0-inf | hr × ng/mL | 6 | 178.1 | 16.1 | 6 | 2195.5 | 239.7 |
| | | AUC0-4 | hr × ng/mL | 6 | 42.0 | 7.6 | 6 | 370.6 | 48.4 |
| | | AUC0-5 | hr × ng/mL | 6 | 53.7 | 11.2 | 6 | 490.3 | 78.3 |
| | | AUC0-6 | hr × ng/mL | 6 | 62.7 | 13.4 | 6 | 592.7 | 104.1 |
| | | AUC0-7 | hr × ng/mL | 6 | 69.9 | 14.7 | 6 | 680.6 | 124.0 |
| | | AUC0-8 | hr × ng/mL | 6 | 76.1 | 15.4 | 6 | 757.0 | 137.8 |
| | | AUC0-12 | hr × ng/mL | 6 | 98.0 | 15.8 | 6 | 1011.0 | 159.6 |
| | | C4 | ng/mL | 6 | 13.0 | 4.5 | 6 | 128.3 | 35.9 |
| | | C5 | ng/mL | 6 | 10.4 | 3.0 | 6 | 111.0 | 29.6 |
| | | C6 | ng/mL | 6 | 7.7 | 1.6 | 6 | 93.8 | 23.4 |
| | | C7 | ng/mL | 6 | 6.7 | 1.1 | 6 | 82.2 | 17.1 |
| | | C8 | ng/mL | 6 | 5.7 | 1.0 | 6 | 70.6 | 11.2 |
| | | Cavg | ng/mL | 6 | 6.0 | 0.6 | 6 | 66.5 | 6.8 |
| | | Cmin | ng/mL | 6 | 1.3 | 0.7 | 6 | 28.7 | 7.2 |
| | | t½ | hr | 6 | 8.5 | 1.1 | 6 | 11.0 | 1.9 |

TABLE 10

Summary of PK parameter for 300 mg dose of compound (39) in an MR1 tablet dosage form.

| Dose mg | Study Day | Parameter | Units | Esketamine N | Mean | SE | Noresketamine N | Mean | SE |
|---|---|---|---|---|---|---|---|---|---|
| 300 | 1 | Tmax | hr | 6 | 2.4 | 0.9 | 6 | 3.3 | 1.0 |
| | | Cmax | ng/mL | 6 | 15.2 | 4.1 | 6 | 132.9 | 18.8 |
| | | AUC0-last | hr × ng/mL | 6 | 210.3 | 52.0 | 6 | 2312.8 | 366.6 |
| | | AUC0-inf | hr × ng/mL | 2 | 112.4 | 14.2 | — | — | — |
| | | AUC0-4 | hr × ng/mL | 6 | 39.5 | 10.5 | 6 | 404.8 | 60.4 |
| | | AUC0-5 | hr × ng/mL | 6 | 49.5 | 13.2 | 6 | 518.0 | 78.5 |
| | | AUC0-6 | hr × ng/mL | 6 | 59.8 | 15.5 | 6 | 630.5 | 94.7 |
| | | AUC0-7 | hr × ng/mL | 6 | 70.0 | 17.5 | 6 | 741.9 | 109.7 |
| | | AUC0-8 | hr × ng/mL | 6 | 79.9 | 19.4 | 6 | 852.0 | 124.0 |
| | | AUC0-12 | hr × ng/mL | 6 | 118.7 | 27.7 | 6 | 1282.5 | 185.9 |
| | | C4 | ng/mL | 6 | 9.8 | 3.1 | 6 | 113.4 | 20.3 |
| | | C5 | ng/mL | 6 | 10.1 | 2.7 | 6 | 112.9 | 18.5 |
| | | C6 | ng/mL | 6 | 10.5 | 2.3 | 6 | 112.3 | 17.2 |
| | | C7 | ng/mL | 6 | 10.1 | 2.1 | 6 | 110.7 | 15.6 |
| | | C8 | ng/mL | 6 | 9.7 | 1.9 | 6 | 109.2 | 14.7 |
| | | t½ | hr | 2 | 10.2 | 1.2 | — | — | — |
| | 7 | Tmax | hr | 6 | 2.8 | 0.7 | 6 | 2.7 | 0.3 |
| | | Tmin | hr | 6 | 7.8 | 3.6 | 6 | 11.2 | 4.9 |
| | | Cmax | ng/mL | 6 | 19.3 | 6.0 | 6 | 206.6 | 36.1 |
| | | AUC0-last | hr × ng/mL | 6 | 235.1 | 55.2 | 6 | 3269.2 | 467.6 |
| | | AUC0-inf | hr × ng/mL | 6 | 269.9 | 58.6 | 6 | 3725.3 | 555.8 |
| | | AUC0-4 | hr × ng/mL | 6 | 46.9 | 14.0 | 6 | 552.1 | 93.3 |
| | | AUC0-5 | hr × ng/mL | 6 | 57.0 | 16.9 | 6 | 694.9 | 116.0 |
| | | AUC0-6 | hr × ng/mL | 6 | 66.8 | 19.5 | 6 | 825.6 | 135.6 |
| | | AUC0-7 | hr × ng/mL | 6 | 75.9 | 21.8 | 6 | 945.7 | 153.1 |
| | | AUC0-8 | hr × ng/mL | 6 | 84.0 | 23.5 | 6 | 1056.9 | 169.8 |
| | | AUC0-12 | hr × ng/mL | 6 | 112.0 | 28.0 | 6 | 1446.1 | 219.8 |
| | | C4 | ng/mL | 6 | 10.3 | 3.1 | 6 | 149.0 | 26.1 |
| | | C5 | ng/mL | 6 | 10.0 | 2.8 | 6 | 136.8 | 22.2 |
| | | C6 | ng/mL | 6 | 9.6 | 2.5 | 6 | 124.6 | 18.9 |
| | | C7 | ng/mL | 6 | 8.6 | 2.0 | 6 | 115.7 | 17.6 |
| | | C8 | ng/mL | 6 | 7.7 | 1.5 | 6 | 106.8 | 16.8 |
| | | Cmin | ng/mL | 6 | 3.8 | 1.0 | 6 | 58.6 | 12.1 |
| | | Cavg | ng/mL | 6 | 7.4 | 1.6 | 6 | 97.2 | 13.6 |
| | | t½ | hr | 6 | 12.2 | 0.8 | 6 | 13.5 | 1.9 |

TABLE 11

Summary of PK parameter for 400 mg dose of compound (39) in an MR1 tablet dosage form.

| Study | | | | Esketamine | | | Noresketamine | | |
|---|---|---|---|---|---|---|---|---|---|
| Dose mg | Day | Parameter | Units | N | Mean | SE | N | Mean | SE |
| 400 | 1 | Tmax | hr | 6 | 4.7 | 1.0 | 6 | 3.8 | 0.8 |
| | | Tlag | hr | 6 | 0.0 | 0.0 | 6 | 0.0 | 0.0 |
| | | Cmax | ng/mL | 6 | 31.9 | 11.4 | 6 | 258.2 | 55.7 |
| | | AUC0-last | hr × ng/mL | 6 | 263.5 | 72.7 | 6 | 3012.3 | 522.3 |
| | | AUC0-inf | hr × ng/mL | 5 | 256.8 | 72.3 | 4 | 3274.0 | 896.9 |
| | | AUC0-4 | hr × ng/mL | 6 | 54.8 | 16.8 | 6 | 581.1 | 136.1 |
| | | AUC0-5 | hr × ng/mL | 6 | 76.3 | 25.5 | 6 | 779.4 | 169.9 |
| | | AUC0-6 | hr × ng/mL | 6 | 97.3 | 32.7 | 6 | 985.5 | 208.0 |
| | | AUC0-7 | hr × ng/mL | 6 | 116.1 | 38.1 | 6 | 1182.7 | 244.4 |
| | | AUC0-8 | hr × ng/mL | 6 | 131.2 | 42.1 | 6 | 1354.9 | 274.4 |
| | | AUC0-12 | hr × ng/mL | 6 | 176.7 | 51.9 | 6 | 1917.2 | 349.3 |
| | | C4 | ng/mL | 6 | 21.8 | 11.8 | 6 | 194.5 | 44.8 |
| | | C5 | ng/mL | 6 | 21.2 | 8.8 | 6 | 202.1 | 41.6 |
| | | C6 | ng/mL | 6 | 20.7 | 6.2 | 6 | 209.8 | 42.0 |
| | | C7 | ng/mL | 6 | 17.0 | 4.8 | 6 | 184.7 | 34.5 |
| | | C8 | ng/mL | 6 | 13.2 | 3.4 | 6 | 159.6 | 27.6 |
| | | t½ | hr | 5 | 8.6 | 1.1 | 4 | 9.4 | 1.1 |
| | 7 | Tmax | hr | 6 | 3.4 | 1.8 | 6 | 3.5 | 1.8 |
| | | Tmin | hr | 4 | 18.0 | 6.0 | 5 | 14.4 | 5.9 |
| | | Cmax | ng/mL | 6 | 18.8 | 6.4 | 6 | 182.2 | 40.0 |
| | | Cmin | ng/mL | 4 | 4.8 | 2.2 | 5 | 63.9 | 14.7 |
| | | Cavg | ng/mL | 4 | 10.4 | 3.5 | 5 | 110.4 | 16.9 |
| | | AUC0-last | hr × ng/mL | 6 | 266.5 | 90.5 | 6 | 3297.7 | 683.7 |
| | | AUC0-inf | hr × ng/mL | 3 | 503.6 | 209.3 | 5 | 4361.4 | 1010.1 |
| | | AUC0-4 | hr × ng/mL | 6 | 49.7 | 19.8 | 6 | 502.3 | 93.0 |
| | | AUC0-5 | hr × ng/mL | 6 | 61.6 | 24.2 | 6 | 637.6 | 120.7 |
| | | AUC0-6 | hr × ng/mL | 6 | 73.1 | 27.8 | 6 | 766.8 | 144.1 |
| | | AUC0-7 | hr × ng/mL | 6 | 83.8 | 30.8 | 6 | 888.4 | 164.2 |
| | | AUC0-8 | hr × ng/mL | 6 | 93.6 | 33.4 | 6 | 1000.3 | 181.6 |
| | | AUC0-12 | hr × ng/mL | 6 | 130.5 | 40.6 | 6 | 1428.7 | 242.3 |
| | | C4 | ng/mL | 6 | 12.1 | 4.8 | 6 | 138.3 | 30.2 |
| | | C5 | ng/mL | 6 | 11.7 | 4.0 | 6 | 132.3 | 26.0 |
| | | C6 | ng/mL | 6 | 11.3 | 3.2 | 6 | 126.3 | 22.0 |
| | | C7 | ng/mL | 6 | 10.3 | 2.8 | 6 | 116.8 | 19.3 |
| | | C8 | ng/mL | 6 | 9.3 | 2.3 | 6 | 107.3 | 16.8 |
| | | t½ | hr | 3 | 18.8 | 4.4 | 5 | 15.2 | 3.1 |

Adverse events were monitored following oral administration of tablet dosage forms to subjects. Common adverse events observed when esketamine is administered intranasally include sedation, dissociation, increase in blood pressure, and cognitive impairment. The number of adverse events observed following oral administration of 100 mg compound (39) in IR, MR1, MR2, and MR3 tablets is shown in Table 12. The number of adverse events is associated with a higher Cmax and with immediate release tablets.

TABLE 12

Total adverse events and mean pharmacokinetic parameters for 100 mg compound (39) dosage forms.

| | Tablet Dosage Form | | | |
|---|---|---|---|---|
| | IR | MR-1 | MR-2 | MR-3 |
| Relative Release Rate | Immediate | Moderate | Rapid | Slow |
| N | 12 | 12 | 12 | 12 |
| Total adverse events | 25 | 5 | 8 | 9 |
| Esketamine $C_{max}$ (ng/mL) | 40.6 | 7.5 | 11.5 | 5.6 |
| Esketamine $AUC_{0-last}$ (ng × hr/mL) | 87.1 | 46.2 | 58.8 | 51.2 |
| Noresketamine $C_{max}$ (ng/mL) | 217.8 | 70.1 | 113.9 | 50.5 |
| Noresketamine $AUC_{0-last}$ (ng × hr/mL) | 1081.3 | 817.6 | 1048.2 | 890.1 |

Certain pharmacokinetic parameters for esketamine and noresketamine following oral administration of equal molar doses of Compound (39) and esketamine are compared in Table 13.

TABLE 13

Pharmacokinetic parameters for esketamine and noresketamine following oral administration of equal molar doses of Compound (39) and esketamine.

| | | Esketamine | | Noresketamine | |
|---|---|---|---|---|---|
| Dose | N | $C_{max}$ (ng/mL) | $AUC_{0-last}$ (ng × hr/mL) | $C_{max}$ (ng/mL) | $AUC_{0-last}$ (ng × hr/mL) |
| Compound (39) 25 mg | 6 | [1] 8.2 | 15.2 | 51.4 | 255.7 |
| Esketamine 12 mg | 10 | [2] 5.3 (2.7) | 12.7 (6.1) | 38.4 (8.0) | 186 (5) |
| Ratio | | 1.5 | 1.2 | 1.3 | 1.4 |

[1] Mean
[2] Mean (Standard Deviation)

Finally, it should be noted that there are alternative ways of implementing the embodiments disclosed herein. Accordingly, the present embodiments are to be considered as illustrative and not restrictive, and the claims are not to be limited to the details given herein but may be modified within the scope and equivalents thereof.

What is claimed is:

1. An oral tablet dosage form comprising:
   from 35 wt % to 55 wt % of ((((S)-1-(2-chlorophenyl)-2-oxocyclohexyl)(methyl)carbamoyl)oxy)methyl dimethyl-L-valinate or a pharmaceutically acceptable salt thereof;
   from 0.5 wt % to 1.5 wt % of hydroxypropylmethyl cellulose E3;
   from 20 wt % to 40 wt % of a controlled release polymer, wherein the controlled release polymer comprises:
      from 50 wt % to 100 wt % of a hydroxypropylmethyl cellulose characterized by a methoxyl content from 22% to 24%; a pH in a 2% water at 25° C. from 5 to 8; a hydroxypropoxyl content 7.5% to 9.5%; a Brookfield viscosity from 80 mPa-s to 120 mPa-s as a 2% aqueous solution at 20° C.; and
      from 0 wt % to 50 wt % of a hydroxypropylmethyl cellulose characterized by a methoxyl content from 22% to 24%; a pH in 2% water at 25° C. from 5 to 8; a hydroxypropoxyl content 7.5% to 9.5%; a Brookfield viscosity from 2,600 mPa-s to 5,000 mPa-s as a 2% aqueous solution at 20° C.;
      wherein wt % is based on the total weight of the controlled release polymer;
   from 10 wt % to 20 wt % of microcrystalline cellulose;
   from 5 wt % to 15 wt % of sodium lauryl sulfate; and
   from 0.1 wt % to 1.0 wt % of magnesium stearate,
   wherein wt % is based on the total weight of the oral tablet dosage form.

2. The oral tablet dosage form of claim 1, wherein the ((((S)-1-(2-chlorophenyl)-2-oxocyclohexyl)(methyl)carbamoyl)oxy)methyl dimethyl-L-valinate or pharmaceutically acceptable salt thereof is ((((S)-1-(2-chlorophenyl)-2-oxocyclohexyl)(methyl)carbamoyl)oxy)methyl dimethyl-L-valinate HCl.

3. A method of treating a disease in a patient comprising orally administering to a patient in need of such treatment a therapeutically effective amount of the oral tablet dosage form of claim 1, wherein the disease is selected from depression and pain.

4. The method of claim 3, wherein the disease is depression.

5. The method of claim 4, wherein the depression is selected from major depressive disorder, dysthymia, persistent depression disorder, bipolar disorder, seasonal affective disorder, psychotic depression, peripartum depression, premenstrual dysphoric disorder, situational depression, atypical depression, treatment resistant depression, endogenous depression, cyclothymic disorder, and disruptive mood dysregulation disorder.

6. The method of claim 4, wherein the depression is major depressive disorder.

7. The method of claim 3, wherein the disease is pain.

8. The oral tablet dosage form of claim 1, wherein the oral dosage form comprises from 25 mg to 400 mg of the ((((S)-1-(2-chlorophenyl)-2-oxocyclohexyl)(methyl)carbamoyl)oxy)methyl dimethyl-L-valinate or pharmaceutically acceptable salt thereof.

* * * * *